(12) United States Patent
Soundararajan et al.

(10) Patent No.: US 10,660,814 B2
(45) Date of Patent: May 26, 2020

(54) ROBOTIC SURGICAL TABLE ADAPTER TO REDUCE EFFICIENCY OF ENERGY TRANSMISSION BETWEEN ATTACHED ROBOTIC ARMS

(71) Applicant: Verb Surgical Inc., Mountain View, CA (US)

(72) Inventors: Vijay Soundararajan, Santa Clara, CA (US); David James Cagle, Belmont, CA (US); Richard William Timm, Cincinnati, OH (US)

(73) Assignee: Verb Surgical Inc., Santa Clara, CA (US)

( * ) Notice: Subject to any disclaimer, the term of this patent is extended or adjusted under 35 U.S.C. 154(b) by 210 days.

(21) Appl. No.: 15/823,042

(22) Filed: Nov. 27, 2017

(65) Prior Publication Data

US 2018/0147106 A1    May 31, 2018

Related U.S. Application Data

(60) Provisional application No. 62/483,060, filed on Apr. 7, 2017, provisional application No. 62/443,393, filed
(Continued)

(51) Int. Cl.
*A61G 13/02*    (2006.01)
*A61G 13/10*    (2006.01)
(Continued)

(52) U.S. Cl.
CPC .............. *A61G 13/02* (2013.01); *A61B 34/30* (2016.02); *A61B 34/70* (2016.02); *A61B 90/50* (2016.02);
(Continued)

(58) Field of Classification Search
CPC ........ A61G 13/02; A61B 34/30; A61B 34/70; A61B 90/50; A61B 90/57; B25J 9/0009
See application file for complete search history.

(56) References Cited

U.S. PATENT DOCUMENTS

| | | | | |
|---|---|---|---|---|
| 4,300,198 A | * | 11/1981 | Davini ................ | B05B 13/0431 |
| | | | | 318/568.14 |
| 5,628,078 A | * | 5/1997 | Pennington .............. | A61B 6/04 |
| | | | | 5/613 |

(Continued)

FOREIGN PATENT DOCUMENTS

| | | |
|---|---|---|
| CA | 2913943 A1 | 12/2014 |
| WO | WO2007145544 A1 | 12/2007 |

(Continued)

OTHER PUBLICATIONS

International Search Report and Written Opinion dated Mar. 27, 2018, for related PCT Appln. No. PCT/US17/63311 13 Pages.
(Continued)

*Primary Examiner* — Thomas C Diaz
(74) *Attorney, Agent, or Firm* — Womble Bond Dickinson (US) LLP

(57) ABSTRACT

Apparatus and methods for providing a surgical table base with sufficient stiffness and adjustable support members with force feedback are described herein. In some embodiments, a base for a surgical table includes a base body to which other components of a surgical table can be coupled. A surgical table, and optionally a patient supportable by the surgical table, and any equipment to be carried by the surgical table, collectively representing a table load to be carried by the base body to support the surgical table on a surface. The base further includes a support assembly coupled to the base body to support the base body on the surface. The support assembly includes at least four support members. Each support member has a surface-engaging end
(Continued)

and can transmit a portion of a total load represented by the weight of the base and the table load through the surface-engaging end to the surface. The surface-engaging ends of any three of the four support members define a plane. One of the support members is adjustable to move the one support member relative to a plane defined by the three of the other support members and thereby to change the portion of the total load carried by one of the support members. The base further includes a load sensor operably coupled to the support assembly and disposed to detect the portion of the total load carried by one of the support members.

21 Claims, 37 Drawing Sheets

Related U.S. Application Data on Jan. 6, 2017, provisional application No. 62/426,966, filed on Nov. 28, 2016.

(51) Int. Cl.
| | |
|---|---|
| *A61G 13/06* | (2006.01) |
| *A61G 13/04* | (2006.01) |
| *A61B 34/30* | (2016.01) |
| *A61B 34/00* | (2016.01) |
| *G16H 40/63* | (2018.01) |
| *B25J 9/16* | (2006.01) |
| *A61B 90/50* | (2016.01) |
| *B25J 9/00* | (2006.01) |
| *A61B 90/57* | (2016.01) |
| *G16H 40/40* | (2018.01) |

(52) U.S. Cl.
CPC .............. *A61G 13/04* (2013.01); *A61G 13/06* (2013.01); *A61G 13/101* (2013.01); *B25J 9/0009* (2013.01); *B25J 9/1679* (2013.01); *G16H 40/63* (2018.01); *A61B 2090/571* (2016.02); *G05B 2219/39* (2013.01); *G05B 2219/41056* (2013.01); *G16H 40/40* (2018.01)

(56) References Cited

U.S. PATENT DOCUMENTS

| | | | |
|---|---|---|---|
| 5,903,940 A | 5/1999 | Volker et al. | |
| 6,132,368 A | 10/2000 | Cooper | |
| 6,331,181 B1 | 12/2001 | Tierney et al. | |
| 6,346,072 B1 | 2/2002 | Cooper | |
| 6,450,978 B1 | 9/2002 | Brosseau et al. | |
| 6,451,027 B1 | 9/2002 | Cooper et al. | |
| 6,535,756 B1 | 3/2003 | Simon et al. | |
| 6,587,750 B2 | 7/2003 | Akui et al. | |
| 6,608,628 B1 | 8/2003 | Ross et al. | |
| 6,659,939 B2 | 12/2003 | Moll et al. | |
| 6,678,907 B1 | 1/2004 | Voelker et al. | |
| 6,768,496 B2 | 7/2004 | Bieger et al. | |
| 6,788,018 B1 * | 9/2004 | Blumenkranz ........ B25J 9/0018 128/DIG. 7 |
| 6,866,671 B2 | 3/2005 | Tierney et al. | |
| 6,920,347 B2 | 7/2005 | Simon et al. | |
| 6,962,581 B2 | 11/2005 | Thoe | |
| 6,995,744 B1 | 2/2006 | Moore et al. | |
| 7,008,362 B2 | 3/2006 | Fitzgibbon | |
| 7,012,203 B2 | 3/2006 | Hanson et al. | |
| 7,048,745 B2 | 5/2006 | Tierney et al. | |
| 7,206,627 B2 | 4/2007 | Abovitz et al. | |
| 7,217,269 B2 | 5/2007 | El-Galley et al. | |
| 7,277,120 B2 | 10/2007 | Gere et al. | |
| 7,317,955 B2 | 1/2008 | McGreevy | |
| 7,331,967 B2 * | 2/2008 | Lee ...................... A61B 34/71 600/407 |
| 7,357,774 B2 | 4/2008 | Cooper | |
| 7,369,116 B2 | 5/2008 | Logue | |
| 7,379,790 B2 | 5/2008 | Toth et al. | |
| 7,498,532 B2 | 3/2009 | Kuhner et al. | |
| 7,524,320 B2 | 4/2009 | Tierney et al. | |
| 7,554,526 B2 | 6/2009 | Logue | |
| 7,594,912 B2 | 9/2009 | Cooper et al. | |
| 7,666,191 B2 | 2/2010 | Orban, III et al. | |
| 7,699,855 B2 | 4/2010 | Anderson et al. | |
| 7,727,244 B2 | 6/2010 | Orban, III et al. | |
| 7,768,702 B2 | 8/2010 | Hirose et al. | |
| 7,781,941 B2 | 8/2010 | Horvath et al. | |
| 7,783,133 B2 | 8/2010 | Dunki-Jacobs et al. | |
| 7,784,126 B2 | 8/2010 | Meissner et al. | |
| 7,789,874 B2 | 9/2010 | Yu et al. | |
| 7,789,875 B2 | 9/2010 | Brock et al. | |
| 7,819,885 B2 | 10/2010 | Cooper | |
| 7,840,042 B2 | 11/2010 | Kriveshko et al. | |
| 7,843,158 B2 | 11/2010 | Prisco | |
| 7,853,305 B2 | 12/2010 | Simon et al. | |
| 7,865,266 B2 | 1/2011 | Moll et al. | |
| 7,883,458 B2 | 2/2011 | Hamel | |
| 7,907,166 B2 | 3/2011 | Lamprecht et al. | |
| 7,922,439 B2 | 4/2011 | Kato | |
| 7,947,050 B2 | 5/2011 | Lee et al. | |
| 7,955,322 B2 | 6/2011 | Devengenzo et al. | |
| 7,983,793 B2 | 7/2011 | Toth et al. | |
| 8,004,229 B2 | 8/2011 | Nowlin et al. | |
| 8,062,288 B2 | 11/2011 | Cooper et al. | |
| 8,079,950 B2 | 12/2011 | Stern et al. | |
| 8,086,008 B2 | 12/2011 | Coste-Maniere et al. | |
| 8,095,200 B2 | 1/2012 | Quaid et al. | |
| 8,100,133 B2 | 1/2012 | Mintz et al. | |
| 8,105,338 B2 | 1/2012 | Anderson et al. | |
| 8,120,301 B2 | 2/2012 | Goldberg et al. | |
| 8,126,114 B2 | 2/2012 | Naylor et al. | |
| 8,131,031 B2 | 3/2012 | Lloyd | |
| 8,142,447 B2 | 3/2012 | Cooper et al. | |
| 8,147,503 B2 | 4/2012 | Zhao et al. | |
| 8,155,479 B2 | 4/2012 | Hoffman et al. | |
| 8,190,238 B2 | 5/2012 | Moll et al. | |
| 8,202,278 B2 | 6/2012 | Orban, III et al. | |
| 8,206,406 B2 | 6/2012 | Orban et al. | |
| 8,256,319 B2 | 9/2012 | Cooper et al. | |
| 8,332,072 B1 | 12/2012 | Schaible et al. | |
| 8,391,954 B2 | 3/2013 | Quaid | |
| 8,395,342 B2 | 3/2013 | Prisco | |
| 8,398,541 B2 | 3/2013 | DiMaio et al. | |
| 8,418,073 B2 | 4/2013 | Mohr et al. | |
| 8,469,947 B2 | 6/2013 | Devengenzo et al. | |
| 8,473,031 B2 | 6/2013 | Nixon et al. | |
| 8,504,136 B1 | 8/2013 | Sun et al. | |
| 8,506,555 B2 | 8/2013 | Morales | |
| 8,508,173 B2 | 8/2013 | Goldberg et al. | |
| 8,521,331 B2 | 8/2013 | Itkowitz | |
| 8,527,094 B2 | 9/2013 | Kumar et al. | |
| 8,541,970 B2 | 9/2013 | Nowlin et al. | |
| 8,562,594 B2 | 10/2013 | Cooper et al. | |
| 8,594,841 B2 | 11/2013 | Zhao et al. | |
| 8,600,551 B2 | 12/2013 | Itkowitz et al. | |
| 8,620,473 B2 | 12/2013 | Diolaiti et al. | |
| 8,624,537 B2 | 1/2014 | Nowlin et al. | |
| 8,628,518 B2 | 1/2014 | Blumenkranz et al. | |
| 8,634,957 B2 | 1/2014 | Toth et al. | |
| 8,638,056 B2 | 1/2014 | Goldberg et al. | |
| 8,672,922 B2 | 3/2014 | Loh et al. | |
| 8,682,489 B2 | 3/2014 | Itkowitz et al. | |
| 8,706,184 B2 | 4/2014 | Mohr et al. | |
| 8,715,167 B2 | 5/2014 | Stern et al. | |
| 8,747,288 B2 | 6/2014 | Strotzer et al. | |
| 8,749,189 B2 | 6/2014 | Nowlin et al. | |
| 8,749,190 B2 | 6/2014 | Nowlin et al. | |
| 8,761,337 B2 | 6/2014 | Naylor et al. | |
| 8,786,241 B2 | 7/2014 | Nowlin et al. | |
| 8,806,359 B2 | 8/2014 | Garibaldi et al. | |
| 8,816,628 B2 | 8/2014 | Nowlin et al. | |
| 8,823,308 B2 | 9/2014 | Nowlin et al. | |
| 8,828,023 B2 | 9/2014 | Neff et al. | |
| 8,831,782 B2 | 9/2014 | Itkowitz | |

(56) References Cited

U.S. PATENT DOCUMENTS

| | | |
|---|---|---|
| 8,870,861 B2 | 10/2014 | El-Galley et al. |
| 8,888,764 B2 | 11/2014 | Devengenzo et al. |
| 8,930,027 B2 | 1/2015 | Schaible et al. |
| 8,939,500 B2 | 1/2015 | Voigt et al. |
| 8,968,333 B2 | 3/2015 | Yu et al. |
| 8,989,903 B2 | 3/2015 | Weir et al. |
| 8,996,173 B2 | 3/2015 | Itkowitz et al. |
| 9,002,517 B2 | 4/2015 | Bosscher et al. |
| 9,026,247 B2 | 5/2015 | White et al. |
| 9,078,686 B2 | 7/2015 | Schena |
| 9,108,318 B2 | 8/2015 | Diolaiti |
| 9,129,422 B2 | 9/2015 | Mountney et al. |
| 9,179,980 B2 | 11/2015 | Yoon |
| 9,198,731 B2 | 12/2015 | Balaji et al. |
| 9,215,293 B2 | 12/2015 | Miller |
| 9,221,172 B2 | 12/2015 | Williamson et al. |
| 9,232,984 B2 | 1/2016 | Guthart et al. |
| 9,241,768 B2 | 1/2016 | Sandhu et al. |
| 9,254,572 B2 | 2/2016 | Strotzer |
| 9,256,936 B2 | 2/2016 | Jacobs et al. |
| 9,259,276 B2 | 2/2016 | Mintz et al. |
| 9,259,282 B2 | 2/2016 | Azizian et al. |
| 9,295,524 B2 | 3/2016 | Schena et al. |
| 9,320,568 B2 | 4/2016 | Orban, III et al. |
| 9,333,042 B2 | 5/2016 | Diolaiti et al. |
| 9,345,546 B2 | 5/2016 | Toth et al. |
| 9,433,288 B2 | 9/2016 | Voigt et al. |
| 9,486,159 B2 | 11/2016 | Coste-Maniere et al. |
| 2003/0000015 A1 | 1/2003 | Horlin |
| 2009/0260158 A1 | 10/2009 | Kazuno et al. |
| 2010/0287703 A1 | 11/2010 | Zapata |
| 2012/0154564 A1 | 6/2012 | Hoffman et al. |
| 2014/0100588 A1 | 4/2014 | Blumenkranz et al. |
| 2014/0107627 A1 | 4/2014 | Blumenkranz et al. |
| 2014/0130810 A1 | 5/2014 | Azizian et al. |
| 2014/0168073 A1 | 6/2014 | Chizeck et al. |
| 2014/0171965 A1 | 6/2014 | Loh et al. |
| 2014/0188131 A1 | 7/2014 | Toth et al. |
| 2014/0282196 A1 | 9/2014 | Zhao et al. |
| 2015/0032126 A1 | 1/2015 | Nowlin et al. |
| 2015/0045812 A1 | 2/2015 | Seo |
| 2015/0051733 A1 | 2/2015 | Nowlin et al. |
| 2015/0265356 A1 | 9/2015 | Schena |
| 2015/0321355 A1 | 11/2015 | Kishi |
| 2015/0320213 A1 | 12/2015 | Sorrell |
| 2016/0140875 A1 | 5/2016 | Kumar et al. |
| 2016/0157943 A1 | 6/2016 | Mintz et al. |
| 2016/0166345 A1 | 6/2016 | Kumar et al. |
| 2016/0184037 A1 | 6/2016 | Cooper et al. |
| 2016/0242860 A1 | 8/2016 | Diolaiti et al. |

FOREIGN PATENT DOCUMENTS

| | | |
|---|---|---|
| WO | WO-2014/151621 A1 | 9/2014 |
| WO | WO-2014/152694 A1 | 9/2014 |
| WO | WO-2014/201538 A1 | 12/2014 |
| WO | WO-2016/048738 A1 | 3/2016 |

OTHER PUBLICATIONS

International Preliminary Report on Patentability dated May 28, 2019, for related PCT Appln. No. PCT/US17/63311 8 Pages.
U.S. Appl. No. 15/717,599, filed Sep. 27, 2017, by Timm et al.
U.S. Appl. No. 15/785,341, filed Oct. 16, 2017, by Timm et al.
U.S. Appl. No. 15/785,331, filed Oct. 16, 2017, by Cagle et al.
U.S. Appl. No. 15/725,093, filed Oct. 4, 2017, by Wiggers.
U.S. Appl. No. 15/785,291, filed Oct. 16, 2017, by Cagle et al.
U.S. Appl. No. 15/822,986, filed Nov. 27, 2017, by Timm et al.
U.S. Appl. No. 15/823,006, filed Nov. 27, 2017, by Timm et al.
U.S. Appl. No. 15/706,112, filed Sep. 15, 2017, by Koenig.
U.S. Appl. No. 15/706,087, filed Sep. 15, 2017, by Cagle et al.
U.S. Appl. No. 15/788,730, filed Oct. 19, 2017, by Schaller et al.

* cited by examiner

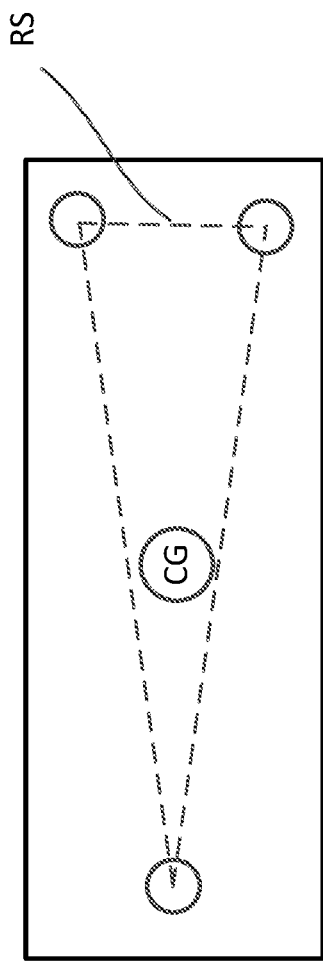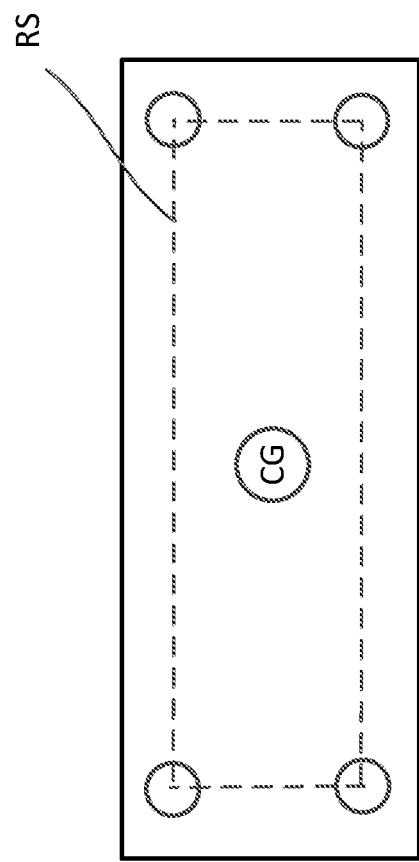
FIG. 2C
FIG. 2D

Section A-A

Section A-A

Section A-A

Section A-A

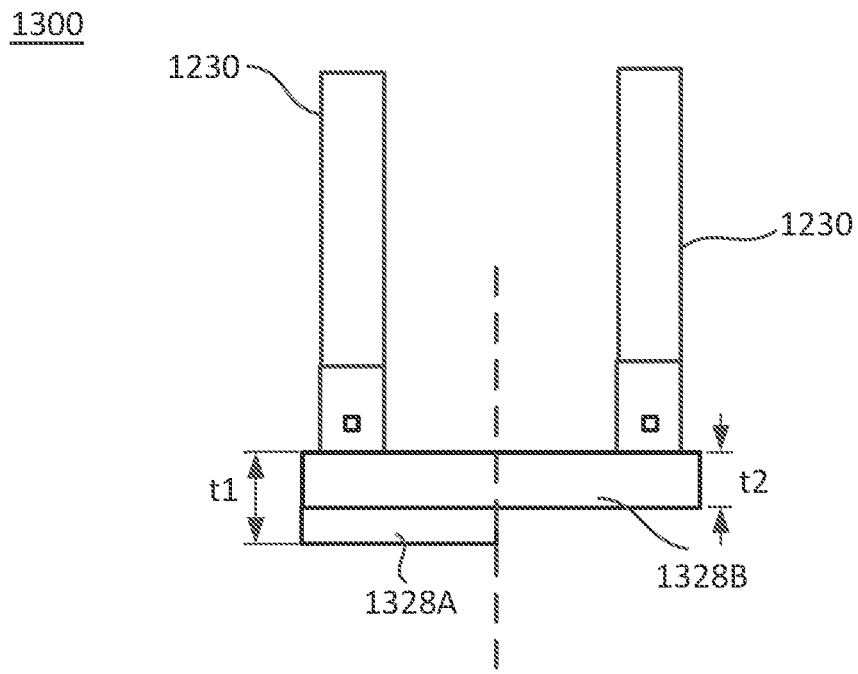
FIG. 27C
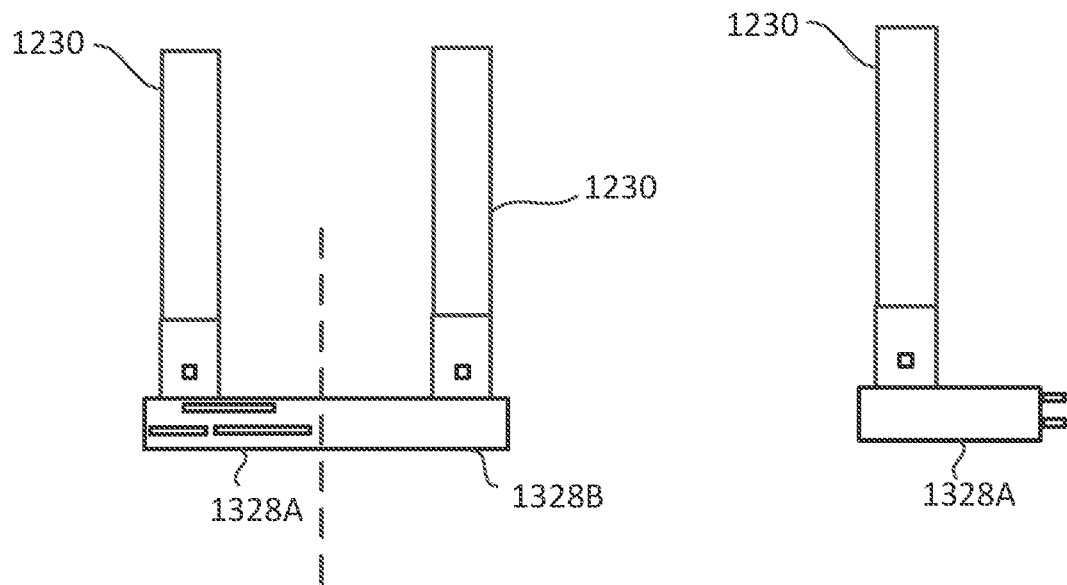
FIG. 27D
FIG. 27E

ROBOTIC SURGICAL TABLE ADAPTER TO REDUCE EFFICIENCY OF ENERGY TRANSMISSION BETWEEN ATTACHED ROBOTIC ARMS

CROSS REFERENCE TO RELATED APPLICATIONS

This application claims priority to and benefit of U.S. Provisional Patent Application No. 62/426,966, entitled "Surgical Table Base with High Stiffness and Adjustable Support Members with Force Feedback," filed Nov. 28, 2016; U.S. Provisional Patent Application No. 62/443,393, entitled "Robotic Surgical Table with Relatively High Resonant Frequency Structure to Reduce Efficiency of Energy Transmission Between Attached Robotic Arms," filed Jan. 6, 2017; and U.S. Provisional Patent Application No. 62/483,060, entitled "Robotic Surgical Table Adapter to Reduce Efficiency of Energy Transmission Between Attached Robotic Arms," filed Apr. 7, 2017; the disclosures of each of which are incorporated herein by reference in their entirety.

BACKGROUND

Some embodiments described herein relate to apparatus and methods for a base for a surgical table having four or more support members to support the base stably on a surface. Further embodiments described herein relate to surgical tables with robotic surgical arms, and apparatus and methods for reducing unwanted vibration at the working ends of the robotic arms. Yet further embodiments described herein relate to adapters for surgical tables with robotic surgical arms, and apparatus and methods for reducing unwanted vibration at the working ends of the robotic arms.

Stability of surgical tables during surgery is important to their safe and effective clinical use. Certain design characteristics improve the stability of surgical tables, such as a rigid support structure. In addition, it is also desirable for surgical tables to allow adjustment of patient position in one or more axes of motion, and to allow for wheeled transport around the hospital. The most common design of surgical tables is to have a large base sufficiently sized to prevent tipping, containing wheels, and having a means of locking to the floor to enhance stability.

One conflicting requirement with stability is dealing with floor irregularities. The problem is that to achieve stability, both in rigidity, as well as tipping, the base must be as large as possible. However, the base is also limited to a size that enables clinical access, which means that it must have a footprint no larger than the footprint of the table top. Thus, bases typically have a generally rectangular shape, and have four points of contact with the floor instead of the three needed for kinematic constraint.

Some surgical tables are mobile, can be wheeled around, and are frequently swapped in and out of an operating room based on the type of surgical procedure being performed. Such movement of the surgical tables within the operating room requires dealing with irregularities in the floor surface (e.g., variations in elevation of the floor surface). Given irregularities, such as drains, craftsmanship defects, bubbling, delamination of flooring, even dirt and grime, a rigid base with four points of contact may result in only three points in contact, and one in the air. This creates a situation where the table can rock back and forth, as is commonly observed in restaurant tables. Instability during surgery could cause irritation to surgeons and assistants at the very least or even a dangerous surgical situation. Thus, a solution is needed where the table is not only structurally rigid, but also mobile, and able to tolerate irregularities in the floor.

Further, robotic surgical systems can include robotic surgical arms that are coupled, directly or indirectly (e.g., via an adapter), to a surgical table on which a patient can be supported during a surgical procedure. The robotic surgical arms may support at their distal, working ends various devices, including surgical instruments, cannulae for providing access to the patient's body cavity(ies) and organ(s) for application of surgical instruments, imaging devices, lights, etc. In such systems, it is desirable to establish and maintain high positional accuracy for the devices mounted on the distal ends of the robotic arms.

Positional accuracy can be reduced or degraded by vibration of the distal ends of the robotic arms. Such vibration may be in the form of vibrational cross-talk, which is unwanted vibration occurring in one part of the system that originates in another part of the system. For example, vibration may be induced within a robotic arm, such as by operation of a motor driving movement of some portion of the arm relative to another portion of the arm and/or to the surgical table or other supporting structure, and the energy introduced into the arm by operation of the motor may propagate through the arm to the distal end, inducing vibration in the distal end. This arm may be referred to as the "active" arm. Alternatively, or additionally, energy introduced into the active arm, such as by operation of a motor within the active arm, may propagate through the active arm, through the table or other supporting structure, and through another robotic arm (which may be referred to as the "passive" arm) to the passive arm's distal end.

It is desirable to reduce vibrational cross-talk to enhance positional accuracy of the distal ends of robotic arms and the devices attached thereto.

SUMMARY

Apparatus and methods for providing a surgical table base with sufficient stiffness and adjustable support members with force feedback are described herein. In some embodiments, a base for a surgical table includes a base body having a lower side and an upper side to which other components of a surgical table can be coupled. A surgical table, and optionally a patient supportable by the surgical table, and any equipment to be carried by the surgical table, collectively represent a table load to be carried by the base body to support the surgical table on a surface. The base further optionally includes wheels, and includes a support assembly coupled to the base body to support the base body on the surface. A mechanism in a base having wheels allows switching the table from a mobile configuration to a fixed configuration by transferring load from the wheels to the support assembly. The support assembly includes at least four support members spaced about the base body. Each support member has a surface-engaging end and can transmit a portion of a total load represented by the weight of the base and the table load through the surface-engaged end to the surface. The surface-engaging ends of any three of the four support members define a plane. One of the support members is adjustable to move the surface-engaging end of the one support member relative to a plane defined by the surface-engaging ends of three of the other support members and thereby to change the portion of the total load carried by one of the support members. The base further includes a load sensor operably coupled to the support assembly and disposed to detect the portion of the total load carried by one of the support m embers.

Apparatus and methods for providing a pivotable surgical table with robotic surgical arms, having sufficient stiffness to limit unwanted vibration at the working ends of the robotic arms, are described herein. In some embodiments, a surgical table includes a base, a support column extending upwardly from the base and having an upper end, a table top, and a pivot assembly coupling the table top to the upper end of the support column. The pivot assembly includes a support flange attached to the upper end of the support column and has portions distributed about the support column. The pivot assembly further includes a primary load support, a first actuator and a second actuator. The primary load support has a lower end coupled to the support flange and an upper end having a pivotable coupling to the table top. The first actuator has a lower end coupled to the support flange at a first portion of the flange disposed on a first side of the support column and an upper end having a pivotable coupling to the table top. The first actuator is variable in length to pivot the table top about the pivotable coupling of the primary load support about a first pivot axis. The second actuator has a lower end coupled to the support flange at a second portion of the flange disposed on a second side of the support column opposite to the first side and an upper end having a pivotable coupling to the table top. The second actuator is variable in length to pivot the table top about the pivotable coupling of the primary load support about a second pivot axis different from the first pivot axis.

Apparatus and methods for providing an adapter coupleable to, and supportable by, a surgical table below a tabletop of the surgical table. The surgical table has a support coupled to the tabletop and a base coupled to the support. The adapter has a first section configured to be coupled to a proximal end portion of a first robotic arm and a second section configured to be coupled to a proximal end portion of a second robotic arm. The first section has a first stiffness and the second section has a second stiffness that is greater than the first stiffness. A distal end portion of the first robotic arm is coupleable to a first surgical tool and a distal end portion of the second robotic arm is coupleable to a second surgical tool.

BRIEF DESCRIPTION OF THE DRAWINGS

FIGS. 2C and 2D are schematic illustrations of a base for a table having three and four, respectively, support members.

FIG. 27C is a schematic side view of an adapter for a surgical table having a first section and a second section that share a monolithic material, and an additional piece of material added to the first section.

FIGS. 27D and 27E are schematic side and front views, respectively, of an adapter for a surgical table having a first section including a set of ribs.

DETAILED DESCRIPTION

Figure 1A:
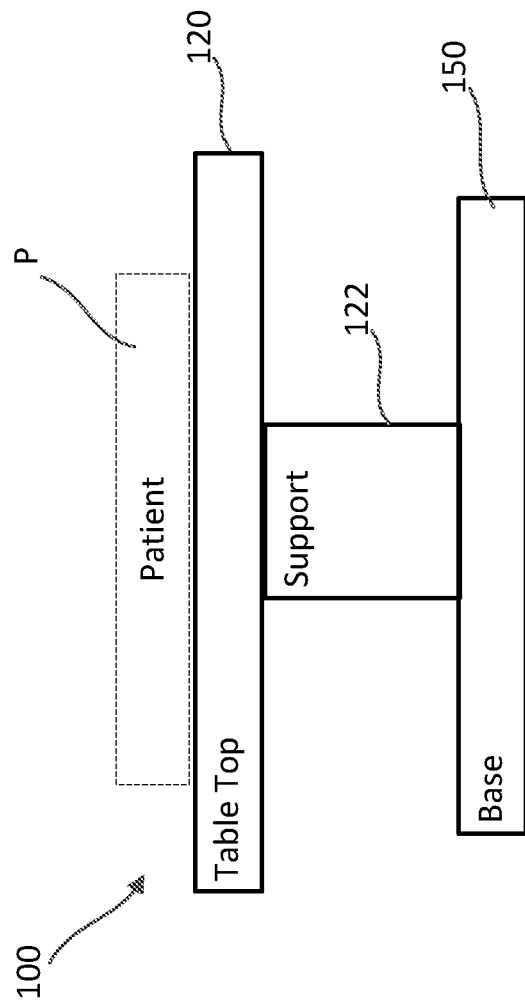
FIGS. 1A and 1B are schematic side and top views, respectively, of a surgical table, according to an embodiment.

Apparatus and methods for providing a surgical table base with sufficient stiffness and adjustable support members with force feedback are described herein with respect to FIGS. 1A-8. In some embodiments, a base for a surgical table includes a base body having a lower side and an upper side to which other components of a surgical table can be coupled. A surgical table, and optionally a patient supportable by the surgical table, and any equipment to be carried by the surgical table, collectively represent a table load to be carried by the base body to support the surgical table on a surface. The base further includes a support assembly coupled to the base body to support the base body on the surface. The support assembly includes at least four support members spaced about the base body. Each support member has a surface-engaging end and can transmit a portion of a total load represented by the weight of the base and the table load through the surface-engaged end to the surface. The surface-engaging ends of any three of the four support members define a plane. One of the support members is adjustable to move the surface-engaging end of the one support member relative to a plane defined by the surface-engaging ends of three of the other support members and thereby to change the portion of the total load carried by one of the support members. The base further includes a load sensor operably coupled to the support assembly and disposed to detect the portion of the total load carried by one of the support members.

In some embodiments, a method includes stabilizing a surgical table on a surface. The surgical table has a base. The surgical table and optionally a patient supportable by the surgical table, and any equipment carried by the surgical table collectively representing a total load supported on the surface. The base includes a support assembly. The support assembly includes at least four support members spaced about the base. Each support member has a surface-engaging end and can transmit a portion of the total load through the surface-engaging end to the surface. One of the support members is adjustable to move the surface-engaging end of the one support member. The base further includes a load sensor disposed to detect the portion of the total load carried by one of the support members. The method includes receiving a signal from the load sensor indicative of the portion of the total load carried by the one of the support members, and determining whether the portion of the total load is not within an acceptable range. The method further includes, if the portion of the total load is not within the acceptable range, causing the surface-engaging end of the adjustable support member to move relative to a plane defined by the surface-engaging ends of three of the other support members and thereby to change the portion of the total load carried by one of the support members. In some embodiments, stabilization may occur when at least a portion of the load is being transferred from the wheels to the support members to transition the table from a mobile to a fixed configuration. In other embodiments, stabilization may occur any time the support members are carrying at least a portion of the load of the table.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, a "set" can refer to multiple features or a singular feature with multiple parts. For example, when referring to a set of ribs, the set of ribs can be considered as one rib with distinct portions, or the set of ribs can be considered as multiple ribs.

Figure 1B:
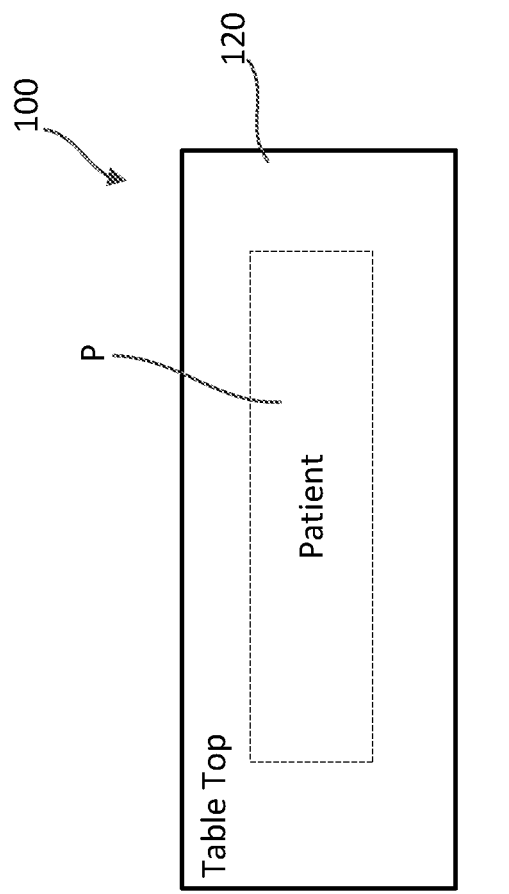

As shown schematically in FIGS. 1A-1B, a surgical table 100 includes a table top 120, a table support 122 and a table base 150. The table top 120 has an upper surface on which a patient P can be disposed during a surgical procedure, as shown schematically in FIG. 1A. The table top 120 is disposed on the support 122, which can be, for example, a pedestal, at a suitable height above the floor. The support 122 (also referred to herein as a pedestal) may provide for movement of the table top 120 in a desired number of degrees of freedom, such as translation in the Z axis (height above the floor), Y axis (along the longitudinal axis of the table), and/or X axis (along the lateral axis of the table), and/or rotation about the Z, Y, and/or X axis. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, or through any other suitable means. The support 122 for the table top 120 may be mounted to the base 150. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon or other medical professional access) and a certain distance from the support 122.

FIGS. 2A-8 illustrate various embodiments describing apparatus and methods for stabilizing a surgical table on a surface (e.g., a floor of an operating room). As described above and in accordance with various embodiments disclosed in more detail below, a surgical table can include a base configured to support other components of the surgical table (e.g., table top, pedestal, robotic arms and associated equipment, and/or the like) and a patient disposed on the surgical table, while simultaneously remedying undesirable consequences associated with irregularities in a floor or other surface on which the table is disposed, and/or other undesirable load imbalances (e.g., due to location and/or movement of equipment coupled to the surgical table and/or movement of a patient lying on the surgical table) during a surgical procedure.

Figure 2A:
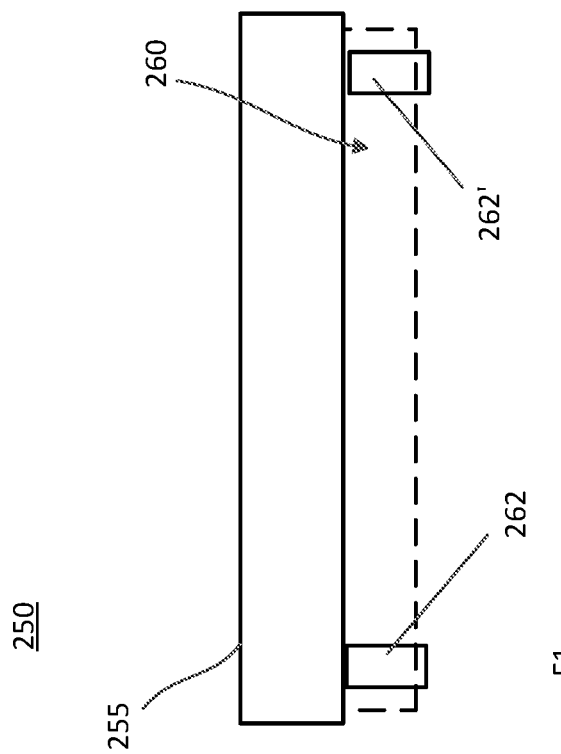
FIGS. 2A and 2B are schematic bottom and side views, respectively, of the base of the surgical table of FIGS. 1A and 1B.
Figure 2A:
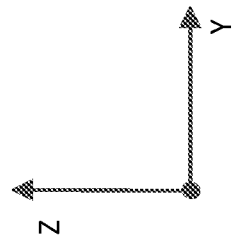

For example, as shown schematically in FIGS. 2A (bottom view) and 2B (side view), a base 250 for a surgical table includes a base body 255 and a support assembly 260 coupled to the base body 255. The base 250 is configured to support a surgical table load, and to monitor and/or adjust distribution of a total load (the table load together with the weight of the base) to a surface (e.g., a floor within a surgical room). The table load is a collective load including loads from various components of a surgical table, such as, for example, a table top, a pedestal, surgical tools and associated components, robotic arms, the like, and a patient. The surgical table can be the same or similar in structure and function to the surgical table 100 described above. For example, the surgical table can include a table support and a table top having an upper surface on which a patient P can be disposed during a surgical procedure.

Figure 2B:
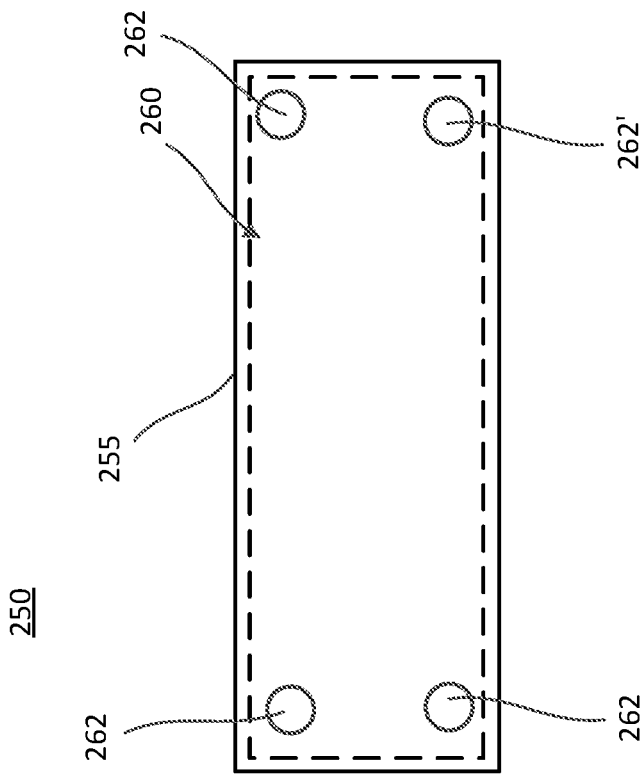
Figure 2B:
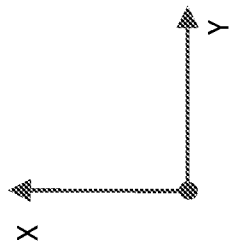

As shown in FIG. 2B and described in further detail herein, the support assembly 260 has a first end coupled to the base body 255, and a second end (also referred to herein as surface-engaging end) opposite and extending from the first end arranged to transmit the total load from the base body 255 to the surface. In some instances, the support assembly 260 and the base body 255 are monolithically constructed, while in other instances, the support assembly 260 is formed separately from and then coupled to the base body 255.

The support assembly 260 includes at least four support members 262. Each support member 262 is configured to transmit a portion of the table load to the surface. With four support members 262 spaced about the base body 255, any three support members 262 from the support assembly 260 define a plane. Specifically, the surface-engaging ends of any three support members 262 from the support assembly 260 define a plane. The three support members 262 can thus support the table on a surface, including an uneven surface, without wobbling or excessive vibration. However, it is desirable to support the table on the floor or other surface at four or more points to provide a more stable support, e.g., to be more resistant to tipping . . . . As shown in FIG. 2C, a base with three points of support on the floor or other surface has a triangular region of stability RS defined by the three points of support. If the center of gravity GC of the table (i.e. the total load) is disposed within the triangular RS, the table remains upright. However, if the CG is displaced outside of RS, the table can tip. The CG may shift for numerous reasons, including being on a non-level floor, movement of the table top sections, attachment of surgical accessories to the table, and/or movement of robotic arms attached to the table. As is apparent from FIG. 2C, relatively small movements of the CG can move it outside of TS. In contrast, as shown in FIG. 2D, a base with four points of support on the floor has a rectangular (or other four sided geometric shape) region of stability RS. The CG must be shifted a larger distance before it moves outside of RS. Thus, a base with four points of contact with the floor or other supporting surface is more stable, i.e. better able to accommodate movement of the CG without tipping.

A problem with having four support members, however, is that it can introduce another source of instability, e.g., wobbling or excessive vibration, or insufficient resistance to propagation of vibration. For example, if the floor surface is not flat and/or if any of the support members are uneven in length (e.g., due to manufacturing tolerances, defects, and/or wear and tear), one of the four support members may be out of contact with the floor, or may carry an insufficient portion of the total load to be in sufficiently firm contact with the floor. This problem is more pronounced for a more stiff structure in the base, because the base is less able to flex to accommodate variations in the floor, i.e. is less compliant.

To limit, reduce, or otherwise prevent such instability, at least one of the support members 262 is adjustable relative to the remaining support members 262 and/or the base body 255. For ease of explanation, in this embodiment, the adjustable support member is identified as 262'. Specifically, the adjustable support member 262' is adjustable to move its surface-engaging end relative to a plane defined by the surface-engaging ends of the three other support members 262. In this manner, in use, adjusting the adjustable support member 262' changes the portion of the total load carried by one or more of the support members 262 and/or the adjustable support member 262' itself.

Figure 5:
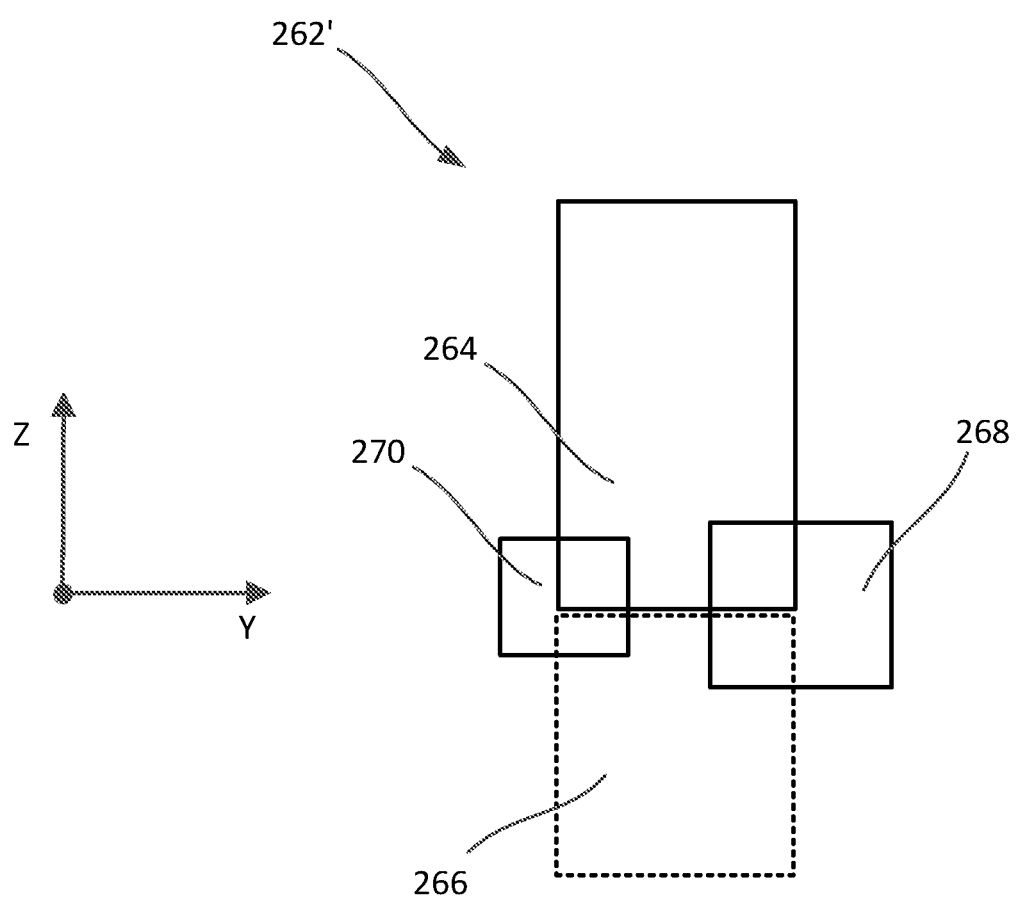
FIG. 5 is a schematic illustration of an adjustable support member according to an embodiment.
Figure 6:
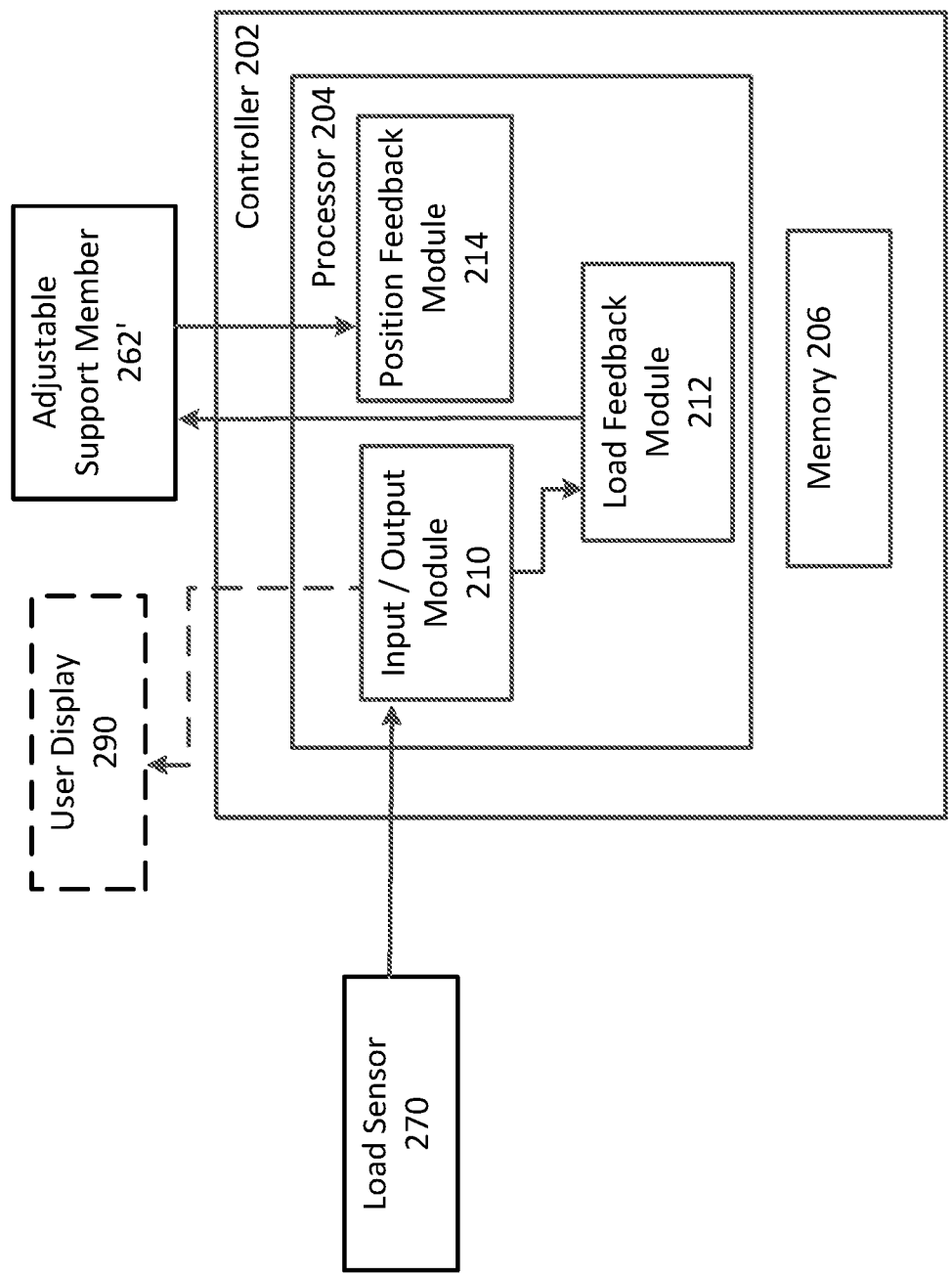
FIG. 6 is a schematic illustration of a controller of the surgical table of FIGS. 1A and 1B.
Figure 7A:
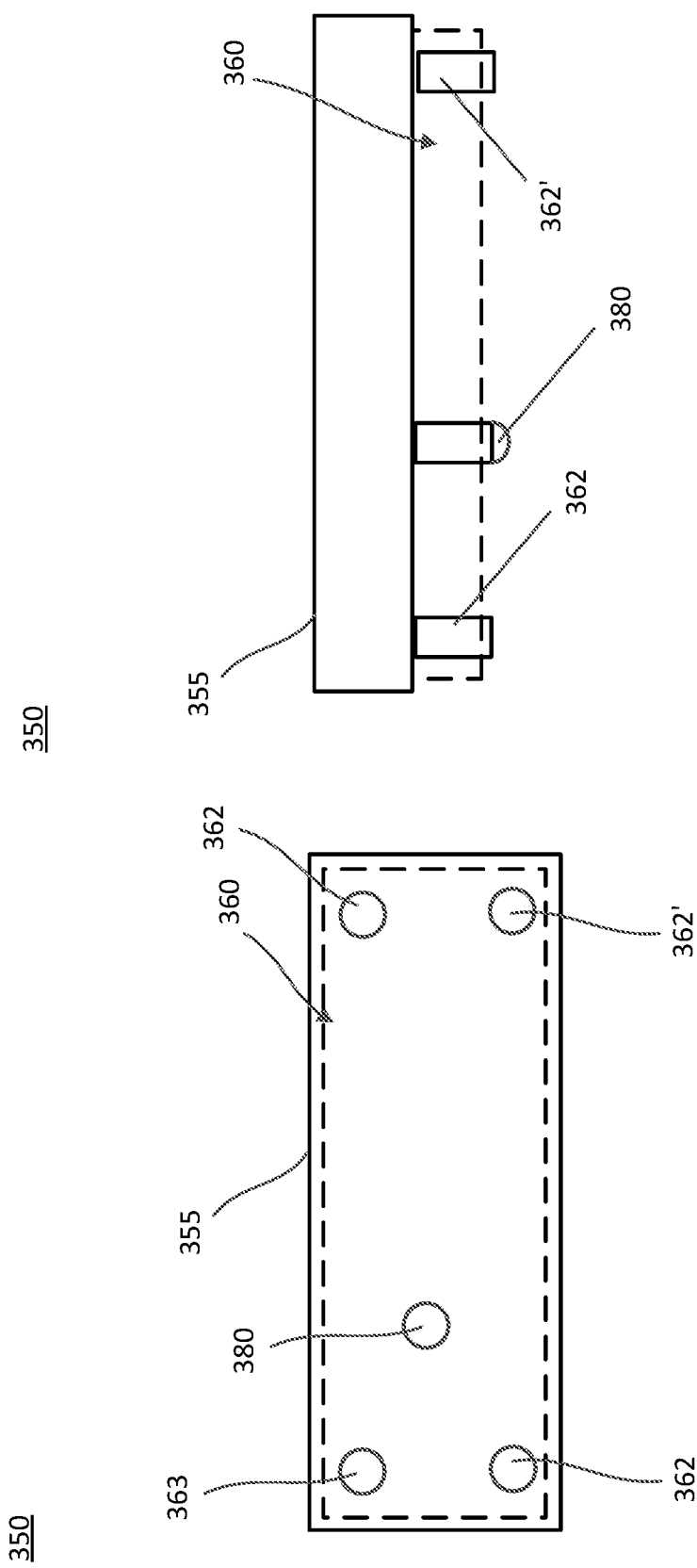
FIGS. 7A and 7B are schematic bottom and side views, respectively, of a base of a surgical table, according to an embodiment.
Figure 7B:

As also shown in FIG. 5, the adjustable support member 262' includes a fixed section 264 and a movable section 266 configured to move relative to the fixed section 264 and/or relative to the base body 255. The movable section 266 can be coupled to the fixed section 264 in any suitable manner. In some embodiments, for example, the movable section 266 and the fixed section 264 can be monolithically constructed, while in other embodiments the movable section 266 and the fixed section 264 can be formed separately and then joined together. Further, the movable section 266 can be movable relative to the fixed section 264 in any suitable manner. For example, in some embodiments, the movable section 266 can be at least partially slidably disposed within or with respect to the fixed portion 264. In this manner, for example, to shorten the height of the adjustable support member 262', the movable section 266 can be slid into or along a portion of the fixed portion 264. In other embodiments, the movable section 266 can be at least partially disposed about the fixed portion 264 such that the height of the adjustable support member 262' can be adjusted by sliding at least a portion of the fixed portion 264 into the movable portion 266. The relative movement of the movable section 266 and the fixed portion 264 can be produced by any suitable actuator 268. For example, the actuator 268 can include a motor and any suitable mechanism (e.g., rack and pinion, nut and leadscrew, hydraulic or pneumatic pump) to enable the motor to generate the desired motion. The motor may be electric, coupled to a suitable power source, and its activation and deactivation may be initiated by a control signal, manual user input (such as by a switch), or other suitable means. The actuator may be a hydraulic or pneumatic system, with the pressure and flow rate of the liquid or gas driven by any suitable mechanism such as a pump (driven by an electric motor, manually, etc.) and converted to linear motion via piston and cylinder.

Figure 3A:
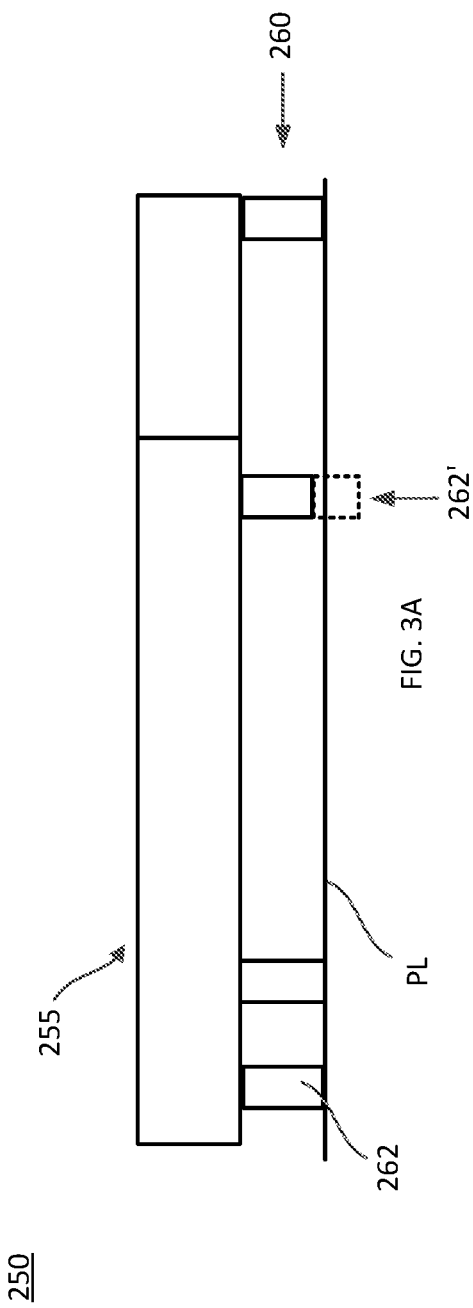
FIG. 3A is a schematic side view of the base of FIGS. 2A, 2B, illustrating the surface-engaging ends of three of the support members defining a plane and the surface-engaging end of the fourth support member movable relative to the plane.

To illustrate the adjustability of the adjustable support member 262', FIG. 3A illustrates schematically in side view the base of FIGS. 2A and 2B, showing the surface-engaging ends of three of the support members 262 defining a plane PL and the surface-engaging end of the adjustable support member 262' movable relative to the plane PL. The range of motion along the Z axis of the surface-engaging end of the adjustable support member 262' is shown in dotted line format. As illustrated in FIG. 3A, for example, the range of motion of the surface-engaging end of adjustable support member 262' is shown such that the surface-engaging end can extend above and below the plane PL defined by the remaining support members 262.

Figure 3B:
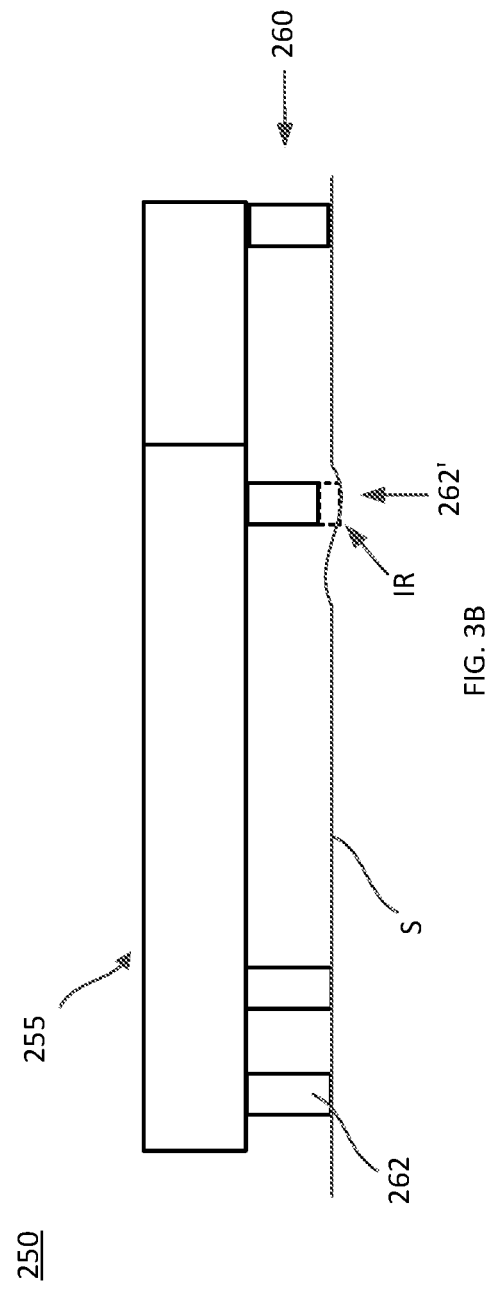
FIG. 3B is a schematic side view of the base of FIGS. 2A, 2B, illustrating the surface-engaging ends of three of the support members contacting a support surface that has an irregularity, and the surface-engaging end of the fourth support member movable relative to the irregularity.

To illustrate the adjustability of the support member 262' to accommodate a non-flat surface while optimizing base 250 stability. FIG. 3B illustrates schematically in side view the base body 255 and support assembly 260 of FIG. 3, showing the surface-engaging ends of three of the support members 262 contacting a flat portion of a support surface S that has an irregularity, and the surface-engaging end of the adjustable support member 262' is arranged such that it is in contact with the irregularity of the otherwise flat support surface S. In this manner, the adjustable support member 262' can be selectively placed in contact with the surface S such that the adjustable support member 262' and the remaining support members 262 transmit a desirable portion of the table load to the surface S, thereby optimizing load balancing and stability of the base 250.

Figure 4A:
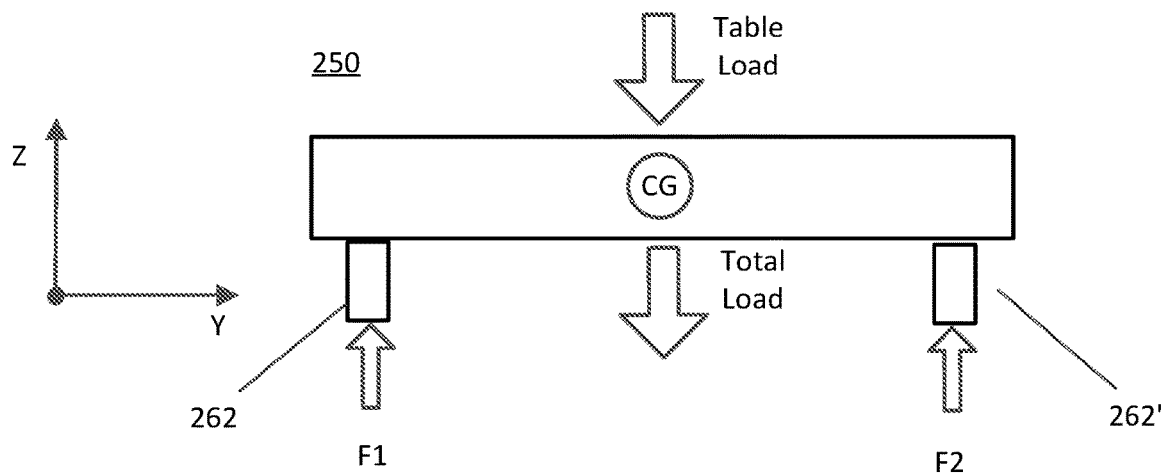
FIGS. 4A and 4B are schematic side and top views, respectively, of the base of FIGS. 2A, 2B, illustrating the distribution of the total load among the supporting members.
Figure 4B:
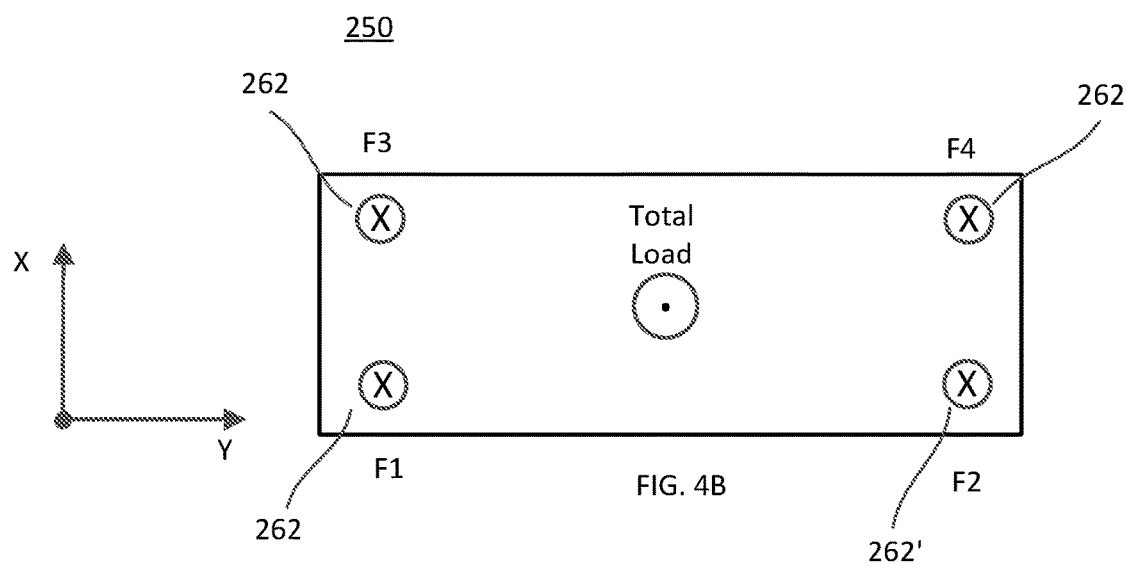

FIGS. 4A and 4B show the base 250. The forces imposed on it by the table load, and the resultant total load (the table load together with the weight of the base 250) acting through the center of gravity CG of the entire table (including the base), and the reactive force that is carried by each of the four support members 262, i.e. forces F1, F2, F3, and F4. As shown in the bottom view of the base in FIG. 4B, the forces F1-F4 are directed toward the base, in the +Z direction, indicated by an X. The total load acts in the −Z direction, indicated by a dot. Although the CG of the table is shown approximately centered between the four support members 262, the CG may be anywhere within the rectangle bounded by the support members 262. In addition, during a surgical procedure, the table load is dynamic. For example, various movements of components (e.g., movement of the table top or equipment such as robotic arms or surgical tools), movement of a surgeon or other medical professionals, and movement of the patient. This can result in changes to the magnitude of the table load and to the location of the center of gravity. Thus, the portion of the total load carried by each of the support members need not be equal, and can vary during a procedure. As noted above, irregularities in the floor or other support surface can affect the distribution of the total load across the four support members, and that distribution can be changed by movement of an adjustable support member.

To enable the detection and/or determination of the amount of force carried by one or more of the support members, and thus to enable an evaluation of whether the force for one or more of the support members should be changed by adjustment of one or more of the support members, the base 250 may include one or more load sensors 270 disposed and configured to detect a portion of the total table load carried by one of the support members 262. In this embodiment, a load sensor 270 is shown in FIG. 5 as being coupled to the adjustable support member 262', however, in other embodiments, the load sensor 270 can be coupled to any suitable portion of the base 250 such that the load sensor 270 can sensor the portion of the total load carried by at least one of the support members 262.

The load sensor 270 can be any suitable device configured to sense a load, such as a pressure sensor (to sense hydraulic and/or pneumatic pressure in embodiments in which the some or all of the total load is carried on a hydraulic and/or pneumatic element), a strain gauge sensor, a vibrating wire sensor, a capacitive sensor, and the like. For example, in some embodiments, the load sensor 270 can include a piezoelectric transducer, and the transducer can be coupled to a support member 262 (e.g., surface-engaging end of the support member 262 and/or the actuator 268) such that the transducer is strained by load carried by the support member. In some embodiments in which the adjustable support member 262 is hydraulically actuated, for example, the load sensor 270 can be disposed to detect a pressure of the hydraulic fluid.

The load sensor 270 may be operably coupled to a controller 202 that can, for example, control adjustment of the adjustable support member 262' via the actuator 268 based on measurements acquired by the load sensor 270. As shown schematically in FIG. 6, the controller 202 can include a memory 206, a processor 204, and various components or modules that are part of, or separate from, the processor 204 for interacting with other devices. For example in the illustrated embodiment, the processor 204 includes an input/output module 210 (or interface) that receives data signals from the load sensor 270 and may convey them to a load feedback module 212. Optionally (as indicated by dashed lines), the input/output module 210 may send output signals to a user display to provide a visual indication of information about the load carried by the support members, the location of the CG, and/or other information. The load feedback module 212 may receive the load signal from the load sensor 270, via the input/output module 210. The load feedback module 212 includes circuity, components, and/or code to produce a control signal to send to the actuator 268 to control movement of the movable portion 266 of the adjustable support member 262'. In some embodiments, the controller 202 includes a position feedback module 214 that receives a position, velocity, and/or acceleration information associated with movement of the movable portion 266 of the adjustable support member 262'. The controller 202 can be coupled to a computer (not shown) or other input/output device via the input/output module 210.

The processor 204 can be any processor configured to, for example, write data into and read data from the memory 206 of the controller 202, and execute the instructions and/or methods stored within the memory 206. Furthermore, the processor can be configured to control operation of the modules within the controller (e.g., the load feedback module 212 and the position feedback module 214). Specifically, the processor can receive a signal including user input, load data, pressure data, distance measurements or the like and determine an amount of movement for the adjustable support member 262', and/or an amount of force to be applied by the actuator 268. In other embodiments, the processor 204 can be, for example, an application-specific integrated circuit (ASIC) or a combination of ASICs, which are designed to perform one or more specific functions. In yet other embodiments, the processor can be an analog or digital circuit, or a combination of multiple circuits.

The memory 206 can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules can be implemented by the processor 204 and/or stored within the memory 206.

In some embodiments, in use, if a portion of the total load supported by a particular support member 262 as measured by the load sensor 270 falls below a predetermined threshold, the controller 270 can adjust the adjustable support member 262' such that the portion of the table load supported by that particular support member 262 returns to an acceptable level (e.g., a minimum threshold load or proportion of the load). Further, in some embodiments, the adjustable support member 262' can be operably coupled to a position sensor (not shown) that can sense a position of the adjustable support member 262', e.g., to determine the range of motion available to the adjustable support member. For example, the position sensor can detect a distance that the movable portion 266 of the adjustable support member 262' is extended from the fixed portion 264 to determine if and by how much the adjustable support member can be adjusted in either direction, e.g., raised or lowered relative to the floor surface. In other embodiments, any suitable position indication or measurement can be used (e.g., a percentage of the maximum extension height).

In some embodiments, the base 250 can include any suitable number of load sensors 270. For example, in some embodiments, each support member 260 can be operably coupled to a load sensor 270 such that a portion of the total load supported by each support member 270 can be determined. In this manner, in use, in response to detecting that a portion of the table load carried by any one or more of the support members 260 is not within an acceptable range, the adjustable support member 270 can be adjusted to change the portion of the table load carried by one or more of the support members 260. Maintaining suitable distribution of the table load in this way can encourage stability and limit, reduce or prevent wobbling or vibration of the surgical table 200.

In some embodiments, the support assembly 260 can include multiple adjustable support members 262' (e.g., two, three, four, five or more). In such embodiments, each adjustable support member 262' may be operably coupled to a load sensor 270, and each load sensor 70 can detect a portion of the total load carried by the adjustable support member 262' to which it is coupled. In such embodiments, each adjustable support member 262' can be independently controlled and adjusted (e.g., raised and/or lowered) to achieve a desired amount of total load distribution across the adjustable support members 262'.

Determining when to adjust an adjustable support member 260 can be based on any suitable table load balancing plan. For example, in some embodiments, a total load balancing plan can include defining an acceptable range of load to be carried by one or more of the support members 260 or adjustable support members 262'. This acceptable range, in some instances, can be based on the total load. In some instances, an acceptable range can be a percentage of the total load. For example, a total load balancing plan can include an acceptable range of about 1 percent to about 40 percent of the total load. In such cases, if the portion of the total load supported by any of the support members 262 falls outside of the acceptable range, one or more of the adjustable support members 262' will be adjusted to redistribute the total load until one or more, or all, of the support members 262 are supported a portion of the total load within the acceptable range.

In some embodiments, the total load balancing plan can include determining and/or tracking the location of the center of gravity CG of the surgical table 200. The center of gravity CG can be determined and/or calculated based on load information sensed by the load sensors 270. For example, as described in connection with FIG. 2D, the center of gravity CG may be centered within a region of stability RS bounded by the support members 262. In practice, however, as described above, due to irregularities in the support surface, dynamic forces results from surgical procedures, and/or movement of components of the table load during a surgical procedure, the location of the CG may shift to a location unacceptable close to the boundary of the RS. To detect such instances, in some embodiments, the location of the center of gravity CG can be determined and tracked in real-time (e.g., during a surgical procedure). If, for example, the center of gravity CG reaches a threshold distance from the boundary, the controller 202 can detect such an event and respond in any suitable manner, such as, for example, sending a signal to alert the surgeon or other medical staff, and/or a signal to adjust one or more of the adjustable support members 262' and/or additional stabilizing support members to provide desired stable support.

In some embodiments, adjustment of an adjustable support member may be initiated automatically in response to a determination that the total load needs to be redistributed. In another embodiment, adjustment of an adjustable support member may occur only when the base is being configured to a fixed arrangement with the floor. In other embodiments, the adjustable support member can be actuated manually by a user. In such embodiments, the base can be operably coupled to and/or can include a user display, such as user display 290 illustrated schematically in FIG. 6, and when the controller, for example, determines that the portion of the table load is not within an acceptable range, the controller can send a signal to the user display to generate on the user display an instruction to a user to actuate the actuator to move the surface-engaging end of the adjustable support member to change the portion of the table load carried by at least one of the support members. Further, in some instances, for example, when the controller determines that the portion of the table load is not outside of the acceptable range, the controller can send a signal to the user display to generate on the user display an indication that the user can cease activation of the actuator. In some embodiments, any type of visual, audio, and/or tactile feedback or alert can be generated to alert a user of a condition, such as an unacceptable load distribution.

Surgical tables, in addition to be structurally rigid and adjustable to accommodate for irregularities, can be mobile to allow for wheeled transport around the hospital. For example, as shown schematically in FIGS. 7A (bottom view) and 7B (side view), a base 350 for a surgical table includes a base body 355 and a support assembly 360 coupled to the base body 355. The base 350 can be the same or similar in structure and function to the base 350 described above, except the base 350 includes a wheel 380 to support the base 350 for movement on the surface (e.g., such that the surgical table can be wheeled around the operating room and/or around other areas of a hospital).

The base 350 can include any suitable number of wheels 380 to support the base 350 for movement on the surface, and can be coupled to the base 350 in any suitable location and any suitable manner. For example, in some embodiments, the base 350 can include two, three, four, or more wheels or casters to support the base 350 for movement on the surface. Further, in some embodiments, the wheel 380 is physically separate from the support members 360 (including the adjustable support member 362'), while in other embodiments, the wheel is included, coupled to, and/or integrated with a support member 360 (optionally including the adjustable support member 362'). For example, in some embodiments, one or more wheels 380 can be coupled to one or more of the support members 362 and can define at least in part the surface-engaging end of support member 362 to which it is coupled.

In some embodiments, one or more wheels 380 of the base 350 is movable upwardly (e.g., along the Z axis) relative to the surface-engaging ends of the support members to change the base 350 from a movable arrangement, in which the base 350 is supported only one the wheels 380 and movable relative to the surface on the wheels 380, to a fixed arrangement in which the base 350 is supported at least in part by at least two of the support members 362 and fixed relative to the surface. In this manner, the base 350 can be transitioned from a movable arrangement to a fixed arrangement, and vice versa, such that the surgical table can be moved around the hospital to a desired location, and then fixed to the surface in preparation for the surgical procedure. In some embodiments, in the fixed arrangement, the base 350 is supported only by the support members 362 (e.g., and not a wheel 380).

In some embodiments, the surface-engaging ends of at least two support members 362 are movably downwardly relative to the wheels 380. In this manner, the base 350 can be changed from a movable arrangement in which the base 350 is supported only on the wheels 380 and movable relative to the surface on the wheels 380, to a fixed configuration in which the base 350 is supported at least in party by the at least two support members 362 and fixed relative to the surface. In some embodiments, the surface engaging ends of at least four of the support members 362 are movable downwardly relative to the wheels 380, and in the fixed arrangement, the base 350 is supported only by the support members 362. Each of the support members 326 may be an adjustable support member, and downward movement of the surface engaging portion of each of the support members 362 may therefore include movement of an adjustable portion of the support member by an actuator in the same manner as the adjustable support member 262' described above.

Figure 8:
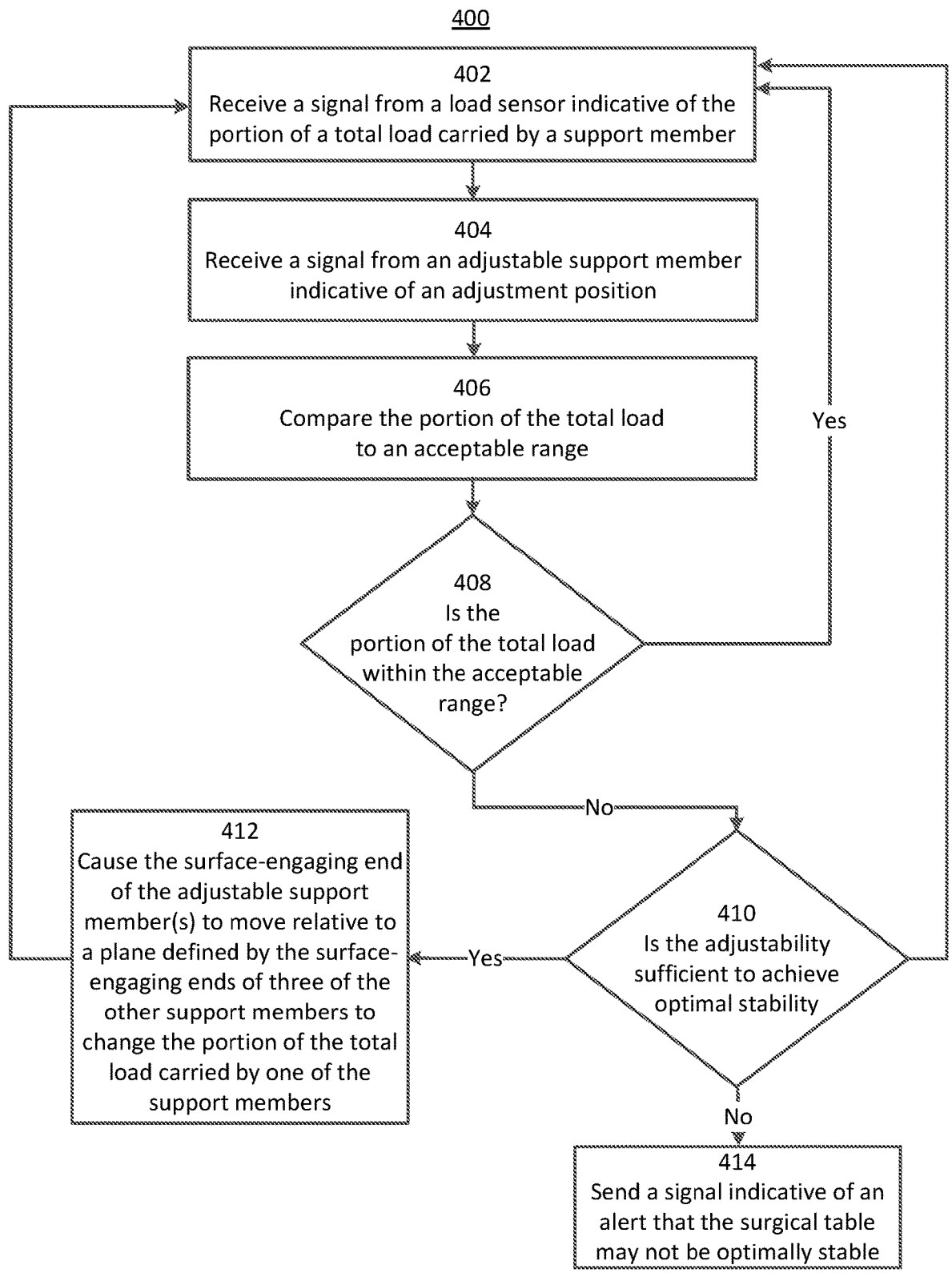
FIG. 8 is a flow chart illustrating a method according to an embodiment.

FIG. 8 is a flow chart that illustrates a method 400 of stabilizing a surgical table on a surface with a base such as the base 250 or 350 described above. In some embodiments, the method includes receiving at 402 a signal from the load sensor indicative of the portion of the total load carried by the one of the support members. The method optionally further includes receiving at 404 a signal from an adjustable support member indicative of an adjustment position (e.g., a position of the movable portion of the adjustable support member relative to the base body and/or fixed portion). The method further includes comparing at 406 the portion of the total load to an acceptable range. If, at 408, the portion of the total load is determined not to be within the acceptable range, then the method optionally further includes, at 410, determining the adjustability of the adjustment member based at least in part on the adjustment position and determining if the adjustability is sufficient to achieve optimal stability. If the adjustability is sufficient to achieve optimal stability, then the method further includes, at 412, causing the surface-engaging end of the adjustable support member to move relative to a plane defined by the surface-engaging ends of three of the other support members and thereby to change the portion of the total load carried by one of the support members. If the adjustability is determined to be insufficient to achieve optimal stability, then the method optionally further includes, at 414, sending a signal indicative of an alert that the surgical table may not be optimally stable. If, at 406, the portion of the total load is determined to be within the acceptable range, then the method may return to receiving at a later time another signal from the load sensor, and repeating the method from 402. The method may further include after causing the movement of the surface-engaging end of the support member to move and/or after sending the signal indicative of the alert, returning to 402 to receive an updated signal from the load sensor and repeating the method until the portion of the total load is within the acceptable range.

Although in various embodiments described herein, the support assembly as illustrated and explained included a particular number of support members, and particular number of which are adjustable, in other embodiments, a support assembly can include any suitable number of support members and any suitable number of adjustable support members. For example, in some embodiments, a support assembly can include four support members, and all four support members can be adjustable. In yet other embodiments, a support assembly can include more than four support members, such as, for example, five or more support members. For example, in some embodiments, a support assembly can include five support members, and four of the five support members can be non-adjustable relative to the base body and/or the other support member (e.g., the adjustable support member. Similarly, a base can include any suitable number of wheels and any suitable number of load sensors, and those wheels and load sensor can be coupled to any suitable portions of the base.

As described above, it is desirable to reduce unwanted vibration at the working ends of the robotic arms of a robotic surgical system. Robotic surgical systems can include robotic surgical arms that are coupled, directly or indirectly, to a surgical table on which a patient can be supported during a surgical procedure. The robotic surgical arms may support at their distal, working ends various devices, including surgical instruments, cannulae for providing access to the patient's body cavity(ies) and organ(s) for application of surgical instruments, imaging devices, lights, etc. In such systems, it is desirable to establish and maintain high positional accuracy for the devices mounted on the distal ends of the robotic arms.

Positional accuracy can be reduced or degraded by vibration of the distal ends of the robotic arms. Such vibration may be in the form of vibrational cross-talk, which is unwanted vibration occurring in one part of the system that originates in another part of the system. For example, vibration may be induced within a robotic arm, such as by operation of a motor driving movement of some portion of the arm relative to another portion of the arm and/or to the surgical table or other supporting structure, and the energy introduced into the arm by operation of the motor may propagate through the arm to the distal end, inducing vibration in the distal end. This arm may be referred to as the "active" arm. Alternatively, or additionally, energy introduced into the active arm, such as by operation of a motor within the active arm, may propagate through the active arm, through the table or other supporting structure, and through another robotic arm (which may be referred to as the "passive" arm) to the passive arm's distal end. It is desirable to reduce vibrational cross-talk to enhance positional accuracy of the distal ends of robotic arms and the devices attached thereto.

To address vibrational cross-talk and positional accuracy of the distal ends of robotic arms and the devices attached thereto, apparatus and methods for providing a robotic surgical system including a surgical table having a table top on which a patient can be disposed are described in various embodiments herein with respect to FIGS. 9A-23. In some embodiments, an apparatus includes a surgical table and robotic arms coupled, or coupleable to, the surgical table, with each robotic arm supporting a medical instrument, such as a surgical tool, tool driver, cannula, light, and/or imaging device. The surgical table includes a base, a pedestal or column, and a table top coupled to the column. Each of the robotic arms may be coupled to at least one of the table top, the column or the base. Each robotic arm provides two or more links between the proximal end of the arm (at which the arm is coupled to the table) and the distal end of the arm (at which the arm is coupled to the medical instrument). The links are coupled to each other, and may be coupled to the table and to the medical instrument, by a joint that provides one or more degrees of freedom of relative movement between the links coupled by the joint, and correspondingly one or more degrees of freedom of relative movement between the distal end of the robotic arm and the surgical table. The links and corresponding degrees of freedom allow for movement of the distal end of the robotic arm about and/or along the X, Y, and/or Z axes, to a desired location relative to the table top and/or a patient disposed thereon and/or a desired target portion of the anatomy of a patient disposed thereon. Relative movement of the links about the joints can be initiated and continued by operation of devices such as motors, and/or resisted or stopped by active devices such as motors and/or passive devices such as brakes. As noted above, such devices can introduce energy into the robotic surgical system, which can produce unwanted vibrations at the distal ends of the robotic arms.

In some embodiments, an apparatus includes a surgical table having a patient table top, an adapter coupled to the surgical table, and one or more robotic arms coupled to the adapter. In some embodiments, an apparatus can include a surgical table having a patient table top and an adapter/robotic arm assembly coupled to the surgical table. For example, the adapter and robotic arm can be an integral mechanism or component. Each of the adapter and the robotic arms, or an adapter/robotic arm assembly, can include one or more links to allow for movement of the adapter and/or arms about and/or along the X, Y, and/or Z axes, to a desired location relative to the table top and/or a patient disposed thereon and/or a desired target portion of the anatomy of a patient disposed thereon.

In some embodiments, the robotic arm can be releasably coupled to the surgical table. In some embodiments, the robotic arm can include a releasable coupling between its proximal end and its distal end, such that the proximal portion of the robotic arm can be coupled to the surgical table and the distal portion of the robotic arm can be removed from the proximal portion. In some embodiments, the proximal portion of the robotic arm can be implemented as an adapter, which may be fixedly coupled to the surgical table. The adapter can include a table interface structure or mechanism, a first link member pivotally coupled to the interface structure at a first joint, and a second link member coupled to the first link member at a second joint. In some embodiments, the second link member can be pivotally coupled to the first link member at the second joint. The second link member is also configured to be coupled to a robotic arm at a coupling that includes a coupling portion of the second link member and a coupling portion at a proximal or mounting end portion of the robotic arm. The robotic arm also includes a target joint at the mounting end portion of the robotic arm. In some embodiments, the target joint is included with the coupling portion at the mounting end portion of the robotic arm.

The robotic arm can be used to perform a surgical procedure on a patient disposed on the surgical table. The first joint can provide for rotational motion of the first link member about a vertical Z-axis relative to a table top of the surgical table and movement of the first link member and the second link member in lateral and longitudinal directions (also referred to herein as X-direction and Y-direction) relative to the table top of the surgical table. The second joint can provide a lift mechanism to allow for vertical movement (e.g., movement closer to, above, and/or further above, the table top of the surgical table) of the second link member and the mounting end portion of a robotic arm coupled thereto. The collective movement of the first link member and the second link member allows for the adapter and a robotic arm when coupled thereto to move between a variety of different positions relative to the surgical table. For example, the adapter and robotic arm can be moved to a stowed position, and various operating positions where the target joint of the robotic arm can be placed at a target location to perform a particular surgical procedure on a patient disposed on the table top of the surgical table. The motion of the first link member and the second link member also provides for movement of the adapter and robotic arm to various parked or clearance positions in which the adapter and robotic arm are disposed such that access to the patient is not obstructed. For example, it may be desirable to move the adapter and robotic arm during a surgical procedure to provide clearance for equipment such as an imaging device and/or to provide clearance for additional medical personnel in, for example, an emergency during the procedure. In some cases, an operating position can also be a parked position.

Figure 9A:
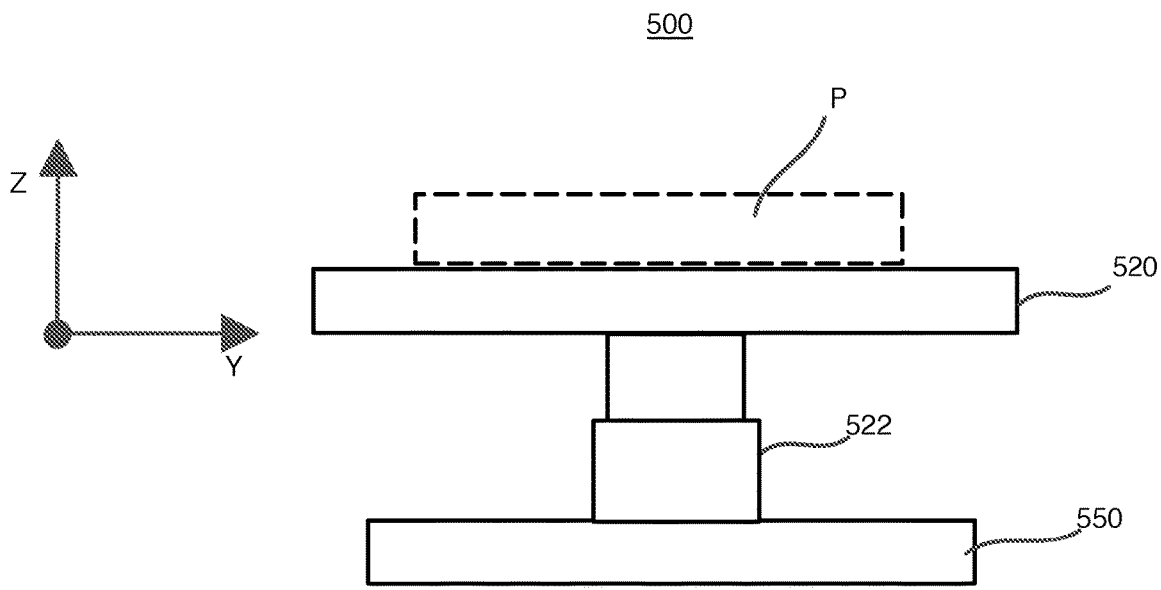
FIGS. 9A and 9B are schematic side and top views, respectively, of a surgical table, according to an embodiment.
Figure 9B:
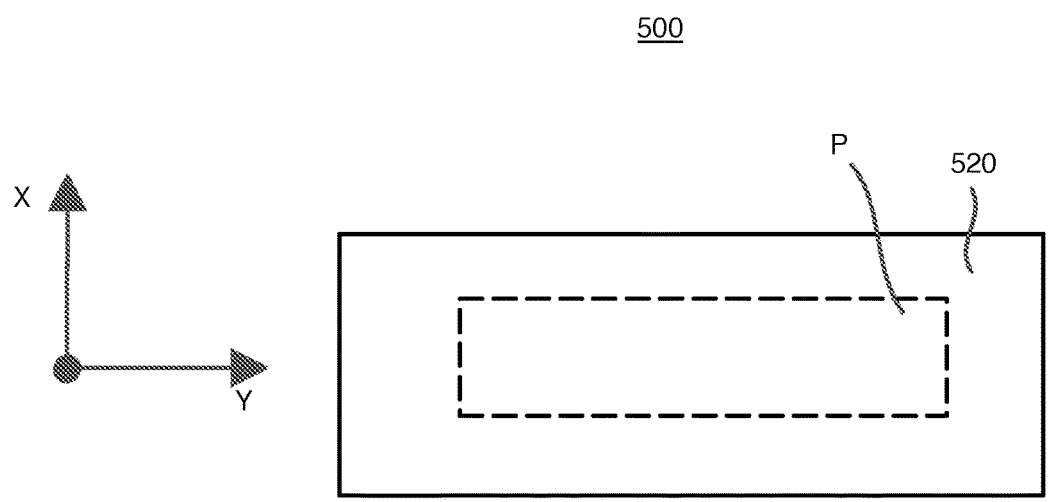

As shown schematically in FIGS. 9A-9B, a surgical table 500 includes a table top 520, a table support or column 522 and a table base 524. The table top 520 has an upper surface on which a patient can be disposed during a surgical procedure, as shown schematically in FIG. 9A. The table top 520 is disposed on the column 522, which can be, for example, a pedestal, at a suitable height above the floor. The column 522 may provide for movement of the table top 520 in a desired number of degrees of freedom. For example, as illustrated schematically in FIG. 9A, the column 522 may have two sections that telescope relative to each other to provide translation in the Z axis (height above the floor). Additionally, or alternatively, the table top 520 may be movable relative to the base 550 along the Y axis (along the longitudinal axis of the table), and/or the X axis (along the lateral axis of the table), and/or about the Z, Y, and/or X axis. The table top 520 may also include multiple sections that are movable relative to each other along/about any suitable axes, e.g., separate sections for each of the torso, one or both legs, and/or one or both arms, and a head support section. Movement of the table top 520 and/or its constituent sections may be performed manually, driven by motors, controlled remotely, etc. The column 522 for the table top may be mounted to the base 524, which can be fixed to the floor of the operating room, or can be movable relative to the floor, e.g., by use of wheels on the base. As shown schematically in FIG. 9A, in some embodiments, the height of the column 522 can be adjusted, which together with, for example, the motion (e.g., axial (longitudinal) or lateral motion) of the table top 520, can allow for the table top 520 to be positioned at a desired surgical site at a certain height above the floor (e.g., to allow surgeon access) and a certain distance from the column 520. This also can allow robotic arms 530 coupled to the table 500 to reach a desired treatment target on a patient disposed on the table top 520.

Figure 9C:
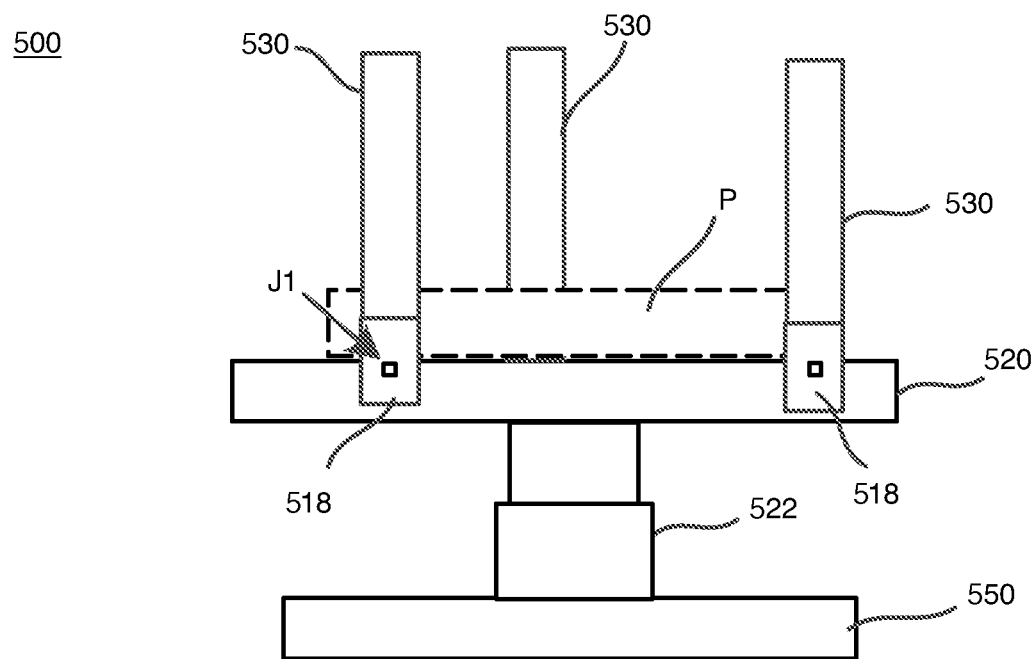
FIGS. 9C and 9D are a schematic side view and a schematic top view, respectively, of the surgical table of FIGS. 9A and 9B with robotic arms coupled thereto.
Figure 9D:
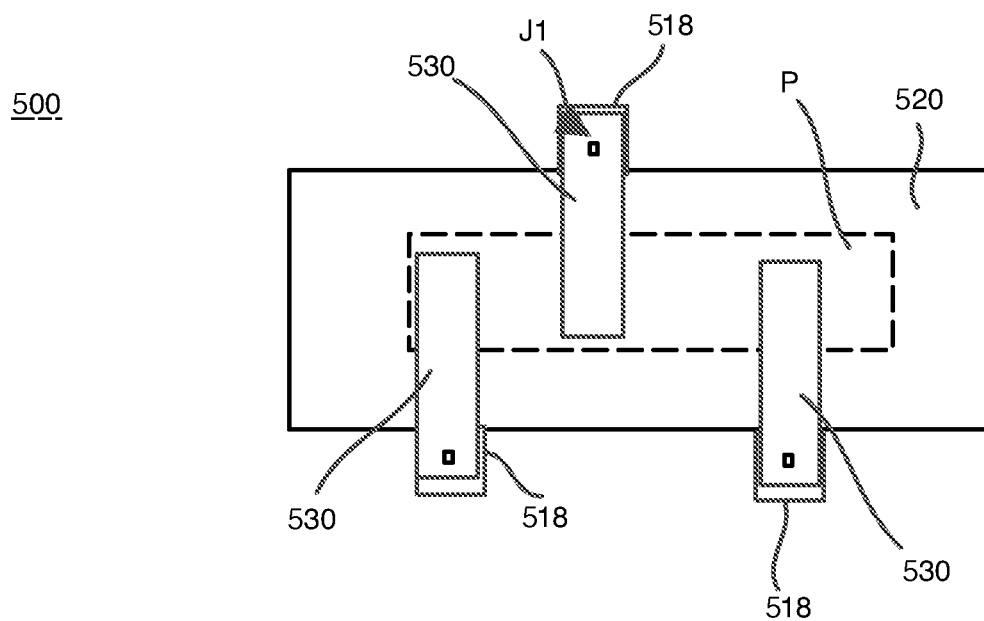

In a robotically assisted surgical procedure, one or more robotic arms 530 can be disposed in a desired operative position relative to a patient disposed on the table top 520 of the surgical table 500 (also referred to herein as "table"), as shown schematically in FIGS. 9C and 9D. The robotic arm(s) can be used to perform a surgical procedure on a patient disposed on the surgical table 500. In particular, the distal end of each robotic arm can be disposed in a desired operative position so that a medical instrument coupled to the distal end of the robotic arm can perform a desired function.

In accordance with various embodiments, each robotic arm 530 may be permanently, semi-permanently, or releasably coupled to the table top 520 via a coupling 518, as shown in FIGS. 9C and 9D. The coupling 518 can include a variety of different coupling mechanisms, including a coupling portion (not shown) on the table top 520 that can be matingly coupled to a coupling portion (not shown) on the robotic arm. Each robotic arm 530 can be coupled at a fixed location on the table 500 or can be coupled such that the robotic arm 530 can be movable to multiple locations relative to the table top 520 and/or a patient disposed on the table top 520 as described in more detail herein. For example, the robotic arm 530 can be moved relative to the table top 520 and/or a specific target treatment location on the patient. In some embodiments, the axial motion (e.g., in the Y-axis direction) of the table top 520 can assist in allowing the arms 530 (and therefore, the medical instrument or tool coupled to the distal end of the arm) to reach the desired anatomy on the patient or provide clearance for access to the patient as needed. In some embodiments, the combination of vertical movement of the column 522, axial movement of the table top 520 and movement of, for example, links in the robotic arm 530 allow the robotic arm to be placed in a position where it can reach the anatomy of the patient at the required height over the floor.

Figure 10A:
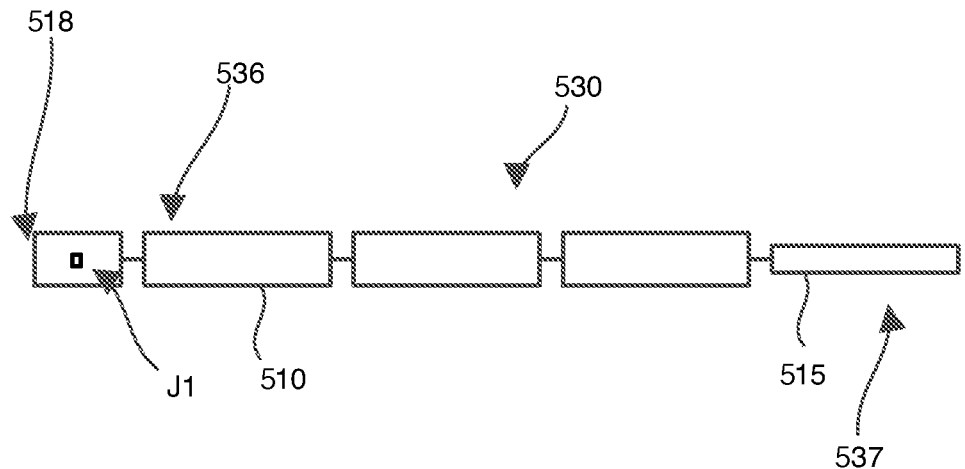
FIG. 10A is a schematic side view of a robotic arm, according to an embodiment, shown in an extended or use configuration.
Figure 10B:
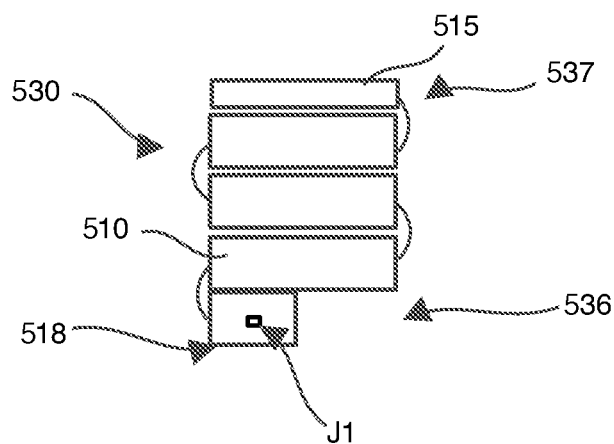
FIG. 10B is a schematic side view of the robotic arm of FIG. 10A, shown in a collapsed or folded configuration.

As shown schematically in FIGS. 10A and 10B, each robotic arm 530 can include a distal end portion 537 and a proximal end portion 536. The distal end portion 537 (also referred to herein as "operating end") can include or have coupled thereto a medical instrument or tool 515. The proximal end portion 536 (also referred to herein as the "mounting end portion" or "mounting end") can include the coupling portion to allow the robotic arm 530 to be coupled to the table top 520 of the table 500. The robotic arm 530 can include two or more link members or segments 510 coupled together at joints that can provide for translation along and/or rotation about one or more of the X, Y and/or Z axes. The coupling portion of the robotic arm 530 to couple the robotic arm 530 to the table top 522 at the coupling 518 can be disposed at the distal or mounting end 536 of the arm 530 and may be coupled to a segment 510 or incorporated within a segment 510. The robotic arm 530 also includes a target joint J1 disposed at or near the mounting end 536 of the robotic arm 530 that can be included within the coupling portion of the coupling 518 or disposed on a link or segment 510 of the robotic arm 530 coupled to the coupling portion. The target joint J1 can provide a pivot joint to allow a distal segment of the robotic arm 530 to pivot relative to the table top 520. The robotic arm 530 can be moved between various extended configurations for use during a surgical procedure, as shown in FIG. 10A, and various folded or collapsed configurations for storage when not in use, as shown in FIG. 10B.

Figure 11A:
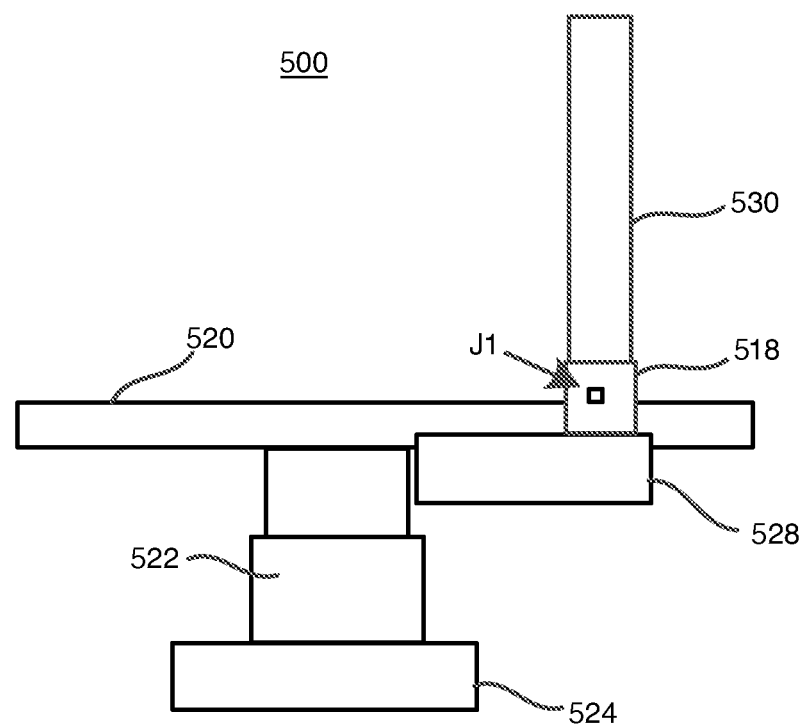
FIGS. 11A and 11B are a schematic side view and a schematic top view, respectively, of the surgical table of FIGS. 9A and 9B with an adapter and robotic arm coupled thereto.
Figure 11B:
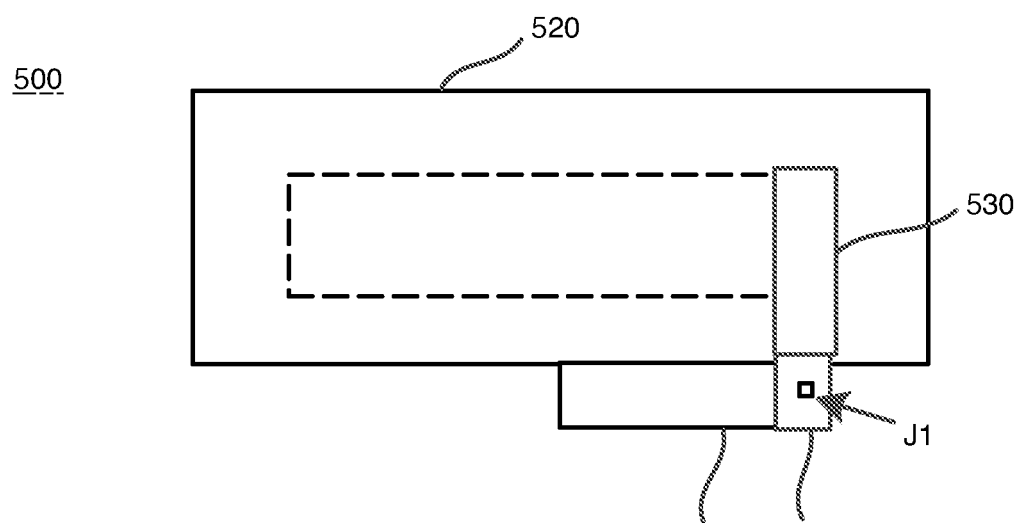

In some embodiments the connection between the surgical table and the distal end of the robotic arm (and thus the position and orientation of the medical instrument at the distal end of the robotic arm relative to the patient), is implemented with an adapter 528 and robotic arms) 530 coupled to the adapter 528, as shown in FIGS. 11A and 11B. The adapter 528 can be separate from, but engageable with, or coupleable to, the surgical table 500, or can be fixedly attached to the surgical table 500. The adapter 528 can be coupled to, for example, the column 522, the table base 524 and/or the table top 520 of the table 500. However, the distinction between an adapter and robotic arm can be disregarded, and the connection between the surgical table and the distal end of the robotic arm can be conceptualized and implemented as a series of links and joints that provide the desired degrees of freedom for movement of the medical instrument, i.e. at the distal end of the connection. The connection may include a releasable coupling at any one or more link(s) or joint(s) or any location along the series of links and joints.

As described herein, in some embodiments, the various sections of the table top 520 can move relative to each other (e.g., can be tilted or angled relative to each other) and/or the table top 520 can be moved (e.g., tilted, angled) relative to the column 522 and/or the base 524 of the surgical table 500. In some embodiments, it is contemplated that the adapter 528 and robotic arms 530 coupled thereto can move with the torso section of the table top 520 such that the frame of reference to the X, Y and Z axes for various embodiments remains relative to the top surface of the table top 520. In some embodiments, the adapter 528 and robotic arms 530 can be coupled to the support pedestal 522 of the table 500 and when the table top 520 is moved relative to the support 522, the positioning of the adapter 528 and arms 530 can be coordinated with the movement of the table top 520.

Figure 12A:
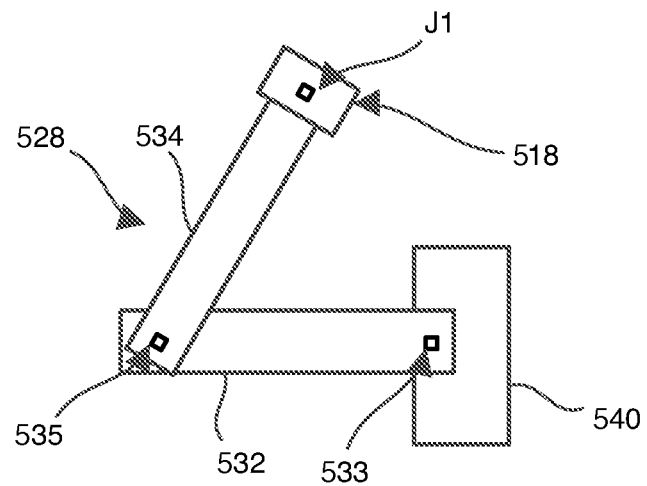
FIG. 12A is a schematic side view of an adapter, according to an embodiment, shown in an extended or use configuration.
Figure 12B:
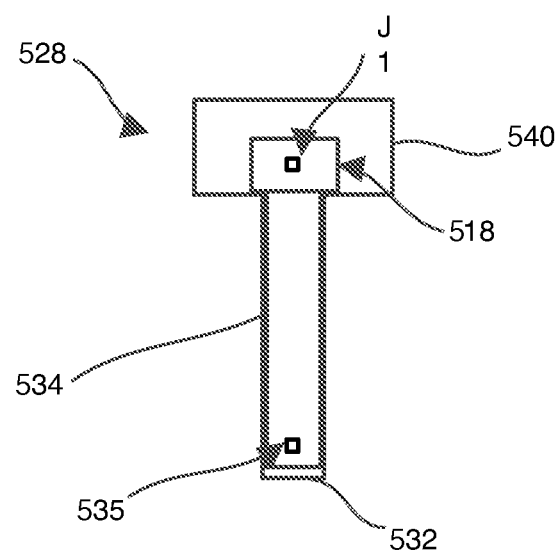
FIG. 12B is a schematic side view of the adapter of FIG. 12A, shown in a collapsed or folded configuration.

As shown schematically in FIGS. 12A and 12B, the adapter 528 can include a table interface structure or mechanism 540, and one or more link members. In this example embodiment, the adapter 528 includes a first link member 532 coupled to the interface structure 540 at a first joint 533, and a second link member 534 coupled to the first link member 532 at a second joint 535. In some embodiments, the first link member 532 can be pivotally coupled to the table interface structure 540 at the first joint 533. In some embodiments, the first link member 532 can be coupled to the table interface structure 540 with a joint that provides for linear motion. In some embodiments, the second link member 534 can be pivotally coupled to the first link member at the second joint. Other types of coupling joints for the first joint 533 and the second joint 535 can alternatively be used. Thus, various different types of coupling joints (e.g., linear, rotational) can be used between the link members of the adapter to achieve a desired movement and reach of the adapter. The second link member 534 is also coupleable to a robotic arm 530 at a coupling 518 (also referred to herein as "coupling joint"). The adapter 528 can be moved between various extended configurations for use during a surgical procedure as shown in FIG. 12A, and various folded or collapsed configurations for storage when not in use, as shown in FIG. 12B.

In some embodiments, the adapter 528 can include more than two link members. For example, an adapter can include a third link member (not shown) coupled to the second link member 534 between the second link member 534 and the coupling 518 to the robotic arm 530. In other embodiments, more than three link members can be included. The number and size of link members can vary such that the adapter 528 can provide a longer or shorter reach to extend the robotic arm 530 (e.g., the target joint J1 discussed below), for example, further above the patient, for larger patients. It can also be used to extend the position of the robotic arm 530 further under the table top 520 when the arm 530 is moved to a position on an opposite side of the table 500 as described in more detail below (e.g., the arm is moved to the opposite side to have three arms on one side of the table). The first joint 533 and the second joint 535 of the adapter 528 can provide for movement of the robotic arm 530 along and/or about the X, Y, and/or Z axes.

In accordance with various embodiments, each robotic arm 530 may be permanently, semi-permanently, or releasably coupled to the adapter 528 via the coupling 518. The coupling 518 can include a variety of different coupling mechanisms, including a coupling portion (not shown) on the adapter 528 that can be matingly coupled to a coupling portion (not shown) on the robotic arm. Each robotic arm 530 can be coupled at a fixed location on the table 500 or can be coupled such that the robotic arm 530 can be movable to multiple locations relative to the table top 520 and/or a patient disposed on the table top 520 as described in more detail herein. For example, the robotic arm 530 can be moved relative to the table top 520 and/or a specific target treatment location on the patient. In some embodiments, the axial motion (e.g., in the Y-axis direction) of the table top 520 can assist in allowing the arms 530 (and therefore, the medical instrument or tool coupled to the distal end of the arm) to reach the desired anatomy on the patient or provide clearance for access to the patient as needed. In some embodiments, the combination of vertical movement of the support pedestal 522, axial movement of the table top 520 and movement of, for example, the first link member 532 and the second link member 534, allows for placement of the robotic arms 530 in a position where it can reach the anatomy of the patient at the required height over the floor.

Some structural requirements for the adapter 528 can include providing a rigid support of the robotic arm 530 while maintaining adjustability for pre-operative and intra-operative position changes of the robotic arm 530. In some embodiments, the table adapter 528 can include a means of holding or locking the adapter 528 at a fixed position to withstand, for example, the effects of gravity, inertial effects due to robotic arm motion, and/or to withstand accidental bumps from a user or another part of the robotic system (including other robotic arms or table motion). The table adapter 528 can also include one or more sensors for measuring the spatial position of the adapter 528 and/or angles and displacements of various joints and coupling points of the adapter 528.

The collective motion of the first link member 532 and the second link member 534 of the adapter 528 can provide for movement of the coupling 518, and therefore, movement of a robotic arm 530 coupled thereto along and/or about the X, Y, and/or Z axes. For example, the target joint J1 of the robotic arm 530 can be moved to various target treatment locations relative to the table 500 to perform a variety of different surgical procedures on a patient disposed thereon. The collective motion of the first link member 532 and the second link member 534 also allows the adapter 528 and robotic arm 530 to move between a variety of different positions relative to the surgical table 500 including stowed positions, operating positions and parked or clearance positions.

Figure 13:
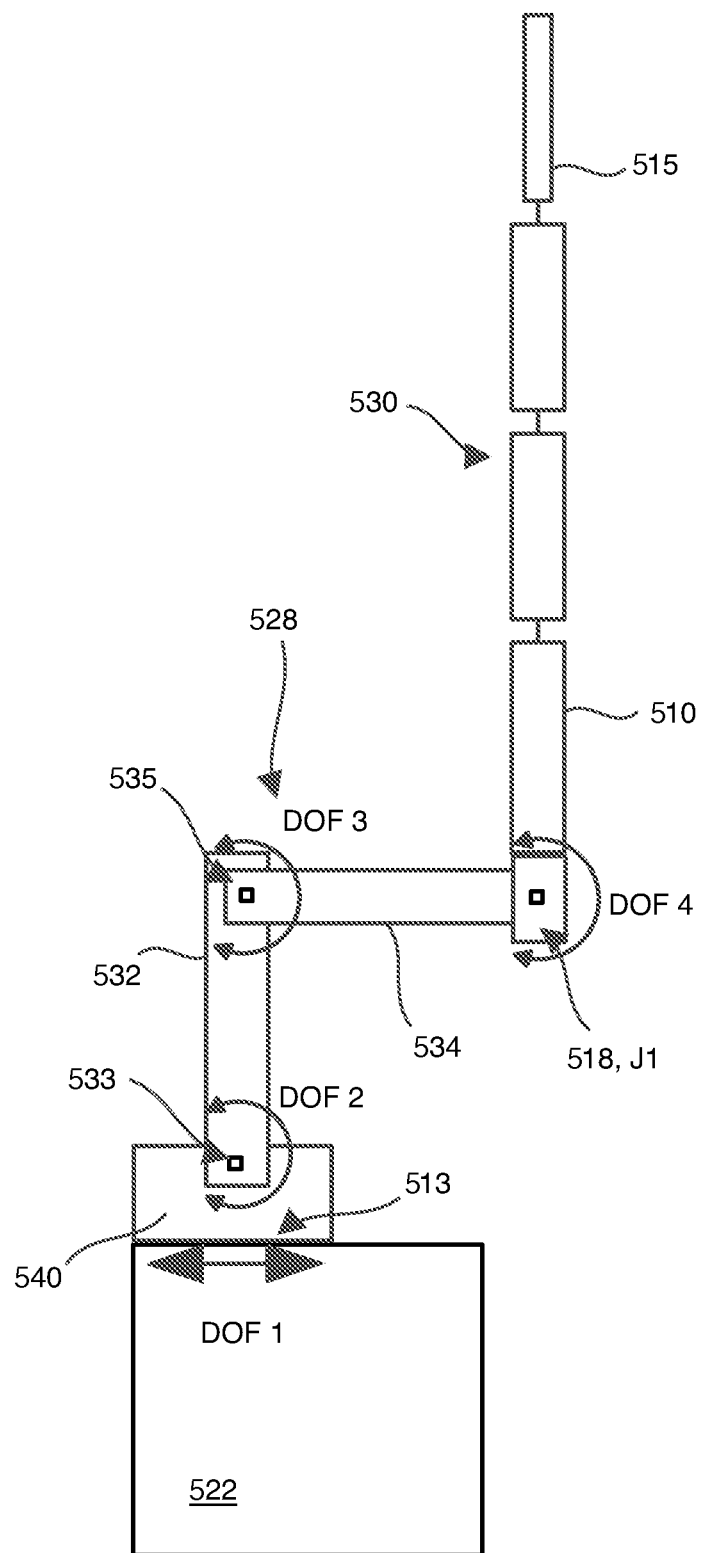
FIG. 13 is a schematic illustration of a top view of a portion of the surgical table, adapter and robotic arm of FIGS. 9A-11B, illustrating degrees of freedom associated with the joints of the adapter.

FIG. 13 is a top view of a portion of support 522, adapter 528 and a robotic arm 530 illustrating example degrees of freedom associated with the joints of the adapter 528 and/or robotic arm 530. As shown in FIG. 13, and as described above, the first link member 532 can be coupled to the interface mechanism 540 at a joint 533 and the second link member 534 can be coupled to the first link member 532 at a joint 535. The robotic arm 530 can be coupled to the second link member 534 at a coupling joint 518 and each of the links 510 of the robotic arm 530 can be coupled to each other at a joint. As shown in this example, the J1 joint of the robotic arm 530 coincides with the coupling joint 518. In some embodiments, the adapter 528, and more particularly, the interface mechanism 540 can be movably coupled to the surgical table (e.g., to the support 522) at a coupling joint 513 such that a first degree of freedom DOF 1 is provided at the coupling joint 513. In the example of FIG. 13, the coupling joint 513 provides for linear movement between the interface mechanism 540 and the surgical table, i.e. translation parallel to the X axis. In other embodiments, the coupling joint can provide pivotal or rotational movement of the interface mechanism 540 relative to the surgical table. In other embodiments, the interface mechanism 540 is fixedly coupled to the surgical table, and thus, does not move relative to the surgical table.

As also shown in FIG. 13, a second degree of freedom DOF 2 is provided at the joint 533 between the first link member 532 and the interface mechanism, and a third degree of freedom DOF 3 is provided at the joint 535 between the first link member 532 and the second link member 534. A fourth degree of freedom DOF 4 is provided at the joint 518, J1 between the second link member 534 and a link 510 of the robotic arm 530. In this example, each of DOF 2, DOF 3, and DOF 4 are shown as rotation about the Z axis.

The robotic arm 530 or a portion thereof can be releasably coupled to the adapter 528 and/or portions (e.g., links) of the robotic arm 530 can be incorporated into the adapter 528. Thus, the connection between the surgical table and the distal end of the robotic arm 530 can be conceptualized and implemented as a series of links and joints that provide the desired degrees of freedom for movement of the medical instrument 515 at the distal end of the connection. The connection may include a releasable coupling at any one or more link(s) or joint(s) or any location along the series of links and joints.

The various degrees of freedom of the links of the adapter 528 and/or robotic arm 530 provide for movement of the robotic arm 530 and therefore, a medical instrument 515 disposed at a distal end thereof to be moved to a variety of different positions and orientations relative to the table top 520 to perform various different procedures on a patient disposed thereon. The adapters 528 described herein can also provide for variations on the number of robotic arms 530 that are coupled to the table to use for a particular procedure, and to position robotic arms 530 on one or both sides of the table top 520. For example, in some procedures, it may be desirable to position two robotic arms 530 on one side of the table top 520 and two robotic arms 530 on an opposite side of the table top 520. In other procedures, it may be desirable to position three robotic arms 530 on one side of the table top 520 and one robotic arm 530 on an opposite side of the table top 520. Although many of the embodiments described herein describe the use of four robotic arms 530, it should be understood that the number of robotic arms 530 to be used for a particular surgery can vary and more or less than four robotic arms 530 can be used. Various specific example embodiments are described herein demonstrating the movement and location of the robotic arms relative to the table top 520 within a treatment area or treatment "cloud" for various different procedures.

To secure the table adapter 528 at various locations used during pre-operative setup and/or during surgery, the various joints and/or coupling locations may utilize braking or locking mechanisms. For example, braking mechanisms may provide the ability to hold position at any point in the range of motion of the joint. Braking mechanisms may include, for example, disc-caliper-style, drum-roller-style, or other friction-based mechanisms. Locking mechanisms may provide the ability to hold position at any number of discrete positions, but may not allow for continuous adjustment. Locking mechanisms can include, for example, disengaging-toothed, disengaging-pinned, or ball-detent, or other discrete position style locking mechanisms. In some embodiments, braking or locking mechanisms can prevent motion in an unpowered state and be biased towards a stopped or locked position via a spring or other mechanism. In some embodiments, in a powered state, braking or locking mechanisms may optionally release or engage depending on the desired state of the system.

Figure 14:
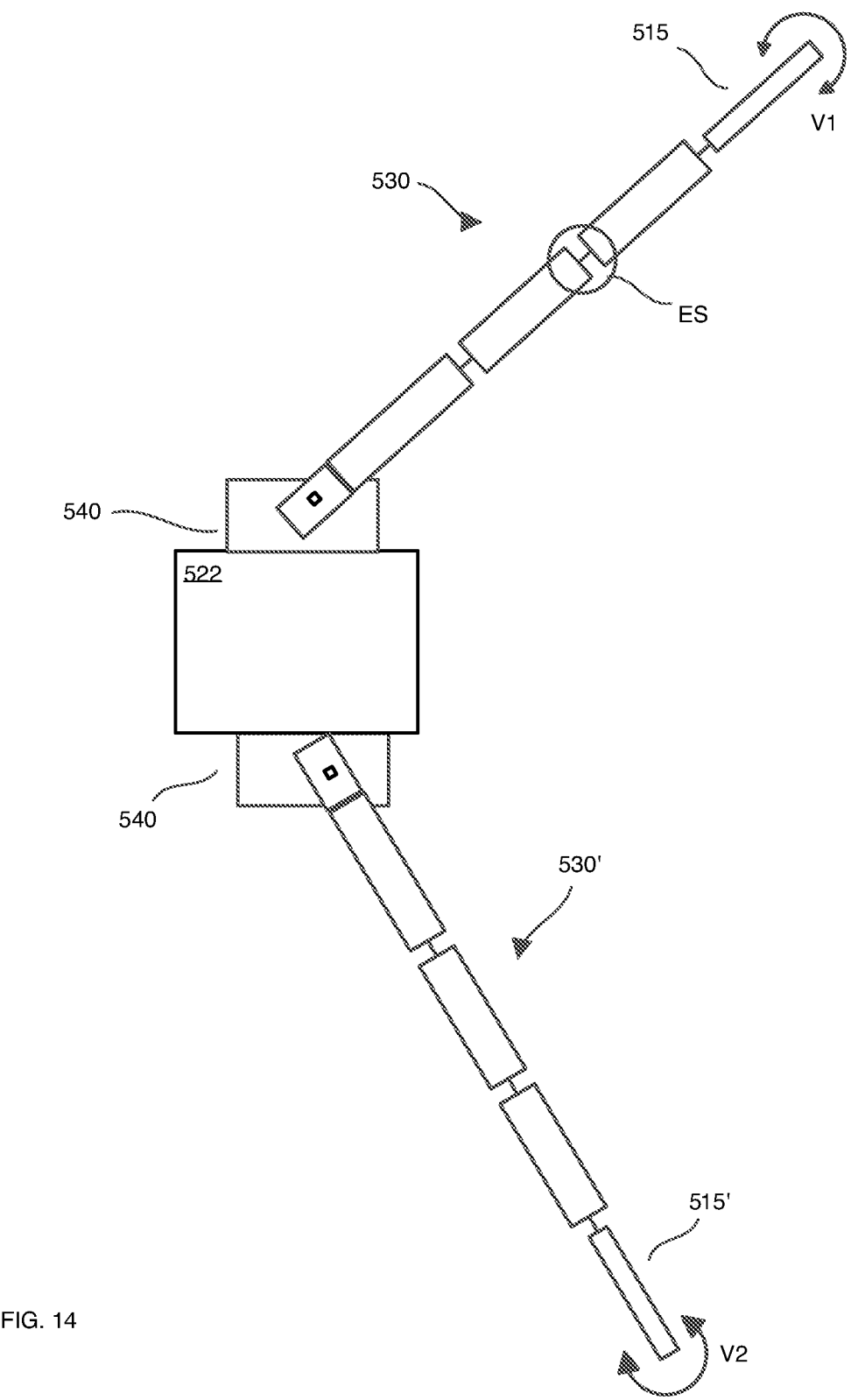
FIG. 14 is a schematic illustration of a top view of a portion of the surgical table, adapter and robotic arm of FIGS. 9A-11B, illustrating induced unwanted vibrational transmissions.

As shown schematically in FIG. 14, an energy source ES, such as motor at a joint between two links in active arm 530, in use, can induce unwanted vibration V1 in tool 515 of active arm 530, and/or vibration V2 in tool 515' of passive arm 530' via interface structure(s) 540 and column 522. For example, energy introduced by the energy source ES in the active arm 530 may propagate through the active arm 530, through the interface structure(s) 540 and column 522, and through the passive arm 530' to the tool 515' of the passive arm 530', inducing vibration V2 in tool 515'. It is desirable to reduce such vibrational cross-talk from energy source ES of active arm 530 to tool 515 of active arm 530 and to tool 515 of passive arm 530' to enhance positional accuracy of the tool 515 of active arm 530 and tool 515' of passive arm. In some instances, various components along/about each of three axes of the system may be subject to varying vibrations. In such instances, it is desirable to reduce amplitude of at least the most critical components, if not all of the components, to enhance positional accuracy of the distal ends of the robotic arms and the devices attached thereto.

FIGS. 15A-23B illustrate various embodiments of apparatus and methods for reducing vibrational cross-talk by separating the modal frequencies of vibration of the robotic arm and the table structure(s) to which the arms are coupled.

Decoupling the modal vibration frequencies of the arms (or their constituent components) from the table reduces the efficiency of transmission of the energy introduced into the active arm by, for example the motor and/or brake. For example, if an active robotic arm has a mode of 4 Hertz (Hz), energy introduced into the active robotic arm is best transferred to a passive robotic arm when the intervening structure to which the two arms are mounted has a mode equal to the mode of the active robotic arm; in this case, a mode of 4 Hz. Transmission of the energy introduced into the active robotic arm can be lessened and/or interrupted by arranging the intervening structure to have a mode different than the mode of the active robotic arm; in this case, for example, the intervening structure can be arranged to have a mode of about 6 Hz, thereby creating modal separation between the active arm and the intervening structure, and thus reducing the efficiency of energy transmission to the passive arm. Less energy transmitted between arms results in less vibration produced, i.e. lower amplitude in/about one or more axes.

Conventional surgical tables have a lowest modal frequency of about 6-8 Hz. Robotic surgical arms may have lowest modal frequencies on the order of about 4-6 Hz. To produce desired magnitude of decoupling, it is desirable to separate table frequency from arm frequency by at least about 2 Hz. In some instances, it is preferable to have a table frequency that is about two times or more than arm frequency. In disclosed embodiments, it is preferable for table frequency to be 10 Hz or more, or in some instances more preferably 12 Hz or more.

Several approaches to increasing the lowest modal frequency of the table are disclosed. As described briefly above, the table can include several components or subassemblies, including a base, adjustable column, and table top with one or more relatively moveable components. The lowest modal frequency for the overall system is typically defined by relative movement between the components or subassemblies of the surgical table, along or about different axes produced by bending, compression, or torsion of the structural components coupling the subassemblies.

Another source of undesirable lower modal frequencies is backlash, slop or play in the system, between the subassemblies or components, or between the system and the environment. For example, as discussed in Appendix A, if the base of the table is relatively stiff, resistant to bending and/or compression, it is less able to accommodate irregularities in the floor or other surface on which the base is supported. This can produce rocking or other movement of the table, which can lower one or more of the modal frequencies of movement of the system.

Figure 15A:
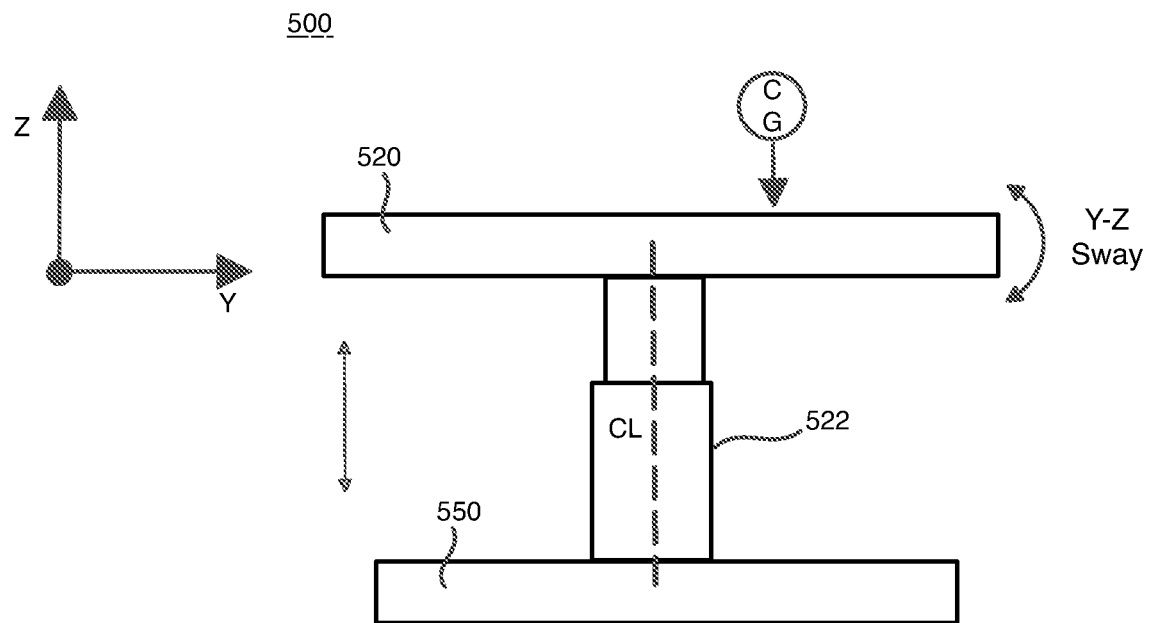
FIGS. 15A and 15B are schematic side and front views, respectively, of the surgical table of FIGS. 9A-11B, illustrating undesirable sway of the table top relative to the base.
Figure 15B:
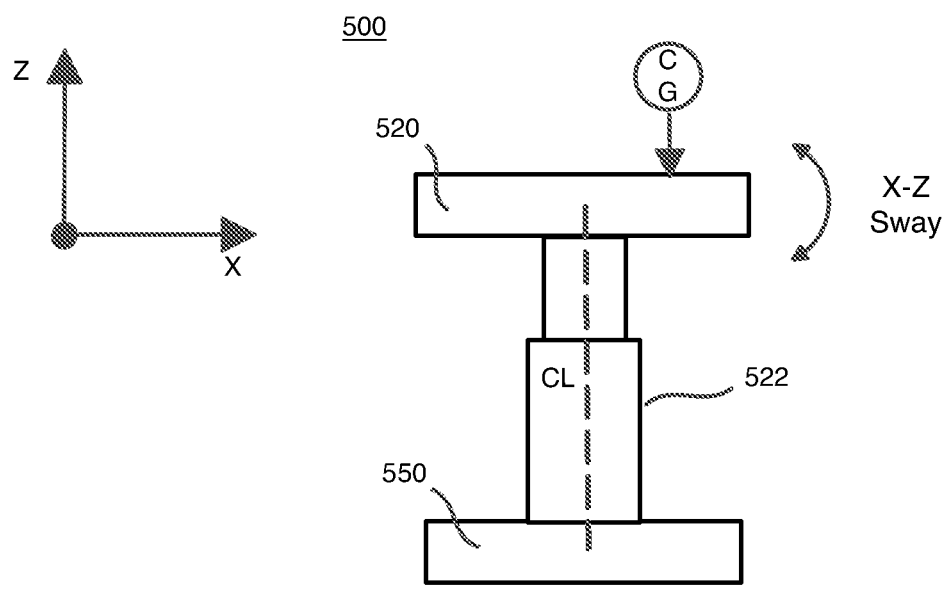

The lowest frequencies for the system may be defined by bending of the support column and/or base, and corresponding sway of the table top relative to the base. This bending and resulting sway may be in the Y-Z plane (i.e. about the X axis), as shown in FIG. 15A. It may result from the center of gravity (CG) of the load carried by the column 522 (i.e. the table top, the robotic arms, the patient, and any other equipment mounted to the table top or support column) being displaced longitudinally (along the Y axis) from the center line CL of the column, as shown in FIG. 15A. The bending/sway may also be in the X-Z plane (i.e. about the Y axis), as shown in FIG. 15B. This may result from the CG of the load being displaced longitudinally (along the X axis) from the center of the column, as shown in FIG. 15B. The CG may be displaced from the CL by positioning of the robotic arms and/or the patient for the surgical procedure.

Figure 16A:
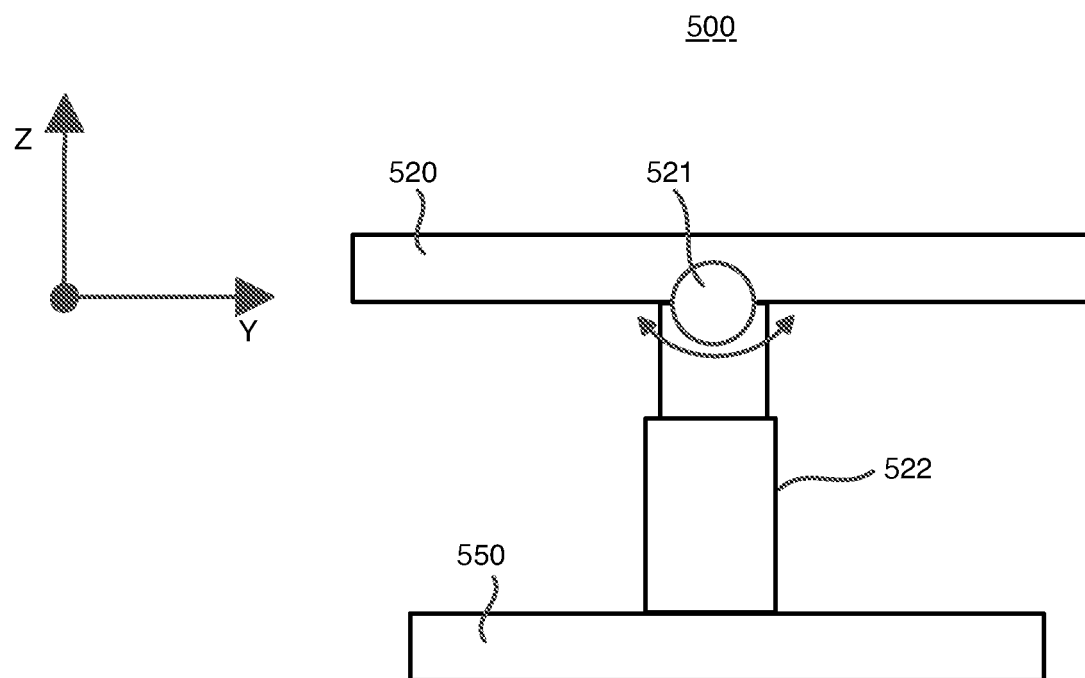
FIGS. 16A and 16B are schematic side and front views, respectively, of the surgical table of FIGS. 9A-11B, illustrating pivotal movement of the table top relative to the base.
Figure 16B:
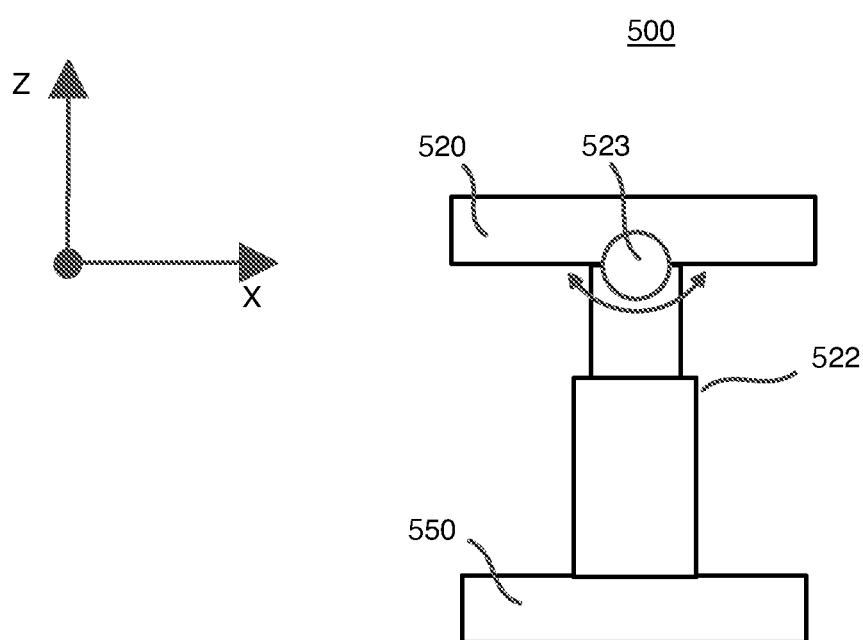

As discussed above, the table top may also be pivotable relative to the column to position the table top and patient in a desired orientation for a given surgical procedure. As shown in FIG. 16A, this pivotal movement may be about the X axis, i.e. about a pivot 521. As shown in FIG. 16B, this pivotal movement may be about the Y axis, i.e. about a pivot 523. Either pivotal movement may also produce a displacement of the CG relative to the CL of the column. The mechanism that enables and produces either or both pivotal movements may also be a source of backlash, which, as noted above, can lower the modal frequency of one or more of the degrees of movement of the table. Described below are several embodiments of mechanisms that can enable and/or produce pivotal movement of the table top but have relatively high structural rigidity, minimize tendency to bend the column, otherwise resist sway of the table top relative to the base, and/or reduce sources of backlash in the system.

To allow the table top to pivot relative to the column (e.g., along and/or about the Z, Y, and/or Z axis) to position the table top and patient in a desired orientation (e.g., a Trendelenburg orientation) for a given surgical procedure, a surgical table can include a pivot assembly coupled to its telescopic column and having actuators operably coupled to various portions of the table top and arranged to move the table top into the desired orientation. For example, as shown schematically in FIGS. 17A-17C, such a surgical table 600 includes a table top 620, a table support or column 622, a table base 650, and a pivot assembly 660. The table top 620 is disposed on the column 622, which can be, for example, a pedestal, at a suitable height above the floor. The column 622 includes two sections that telescope relative to each other to provide translation in the Z axis (height above the floor), as illustrated schematically in FIGS. 17A and 17C. The surgical table 600 can be the same as or similar in structure and function to the surgical table 500 described herein. Thus, some details regarding the surgical table 600 are not described below. It should be understood that for features and functions not specifically discussed, those features and functions can be the same as or similar to any of the surgical tables described herein.

As discussed in further detail herein, in this embodiment, the pivot assembly 660 is coupled to the column 622. In this manner, the column 622 and the pivot assembly 660 can translate simultaneously in the Z axis (height above the floor). The pivot assembly 660 includes a primary load support 662, a first actuator 663A, a second actuator 663B, a third actuator 663C, and a support flange 661 arranged to support the pivot assembly 660 and to couple the pivot assembly 660 with the column 622, as illustrated schematically in FIGS. 17A-17C.

The primary load support 662 includes a pivot 664 operably coupled to the table top 620. Similarly as described with respect to pivot 121 and pivot 123, the pivot 664 allows for pivotal movement of the table top 620 relative to the column 622 about the X axis and about the Y axis to position the table top 622 and patient (not shown) in a desired orientation for a given surgical procedure. Pivot 664 may be implemented with a gimbal joint arrangement to enable the two-axis pivoting motion.

Figure 17A:
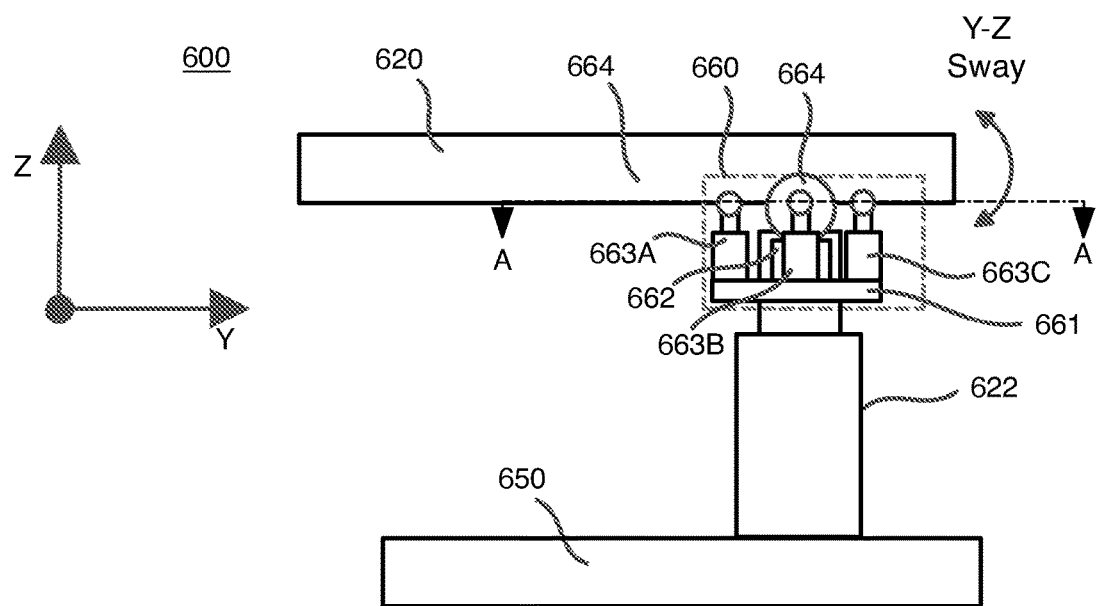
FIGS. 17A-17C are schematic side, cross-sectional top, and front views, respectively, of a surgical table having a pivot assembly coupled about a column, according to an embodiment.
Figure 17B:
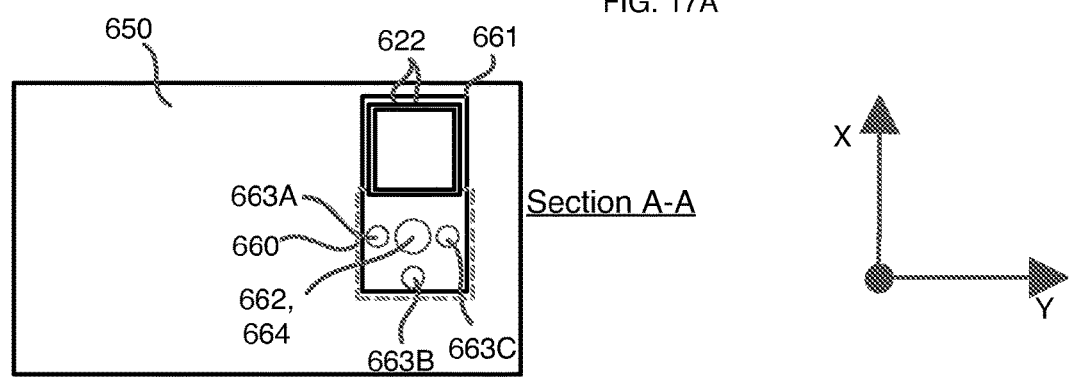
Figure 17C:
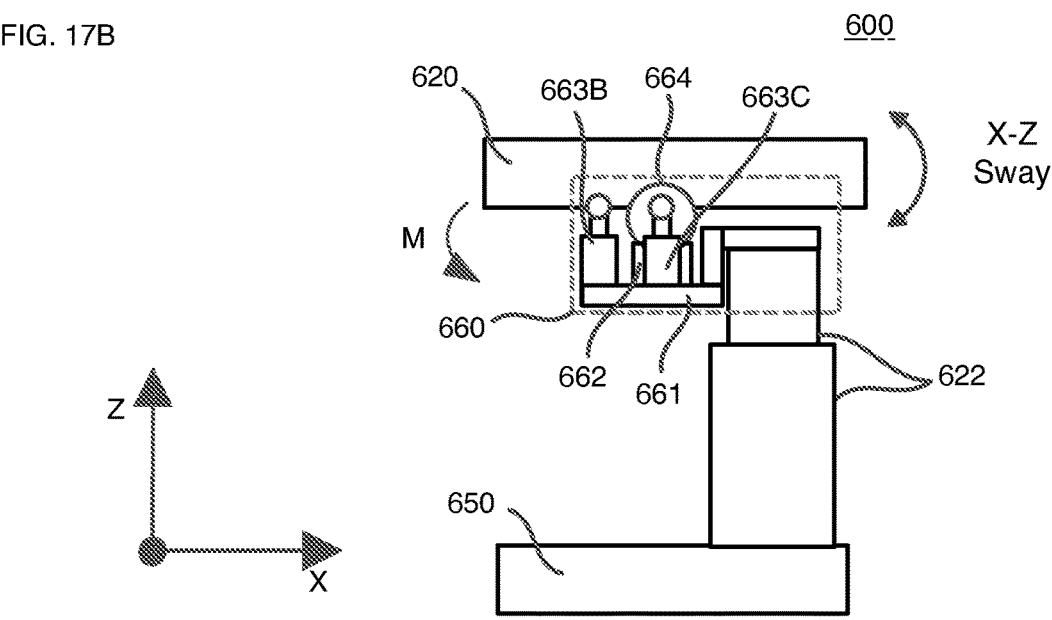

As illustrated in FIGS. 17A-17C, the pivot assembly 660 is coupled to the column 622 in a cantilevered fashion. In this embodiment, the column 622 is located off the origin of the X and Y axis of the base 650, with the primary load support 662 disposed near the centerline of the table top 620. In this arrangement, the cantilevered pivot assembly 660 and the table load can collectively cause an undesirable bending moment M (see e.g., FIG. 17C) and shear force on the column 622. The bending moment M and shear force on the column 622 can cause wear due to undesirable contact or rubbing between the two sections of the column 622 (e.g., between telescoping joints) during their relative movement. Over time, the wear can result in lowered structural rigidity, increased sway of the table top 620, and/or increased backlash in the system. Further, the cantilevered position of the pivot assembly 660 relative to the column 622 may lead to the center of gravity being displaced beyond an acceptable boundary defined by the base 650 (e.g., beyond an acceptable distance from the center line of the column 622), for example if the patient is disposed more to the opposite side of the table top 620, and/or robotic arms are extended on the opposite side of the table top 620.

Figure 18A:
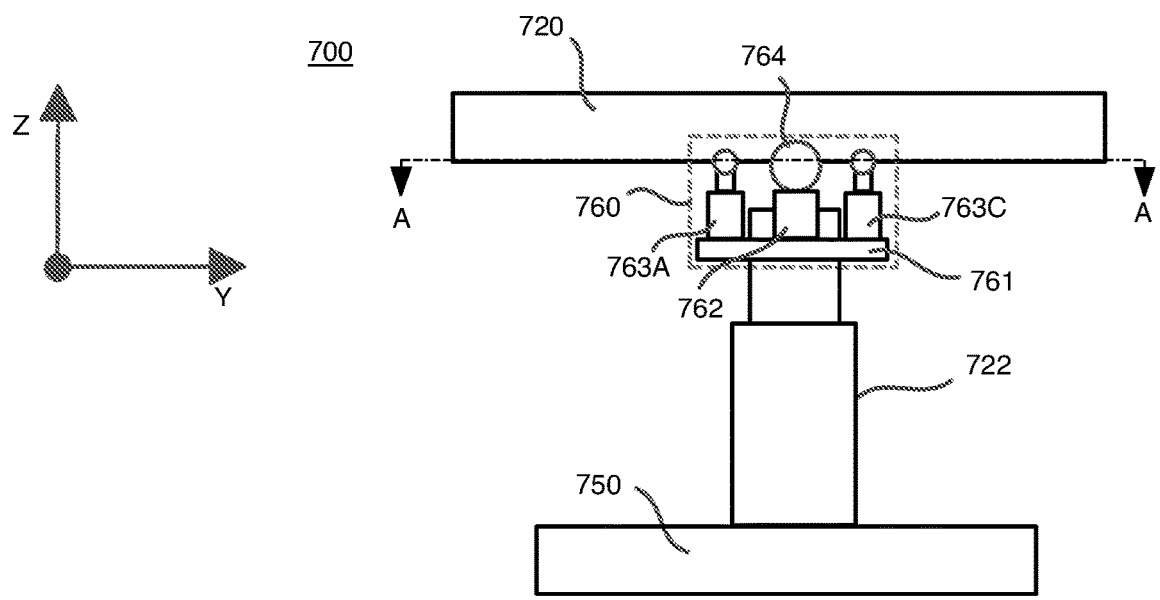
FIGS. 18A-18C are schematic side, cross-sectional top, and front views, respectively, of a surgical table having a pivot assembly coupled about a column, according to an embodiment.
Figure 18B:
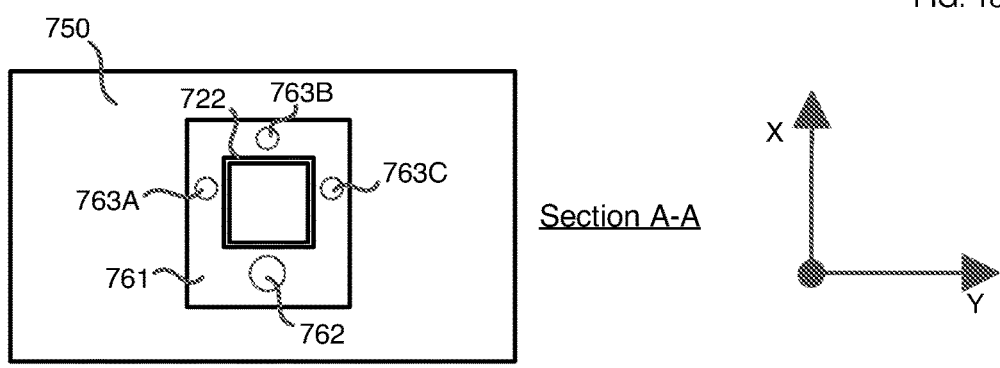
Figure 18C:
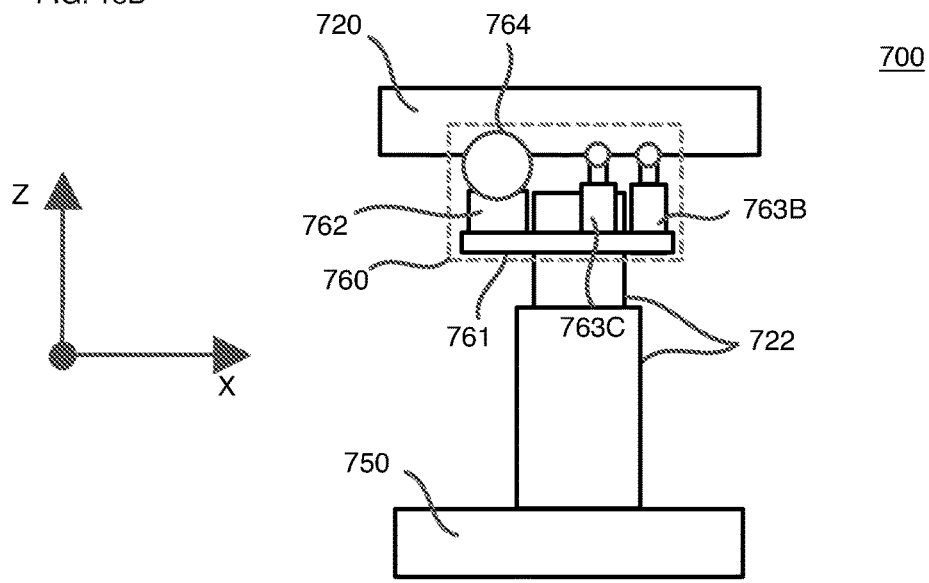

To enable and/or produce pivotal movement of a table top but remedy the deficiencies illustrated and described with respect to the embodiment shown in FIGS. 17A-17C, rather than coupling the pivot assembly with the column in a cantilevered fashion, the pivot assembly can be arranged about the column, and the column can be relocated towards the center of the base (rather than off-center as shown an described with respect to the embodiment shown in FIGS. 17A-17C). In this manner, the location of the center of gravity is improved by moving it towards the central vertical axis of the column). FIGS. 18A-18C illustrate a surgical table 700 according to such an embodiment. As shown, in this embodiment, the surgical table 700 includes a table top 720, a table base 750, a table support or column 722 located at or near the center of the table base 750, and a pivot assembly 760 distributed about the column 722. The table top 720 is disposed on the column 722, which can be, for example, a pedestal, at a suitable height above the floor. The column 722 includes two sections that telescope relative to each other to provide translation in the Z axis (height above the floor), as illustrated schematically in FIGS. 18A and 18C. The surgical table 700 can be the same as or similar in structure and function to any of the surgical tables (e.g., surgical table 500, 600, etc.) described herein. Thus, some details regarding the surgical table 700 are not described below. It should be understood that for features and functions not specifically discussed, those features and functions can be the same as or similar to any of the surgical tables described herein.

The pivot assembly 760 includes a primary load support 762, a first actuator 763A, a second actuator 763B, a third actuator 763C, and a support flange 761 arranged to support the pivot assembly 760 and to couple the pivot assembly 260 with the column 722, as illustrated schematically in FIGS. 18A-18C. The actuators 763A, 763B, 763C and the primary load support 762 are spaced about various sides or portions of the column 722, as best illustrated schematically in top view in FIG. 18B (section A-A of FIG. 18A). More specifically, the primary load support 762 is connected at its lower end to the support flange 761 at a first portion of the support flange 761 on one side of the column 722. The primary load support 762 includes a pivot 764 (e.g. a gimbal joint) operably coupled to the lower side of the table top 720. In turn, the second actuator 763B is connected at its lower end to another portion of the support flange, on the side of the column 722 opposite to the portion of the support flange 761 to which the lower end of the primary load support 762 is connected. Further, the first actuator 763A is connected at its lower end to the support flange 761 at a third portion of the support flange on the side of the column 722 between the first and second portions of the support flange 761, i.e. between the primary load support 762 and the second actuator 763B, and the third actuator 763C is connected at its lower end to the support flange 761 at a fourth portion of the support flange on the opposite side of the column 722 from the first actuator 763A, and between the first and second portions of the support flange 761, i.e. between the primary load support 762 and the second actuator 763B. Each of the actuators 763A, 763B, and 763C is coupled at its upper end (e.g., with a gimbal joint) to the lower side of the table top 320.

Distributing the pivot assembly 760 about the column 722 in this manner allows the center of gravity (CG) of the load carried by the column 722 (i.e. the table top, the robotic arms, the patient, and any other equipment mounted to the table top or support column) to be placed at or near the center of the column 722, thereby limiting or reducing uneven loading at the telescoping column 722, improving stiffness and stability of the system, and increasing modal frequency of the table top 720 and the column 722. In this embodiment, the center of gravity, and the center of the column 722 is also be placed at or near the origin of the base's 750 X axis and Y axis.

Figure 18D:
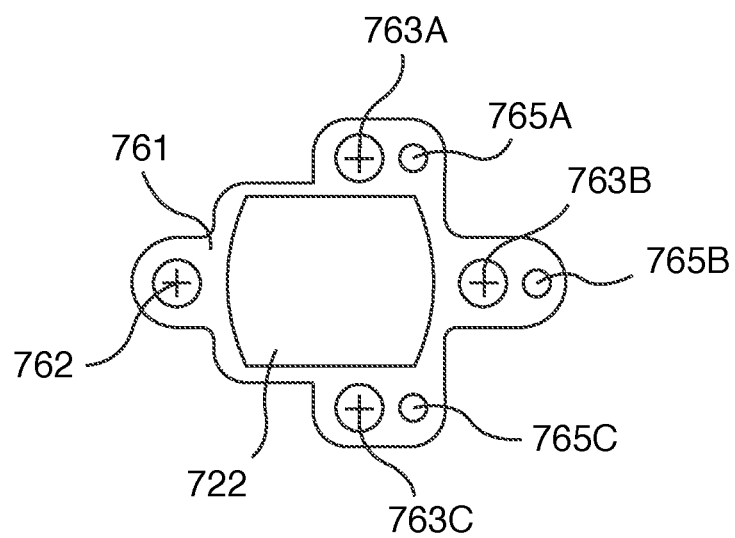
FIG. 18D is a cross-sectional top view of an alternative configuration of the pivot assembly of FIGS. 18A-18C.

An alternative configuration of pivot assembly 760 is shown in FIG. 18D. In this configuration, the portions of the support flange 761 to which the lower ends of the primary load support 762 and the actuators 763A, 763B, and 763C are attached are configured as discrete lateral projections from the body of the support flange 761. FIG. 18D also illustrates a possible arrangement of drive motors 765A, 765B and 765C for the respective actuators 763A, 763B and 763C.

In another embodiment, a surgical table can be the same as or similar in structure and function to the surgical table 500, the surgical table 600, and/or the surgical table 700 described herein, except the primary load support can be relocated to the top end of the column, with the actuators distributed about the primary load support. FIGS. 19A-19D illustrate a surgical table 800 according to such an embodiment. As shown, in this embodiment, the surgical table 800 includes a table top 820, a table base 850, a table support or column 822 located at or near the center of the table base 850, and a pivot assembly 860 disposed on top of the column 822. The table top 820 is disposed on the pivot assembly 860. The column 822 can be, for example, a pedestal. The column 822 includes two sections that telescope relative to each other to provide translation in the Z axis (height above the floor), as illustrated schematically in FIGS. 19A and 19C.

As shown, the pivot assembly 860 is disposed on top of and coupled to the top of the column 822 and the bottom of the table top 820. In this manner, the column 822 and the pivot assembly 860 can translate simultaneously in the Z axis (height above the floor), and the table top 820 can be disposed at a suitable height above the floor. The pivot assembly 860 includes a primary load support 862, a first actuator 863A, a second actuator 863B, a third actuator 863C, and a support flange 861 arranged to support the pivot assembly 860 and to couple the pivot assembly 860 with the column 822, as illustrated schematically in FIGS. 19A-19C.

In this embodiment, the primary load support 862 is disposed on top of the column 822. More specifically, the lower end of the primary load support 862 is disposed within the periphery of the support column 822 in a plane transverse to the vertical axis (Z axis) of the column 822, i.e. in the X-Y plane. The upper end of primary load support 862 includes a pivot 864 (e.g. a gimbal joint) operably coupled to the lower side of the table top 820. Disposing the primary load support 862 on top of the column 822 in this manner allows the center of gravity (CG) of the load carried by the column 322 (i.e. the table top, the robotic arms, the patient, and any other equipment mounted to the table top or support column) to be placed at or near the center of the column 822, thereby limiting or reducing uneven loading at the telescoping column 822, improving stiffness and stability of the system, and increasing modal frequency of the table top 820 and the column 822. In this embodiment, the center of gravity, and the center of the column 822 is also placed at or near the origin of the base's 850 X axis and Y axis. Further, disposing the primary load support 863 on top of the column 822 and distributing the actuators 863A, 863B, 863C about the primary load support 863 reduces and/or eliminates the undesirable bending moment and shear force described above with respect to FIGS. 17A-17C, thereby limiting or reducing uneven loading at the telescoping column 822, improving stiffness and stability of the system, and increasing modal frequency of the table top 820 and the column 822.

Disposing the entire pivot assembly 860 on top of column 822, i.e. with all components including the actuators 863A, 863B, and 863C above the top of the column, increases the height of the table top 820, which can aggravate the bending forces on the column 822 and lower modal frequency(ies) associated with the column bending. An alternative arrangement is shown in FIG. 19D. In this arrangement support flange 861 includes an upper portion 861A coupled to the top of support column 822, a lower peripheral portion 861B, and a side portion 861C connecting the lower peripheral portion 861B to the upper portion 861A. The lower end of primary load support 862 is coupled to the upper portion 861A of support flange 861, and the lower ends of the actuators 863A, 863B, and 863C are coupled to the lower peripheral portion 861B.

An alternative configuration of pivot assembly 860 is shown in FIG. 19D. In this configuration, the portions of the lower peripheral portion 861B of support flange 861 to which the lower ends of the primary load support 862 and the actuators 863A, 863B, and 863C are attached are configured as discrete lateral projections from the side portion 861C of the support flange 861. FIG. 18D also illustrates a possible arrangement of drive motors 865A, 865B and 865C for the respective actuators 863A, 863B and 863C.

Figure 20A:
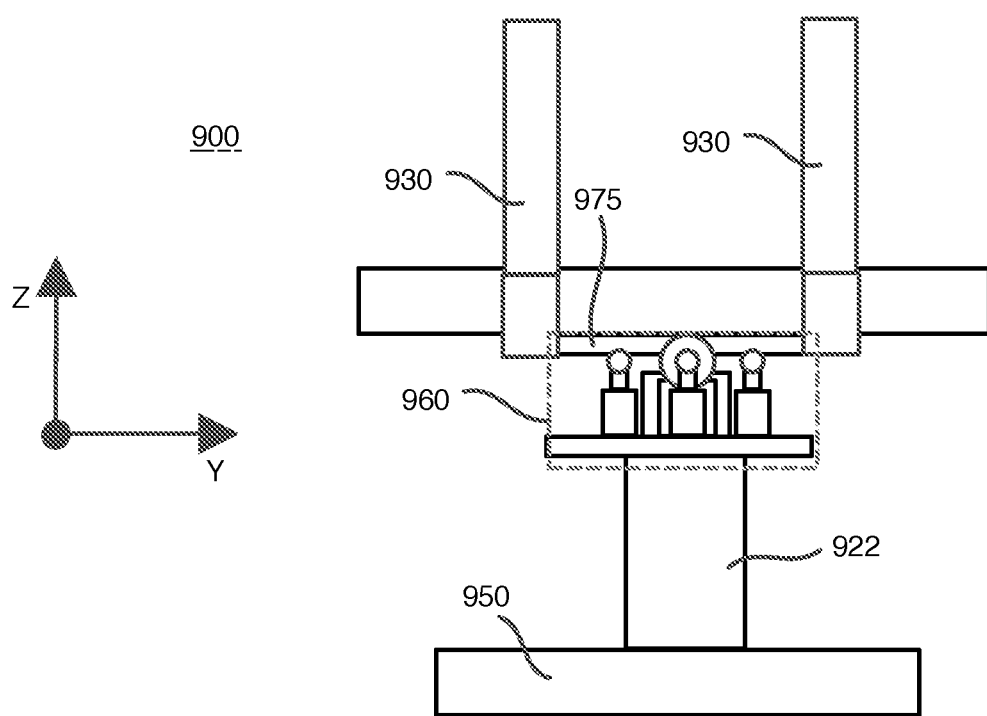
FIG. 20A is a schematic side view of a surgical table having a pivot assembly coupled to a column, robotic arms coupled to a table top adapter, and a table top in a first orientation.
Figure 20B:
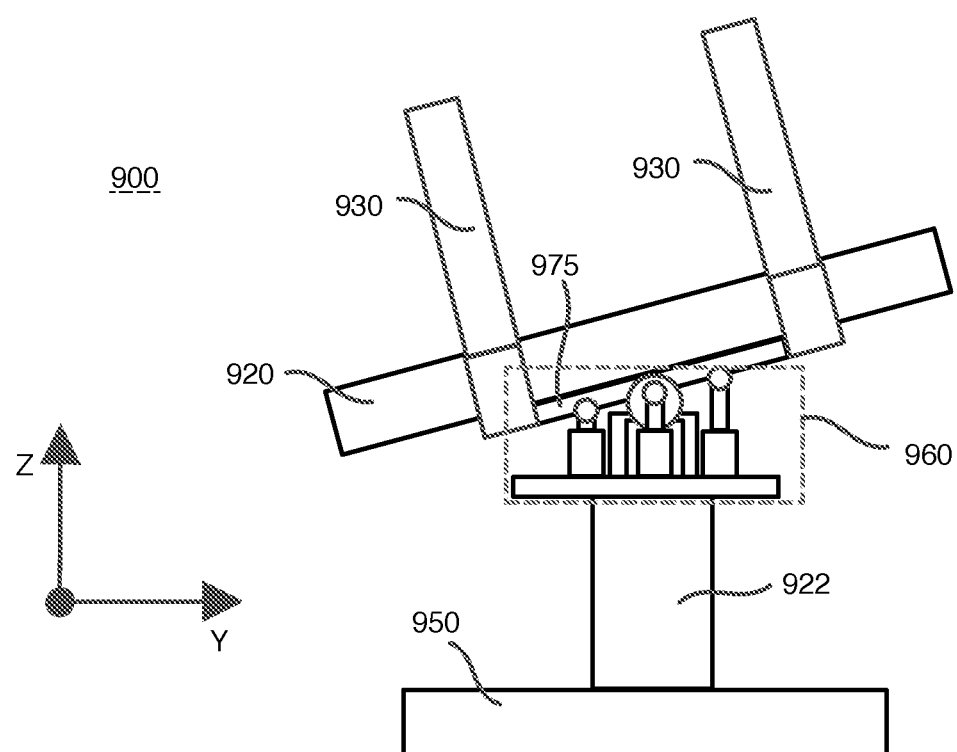
FIG. 20B is a schematic side view of the surgical table of FIG. 20A in a second orientation, according to an embodiment.

As described above with respect to FIGS. 9C and 9D, one or more robotic arms can be coupled to the table to reach a desired treatment target on a patient disposed on the table top. In a robotically assisted surgical procedure, the robotic arm(s) can be disposed in a, desired operative position relative to a patient disposed on the table top of the surgical table. In some embodiments, a table top can be coupled to the column via, a table top adapter coupling, FIGS. 20A and 20B illustrate such an embodiment. In this embodiment, the surgical table 900 can be the same as or similar in structure and function to any of the surgical tables described herein. Thus, some details regarding the surgical table 900 are not described below. It should be understood that for features and functions not specifically discussed, those features and functions can be the same as or similar to any of the surgical tables described herein.

In this embodiment, the surgical table 900 includes a table top 920, a table support or column 922, a table base 950, a pivot assembly 960, a table top adapter coupling 975 (also referred to herein as "table top adapter") disposed between and arranged to couple the column 922 and the table top 920, and two robotic arms 930 coupled to the table top adapter coupling 975. The pivot assembly 960 is operably coupled to the table top adapter 975 and can enable pivoting (as discussed with respect to previous embodiments) of the table top adapter 975 and in turn the table top 920 to place the table top 920 in a desirable position and orientation for a given procedure.

In this embodiment, the robotic arms 930 are coupled to and extend from the table top adapter 975. Coupling the robotic arms 930 to the table top adapter 975 in this manner, however, may have some drawbacks. For example, in such an embodiment, tilt of the table top 920 and/or its constituent sections will cause movement or tilt of the robotic arms 930 because the robotic arms 930 are coupled to the table top 920 via the table top adapter 975, as illustrated schematically in FIG. 20B. As such, positioning of the robotic arms 930 (and any instruments attached thereto) needs to incorporate table top 920 positioning, thereby complicating the operation of the system. As another example of a potential drawback, coupling both the table top 920 and the robotic arms 930 to the table top adapter 975 may result in the table top 920 and the robotic arms 930 having too similar of modal frequencies, thereby potentially increasing unwanted vibration at the working ends, as described in more detail herein.

Such drawbacks can be addressed, for example, by coupling the robotic arms to a more rigid structure of the surgical table and to a structure independent from tilting motions of the table top and/or its constituent sections. Such an embodiment is illustrated schematically in FIGS. 21A-21E. In this embodiment, the surgical table 1000 can be the same as or similar in structure and function to any of the surgical tables described herein. Thus, some details regarding the surgical table 1000 are not described below. It should be understood that for features and functions not specifically discussed, those features and functions can be the same as or similar to any of the surgical tables described herein.

In this embodiment, the surgical table 1000 includes a table top 1020, a table base 1050, a table support or column 1022 located at or near the center of the table base 1050, a pivot assembly 1060 disposed on top of the column 1022, two robotic arms 1031, 1032, and a table top adapter coupling 1075 (also referred to herein as "table top adapter") disposed between and arranged to couple the column 1022 and the table top 1020. The table top adapter 1075 is operably coupled to the pivot assembly 1060 and the table top 1050. The column 1022 includes two sections that telescope relative to each other to provide translation in the Z axis (eight above the floor).

As shown, the pivot assembly 1060 is disposed on top of and coupled to the top of the column 1022, and is further coupled to the bottom of the table top adapter 1075. In this manner, the column 1022 and the pivot assembly 1060 can translate simultaneously in the Z axis (height above the floor), and the table top 1020 can be disposed at a suitable height above the floor. The pivot assembly 1060 includes a primary load support 1062, a first actuator 1063A, a second actuator 1063B, a third actuator 1063C, and a support flange 1061 arranged to support the pivot assembly 1060 and to couple the pivot assembly 1060 with the column 1022, as illustrated schematically in FIGS. 21A-21C.

In this embodiment, the primary load support 1062 is disposed on top of the column 1022. More specifically, the lower end of the primary load support 1062 is disposed within the periphery of the support column 1022 in a plane transverse to the vertical axis (Z axis) of the column 1022, i.e., in the X-Y plane. The upper end of the primary load support 1062 includes a pivot 1064 (e.g., a gimbal joint) operably coupled to the lower side of the table top adapter 1075. Disposing the primary load support 1062 on top of the column 1022 in this manner allows the center of gravity (CG) of the load carried by the column 1022 (i.e., the table top, the robotic arms, the patient, and any other equipment mounted to the table top or support column) to be placed at or near the center of the column 1022, thereby limiting or reducing uneven loading at the telescoping column 1022, improving stiffness and stability of the system, and increasing modal frequency of the table top 1020 and the column 1022. In this embodiment, the center of gravity (CG) and the center of the column 1022 is also placed at or near the origin of the base's 1050 X axis and Y axis. Further, disposing the primary load support 1063 on top of the column 1022 and distributing the actuators 1063A, 1063B, 1063C about the primary load support 1063 reduces and/or eliminates the undesirable bending moment and shear force described above with respect to FIGS. 17A-17C, thereby limiting or reducing uneven loading at the telescoping column 1022, improving stiffness and stability of the system, and increasing modal frequency of the table top 1020 and the column 1022.

Similarly as described with respect to the embodiment of FIG. 19D, in this embodiment, the support flange 1061 includes an upper portion 1061A coupled to the top of the support column 1022, a lower peripheral portion 1061B, and a side portion 1061C connecting the lower peripheral portion 1061B to the upper portion 1061A. The lower end of the primary load support 1062 is coupled to the upper portion 1061A of the support flange 1061, and the lower ends of the actuators 1063A, 1063B, and 1063C are coupled to the lower peripheral portion 1061B.

Figure 19A:
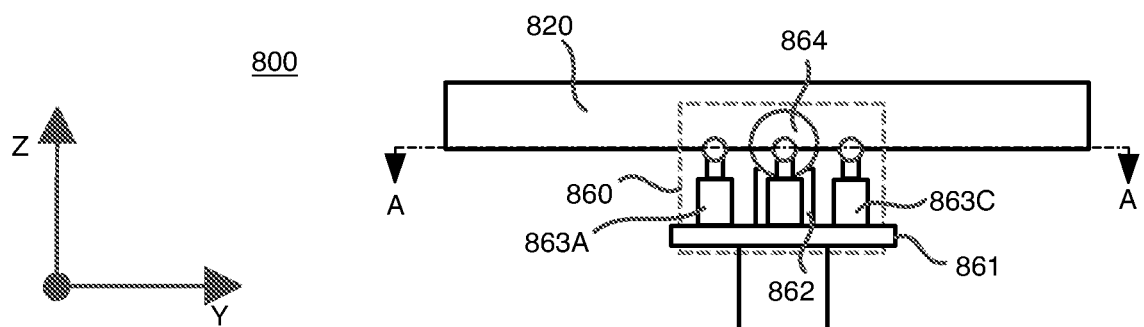
FIGS. 19A-19C are schematic side, cross-sectional top, and front views, respectively, of a surgical table having a pivot assembly coupled to a column, according to an embodiment.
Figure 19B:
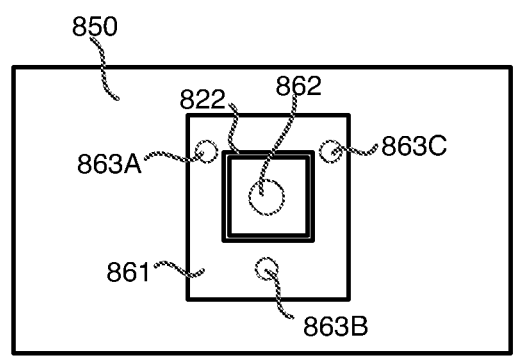
Figure 19C:
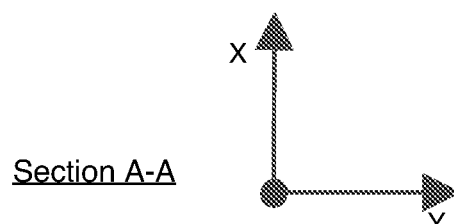
Figure 19C:
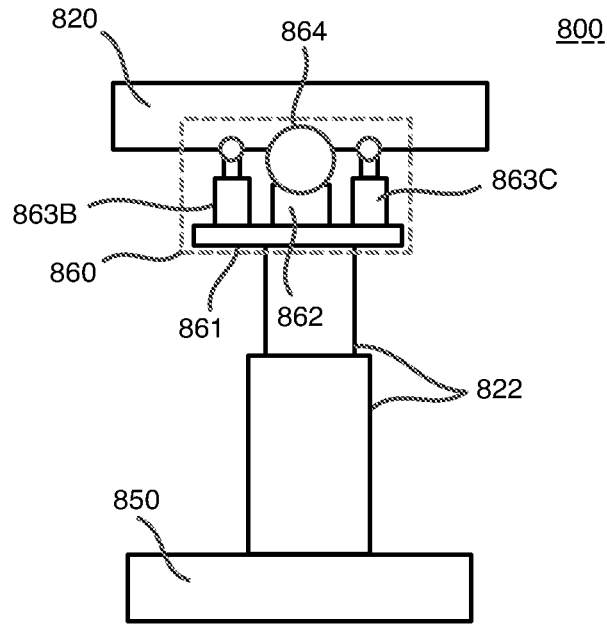
Figure 19D:
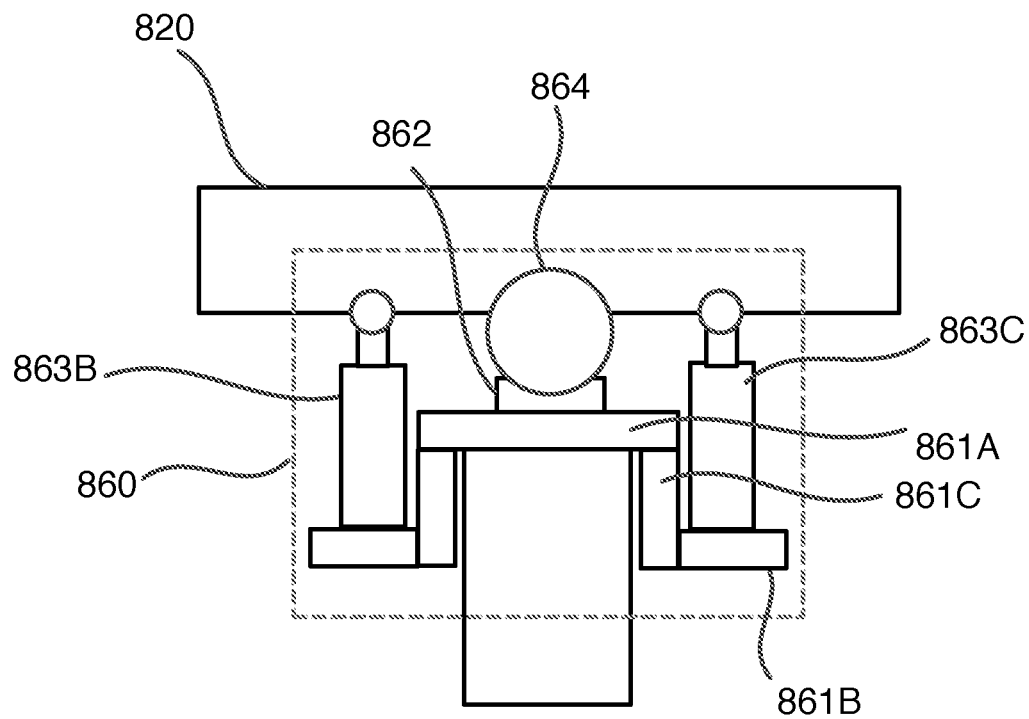
FIG. 19D is a schematic cross-sectional view of an alternative support structure for the pivot assembly of FIGS. 19A-19C.
Figure 19E:
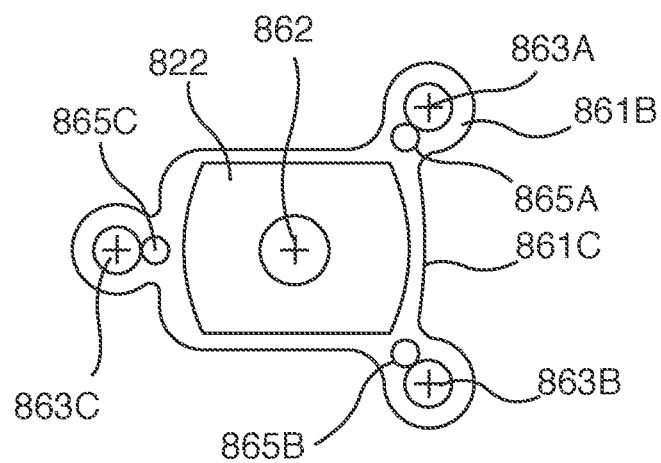
FIG. 19E is a cross-sectional top view of an alternative configuration of the pivot assembly of FIGS. 19A-19C.

In this embodiment, with the primary load support 1062 connected at its lower end to the support flange 1061, and the pivot 1064 (e.g., a gimbal joint) of the primary load support 1062 is operably coupled to the lower side of the table top adapter 1075, as described above, the actuators are distributed about the periphery of the column 1022 and the primary load support 1062 (similar to the embodiment of FIG. 19B). More specifically, the first actuator 1063 is connected at its lower end to the lower peripheral portion 1061B, on one side of the column 1022. The third actuator 1063C is connected at its lower end to another portion of the lower peripheral portion 1061B of the support flange 1061, on a side of the column 1022 opposite to the portion of the support flange 1061 to which the lower end of the first actuator 1063A is connected. Further, the second actuator 1063B is connected at its lower end to the lower peripheral portion 1061B of the support flange 1061 at a third portion of the lower peripheral portion 1061B on a side of the column 1022 between the first and second portions of the support flange 1061 along the Y axis, and such that the primary load support 862 is disposed between the first/second portions and the third portion of the support flange 1061 along the X axis. Each of the actuators 1063A, 1063B, and 1063C is coupled at its upper end (e.g., with a gimbal joint) to the lower side of the table top adapter 1075.

Further, as shown, in this embodiment, the robotic arms 1031, 1032 are coupled to the support, flange 1061 of the pivot assembly 1060 (rather than being coupled to the table top adapter or the table top). In this manner, in use, the robotic arms 1031, 1032 can translate simultaneously with the column 1022, the table top 1020, and the table top adapter 1075 in the Z axis (height above the floor), but are independent from any pivoting or tilting of the table top 1020 and table top adapter 1075. This feature is illustrated schematically in FIG. 21C in which the pivot assembly 1050 is adjusted such that the table top 1020 and the table top adapter 1075 are tilted, while the robotic arms 1031, 1032 remain in a vertical position (i.e., the same vertical position the robotic arms 1031, 1032 were in prior to the pivot assembly being adjusted, as illustrated schematically in FIG. 21A).

Figure 21A:
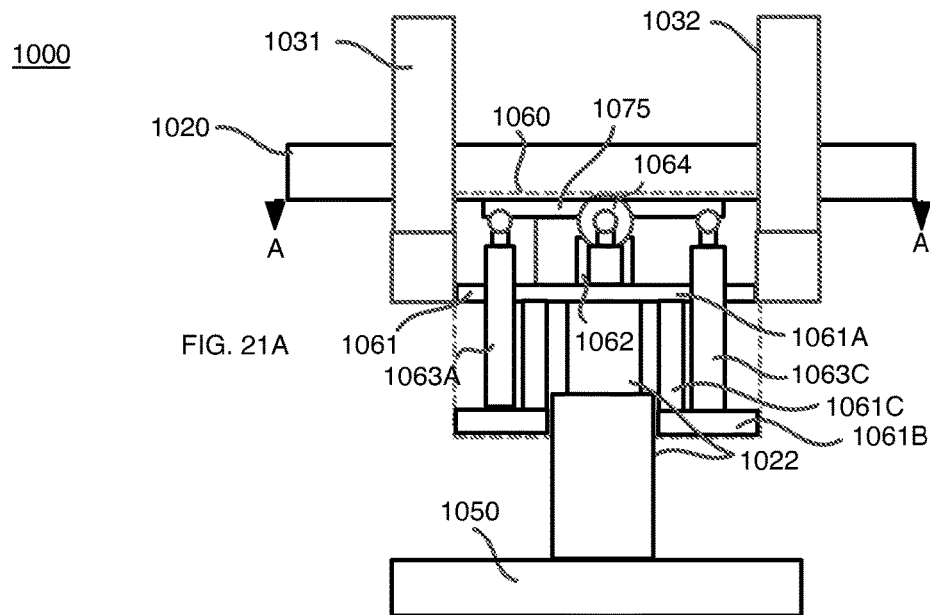
FIG. 21A is a schematic side view of a surgical table having a pivot assembly coupled to a support flange, robotic arms coupled to the support flange, a table top in a first orientation, according to an embodiment.
Figure 21B:
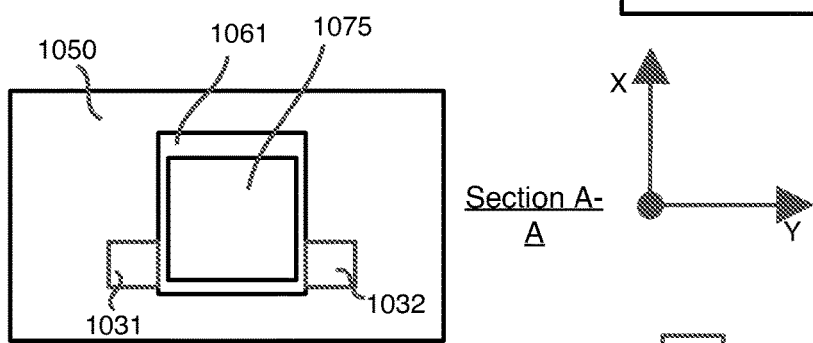
FIG. 21B is a schematic cross-sectional top view of FIG. 21A.
Figure 21C:
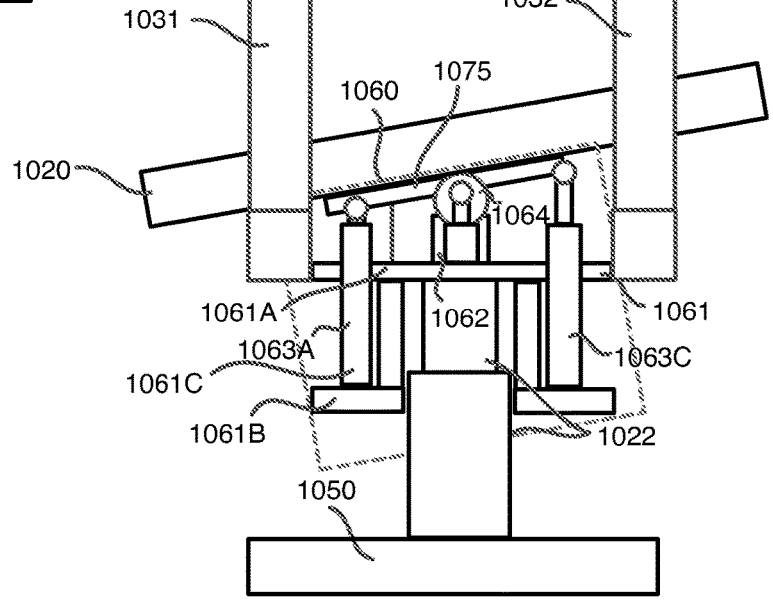
FIG. 21C is a schematic side view of the surgical table of FIG. 21A in a second orientation.
Figure 21D:
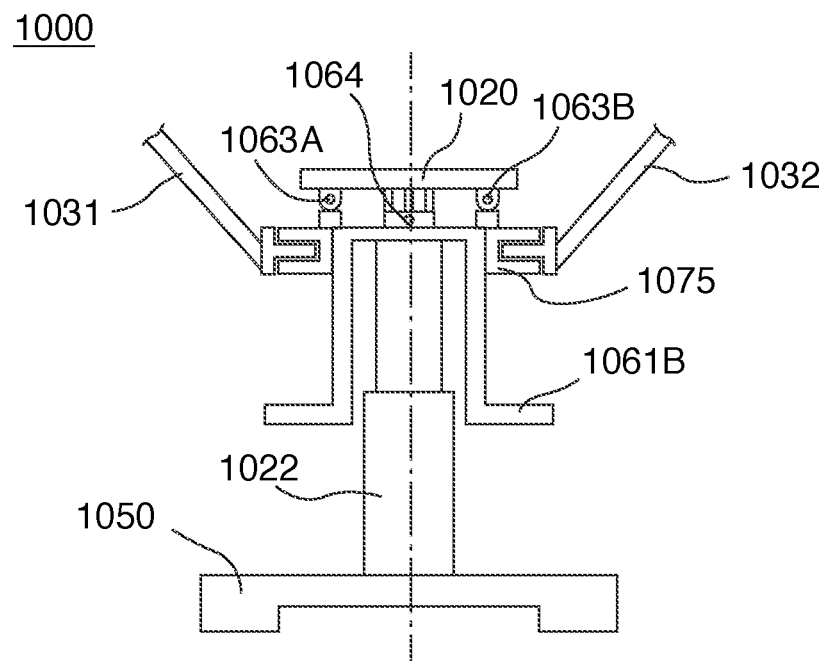
FIGS. 21D and 21E are schematic front and top views of an alternative configuration of the surgical table of FIGS. 21A-21C.
Figure 21E:
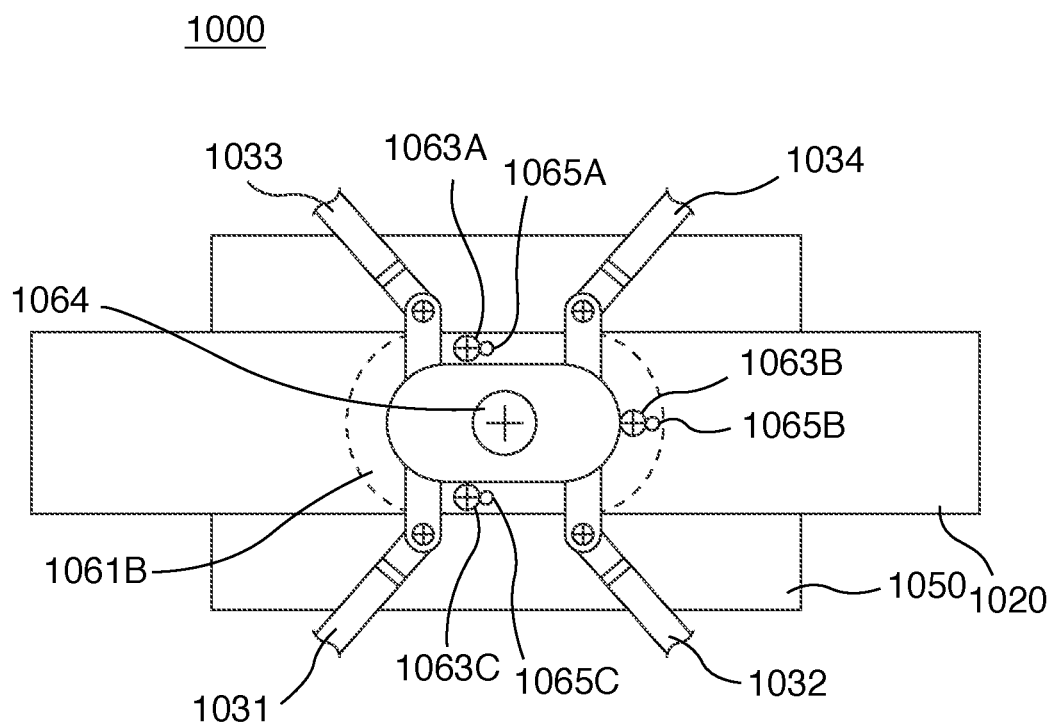

An alternative configuration of surgical table 1000 is shown in FIGS. 21D and 21E. In this configuration, four robotic arms 1031, 1032, 1033, and 1034 are shown coupled to the table top adapter 1075. FIG. 21E also illustrates a possible arrangement of drive motors 1065A, 106513 and 1065C for the respective actuators 1063A, 1063B and 1063C.

Coupling the robotic arms to the support flange 1061 in this manner increases desirable modal frequency separation and reduces crosstalk vibration between the robotic arms and between the robotic arms and the table structures) to which the robotic arms are coupled. Even more, as the support flange 1061 and the column 1022 to which the support flange 1061 is coupled are stiffer and more stable than the table top 1020 and the table top adapter 1075 (i.e., the support flange 1061 and the column 1022 have a higher modal frequency), coupling the robotic arms to the support flange 1061 improves stiffness and stability of the system, and can reduce undesirable vibrations at the distal ends of the robotic arms.

Figure 22A:
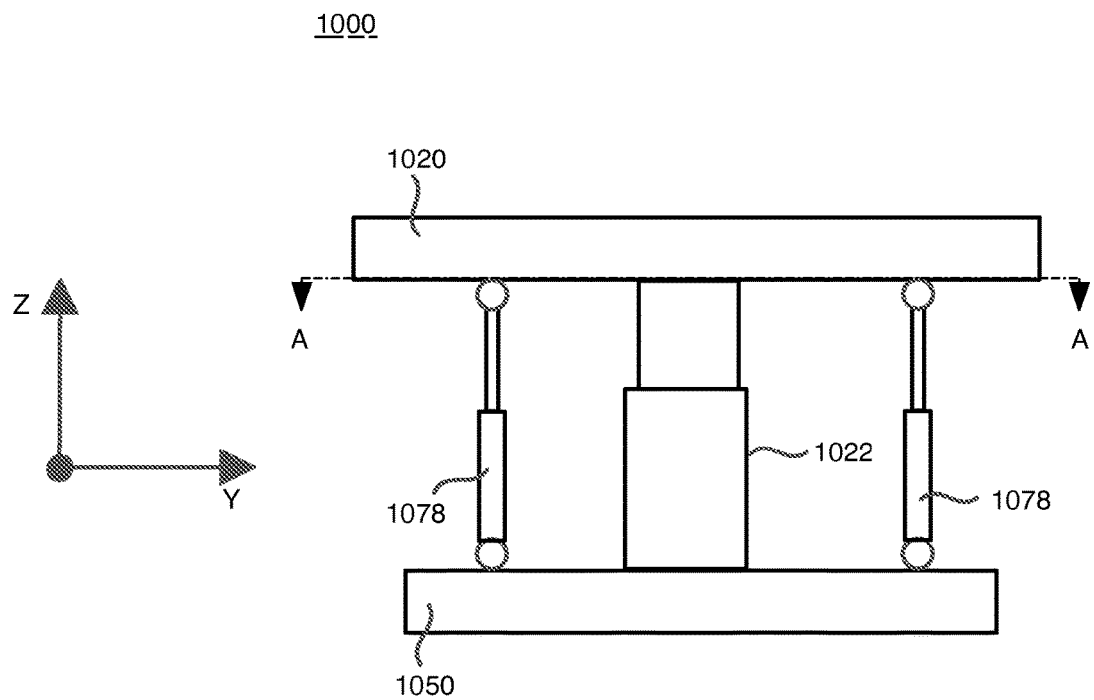
FIGS. 22A and 22B are schematic side and front views, respectfully, of a surgical table having support struts, according to an embodiment.
Figure 22B:
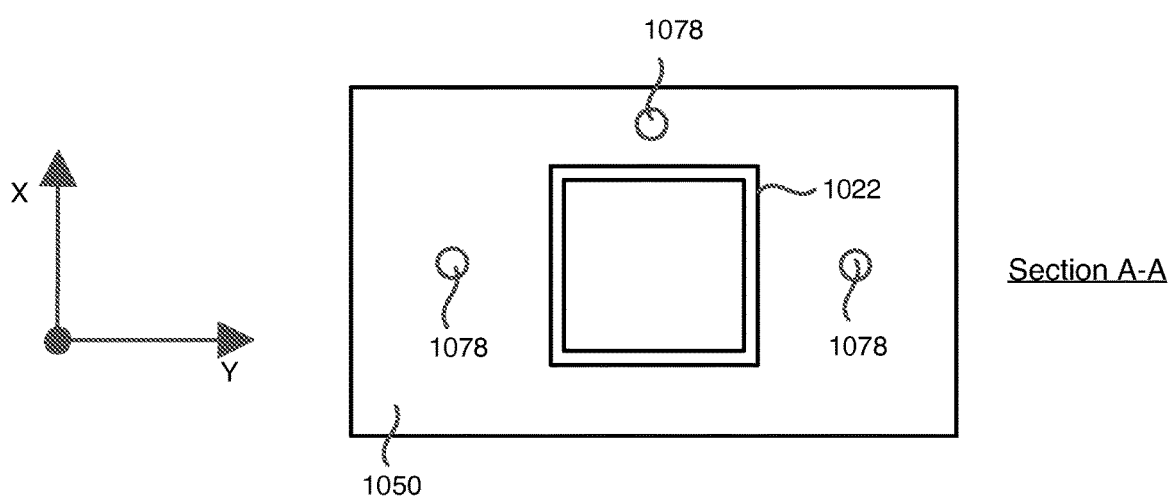
Figures 23A, 23B:
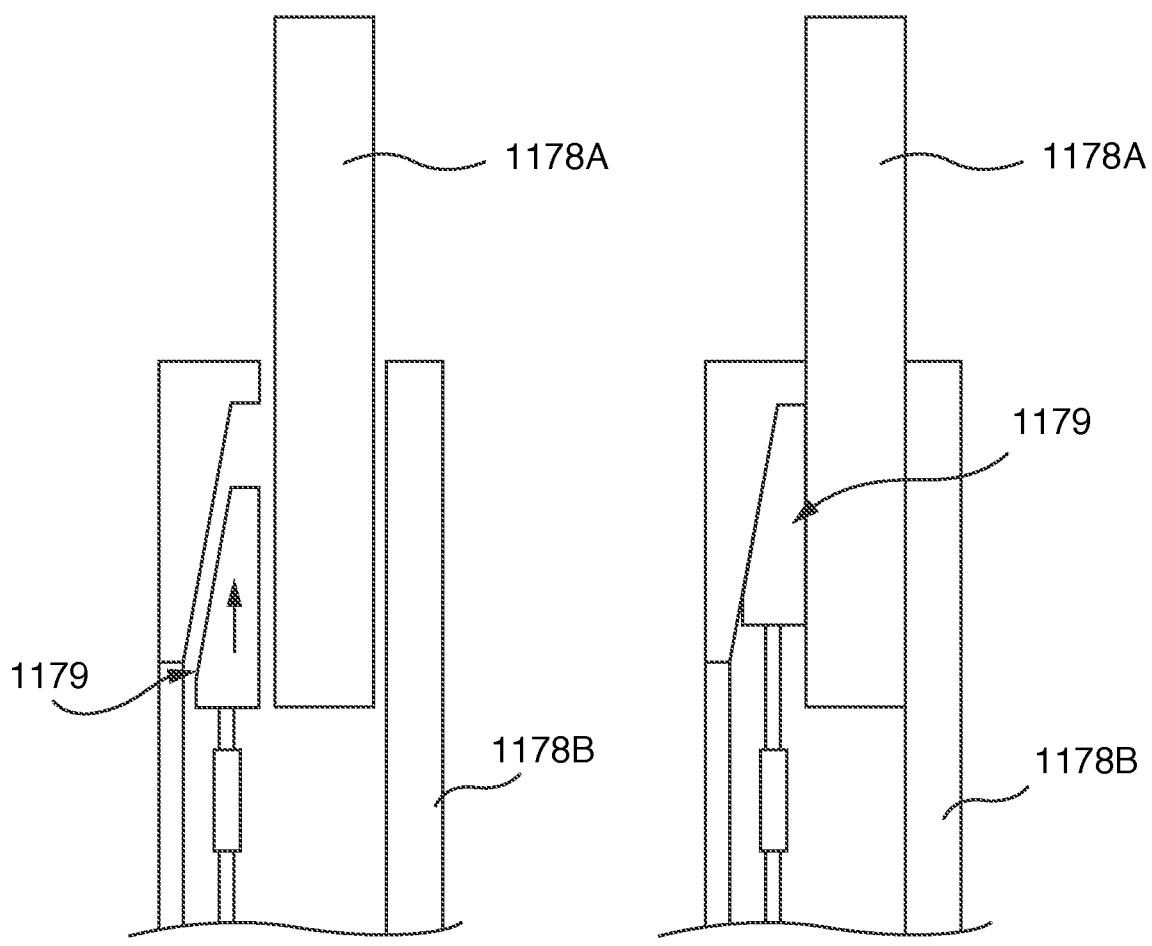
FIG. 23A is a schematic cross-sectional side view of the support strut of FIGS. 22A and 22B, in a first configuration.
FIG. 23B is a schematic cross-sectional side view of the support strut of FIGS. 22A and 22B in a second configuration.

To further stiffen the surgical table and increase its modal frequency and thus reduce undesirable vibrations at the distal ends of robotic arms attached thereto, any of the embodiments described herein can include telescoping and lockable support struts. FIGS. 22A and 22B illustrate such an embodiment. In this embodiment, for ease of description, as illustrated, the surgical table 1100 is shown with only a table top 1120, a table base 1150, a table support or column 1122, and three support struts 1178. The surgical table 1100, however, can be the same as or similar in structure and function to any of the surgical tables described herein. Thus, some details regarding the surgical table 1100 are not described below. It should be understood that for features and functions not specifically discussed, those features and functions can be the same as or similar to any of the surgical tables described herein.

The support struts 1178 are disposed between and coupled to the table top 1120 and the table base 1150, and include an upper section 1178A and a lower section 1178B that telescope relative to each other to provide translation in the Z axis (height above the floor). In this manner, the support struts 1178 can translate simultaneously with the column 1122 and the table top 1120 along the Z axis to place the table top 1120 at a suitable height above the floor. Each support strut 1178 includes a pivot joint (which may be, for example, a gimbal join) at each of its upper and lower ends to allow pivotal or rotational movement of the table top 1120 relative to the support struts 1178 and the column 1122. Each support strut 1178 is lockable, i.e. the telescoping sections can be selectively fixed to each other so that they cannot telescope. In this manner, in use, once the table top 1122 is placed in a desired position above the floor and in a desired orientation (e.g., a desired tilt), the support struts 1178 can be locked. Locking the support struts 1178 provides greater structural resistance to movement of the table top relative to the base and thus can increase the modal frequency of table structures (e.g., the table top 1122) to which the robotic arms (not shown) are coupled. In particularly, the support struts 1178 can limit and/or reduce potential sway of the table top 1178, e.g., as discussed with respect to FIGS. 15A and 15B.

In an alternative embodiment, rather than coupling one or more support struts between the table top and directly to the table base, one or more support struts can have an upper end coupled to the table top and a lower end coupled to the column (e.g., an upper end of the column).

The support struts 1178 can be lockable in any suitable manner. In this embodiment, the support struts 1178 include a brake 1179, as illustrated schematically in cross-section in FIGS. 23A and 23B. As shown, the brake 1179 is disposed between the telescoping sections of the support struts 1178 can be extended from a first position (FIG. 23A), in which the sections of the support struts 1178 are "free following" or otherwise allowed to telescope relative to one another along the Z axis, to a second, engaged position (FIG. 23B) in which the telescoping sections are locked and thus prevented from telescoping relative to one another along the Z axis.

In other embodiments, in addition to or instead of brakes, support struts can include lockable bearings to lock the support struts such that the sections of the support struts cannot telescope relative to one another.

Although in this embodiment the support struts 1178 are shown and described as being located outside of the column 1122, in other embodiments, one or more support struts can be disposed inside of the column.

Further, although in this embodiment the surgical table 1100 includes three support struts, in other embodiments, a surgical table can include any suitable number of support struts (e.g., one support strut, two support struts, four support struts, or more).

In other embodiments, any or all of the support struts 1178 can include more than two sections that telescope relative to each other. In such embodiments, a locking mechanism is provided to selectively lock each section relative to the adjacent section.

As described above, it is desirable to reduce unwanted vibration at the working ends of the robotic arms of a robotic surgical system. Robotic surgical systems can include robotic surgical arms that are coupled to a surgical table via an adapter on which a patient can be supported during a surgical procedure. The robotic surgical arms may support at their distal, working ends various devices, including surgical instruments, cannulae for providing access to the patient's body cavity(ies) and organs) for application of surgical instruments, imaging devices, lights, etc. In such systems, it is desirable to establish and maintain high positional accuracy for the devices mounted on the distal ends of the robotic arms.

Positional accuracy can be reduced or degraded by vibration of the distal ends of the robotic arms. Such vibration may be in the form of vibrational cross-talk, which is unwanted vibration occurring in one part of the system that originates in another part of the system. For example, vibration may be induced within a robotic arm, such as by operation of a motor driving movement of some portion of the arm relative to another portion of the arm and/or to the surgical table or other supporting structure, and the energy introduced into the arm by operation of the motor may propagate through the arm to the distal end, inducing vibration in the distal end. This arm may be referred to as the "active" arm. Alternatively, or additionally, energy introduced into the active arm, such as by operation of a motor within the active arm, may propagate through the active arm, through the table or other supporting structure, and through another robotic arm (which may be referred to as the "passive" arm) to the passive arm's distal end. It is desirable to reduce vibrational cross-talk to enhance positional accuracy of the distal ends of robotic arms and the devices attached thereto.

To address vibrational cross-talk and positional accuracy of the distal ends of robotic arms and the devices attached thereto, apparatus and methods for providing a robotic surgical system including robotic surgical arms that are coupled to a surgical table via an adapter on which a patient can be supported during a surgical procedure are various embodiments described herein with respect to FIGS. 24A-30B.

Apparatus and methods for providing a robotic surgical system including a surgical table having a tabletop on which a patient can be disposed are described herein. In some embodiments, an apparatus includes a surgical table and robotic arms coupled, or coupleable to, the surgical table, with each robotic arm supporting a medical instrument, such as a surgical tool, tool driver, cannula, light, and/or imaging device. The surgical table includes a base, a pedestal or column, and a tabletop coupled to the column. Each of the robotic arms may be coupled to at least one of the tabletop, the column or the base. Each robotic arm provides two or more links between the proximal end of the arm (at which the arm is coupled to the table) and the distal end of the arm (at which the arm is coupled to the medical instrument). The links are coupled to each other, and may be coupled to the table and to the medical instrument, by a joint that provides one or more degrees of freedom of relative movement between the links coupled by the joint, and correspondingly one or more degrees of freedom of relative movement between the distal end of the robotic arm and the surgical table. The links and corresponding degrees of freedom allow for movement of the distal end of the robotic arm about and/or along the X, Y, and/or Z axes, to a desired location relative to the tabletop and/or a patient disposed thereon and/or a desired target portion of the anatomy of a patient disposed thereon. Relative movement of the links about the joints can be initiated and continued by operation of devices such as motors, and/or resisted or stopped by active devices such as motors and/or passive devices such as brakes. As noted above, such devices can introduce energy into the robotic surgical system, which can produce unwanted vibrations at the distal ends of the robotic arms.

In some embodiments, an apparatus includes a surgical table having a patient tabletop, an adapter coupled to the surgical table, and one or more robotic arms coupled to the adapter. In some embodiments, an apparatus can include a surgical table having a patient tabletop and an adapter/robotic arm assembly coupled to the surgical table. For example, the adapter and robotic arm can be an integral mechanism or component. Each of the adapter and the robotic arms, or an adapter/robotic arm assembly, can include one or more links to allow for movement of the adapter and/or arms about and/or along the X, Y, and/or Z axes, to a desired location relative to the tabletop and/or a patient disposed thereon and/or a desired target portion of the anatomy of a patient disposed thereon.

In some embodiments, an apparatus includes an adapter coupleable to, and supportable by, a surgical table below a tabletop of the surgical table. The surgical table has a support coupled to the tabletop and a base coupled to the support. As discussed in more detail herein the adapter is designed to reduce vibrational cross-talk to enhance positional accuracy of the distal ends of the robotic arms and devices attached thereto. To this end, the adapter has at least two sections, including a first section configured to be coupled to a proximal end portion of a first robotic arm and a second section configured to be coupled to a proximal end portion of a second robotic arm. The first section has a first stiffness and the second section has a second stiffness that is greater than the first stiffness. In this manner, the first section with the first stiffness will have a first resonant or modal frequency, and the second section with the second stiffness will have a second resonant or modal frequency different from the first resonant frequency. Varying the resonant frequencies across the adapter can reduce vibrational crosstalk to/front the robotic arms attached to the adapter.

In some embodiments, an adapter, in addition to or instead of having multiple sections with varying stiffness, can define a gap between the first section and the second section. In such embodiments, the apparatus may further include a damper disposed within the gap of the adapter to absorb crosstalk vibration between the robotic arms attached to the adapter. In alternative embodiments, instead of a damper disposed within the gap, an apparatus can include a spring-damper assembly disposed within the gap of the adapter to absorb crosstalk vibration between the robotic arms attached to the adapter.

Figure 24A:
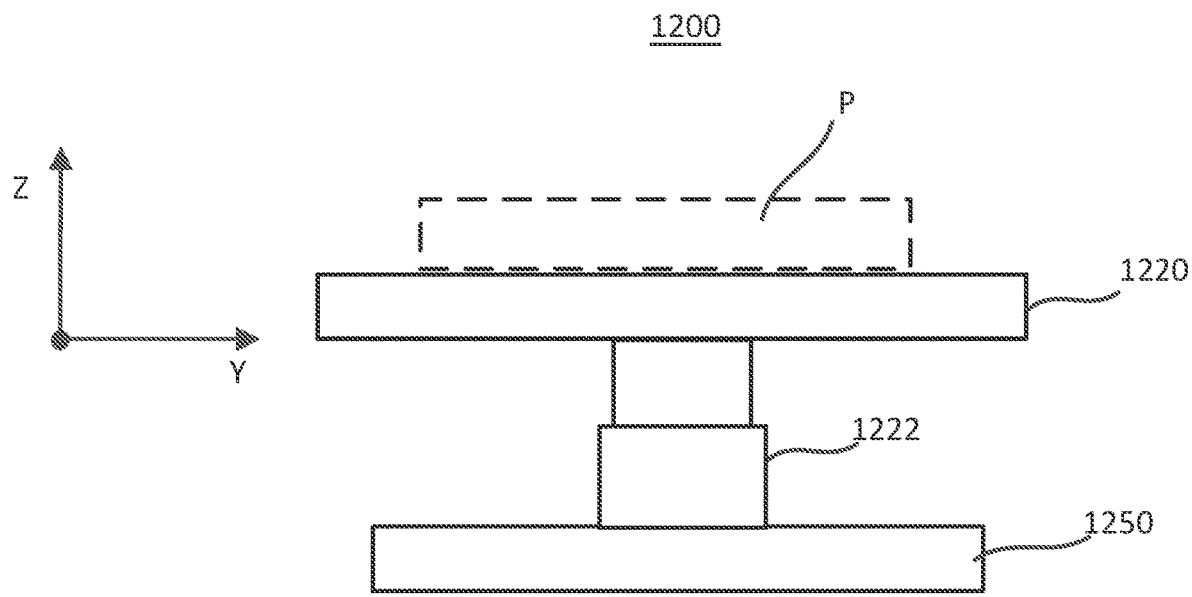
FIGS. 24A and 24B are schematic side and top views, respectively, of a surgical table, according to an embodiment.
Figure 24B:
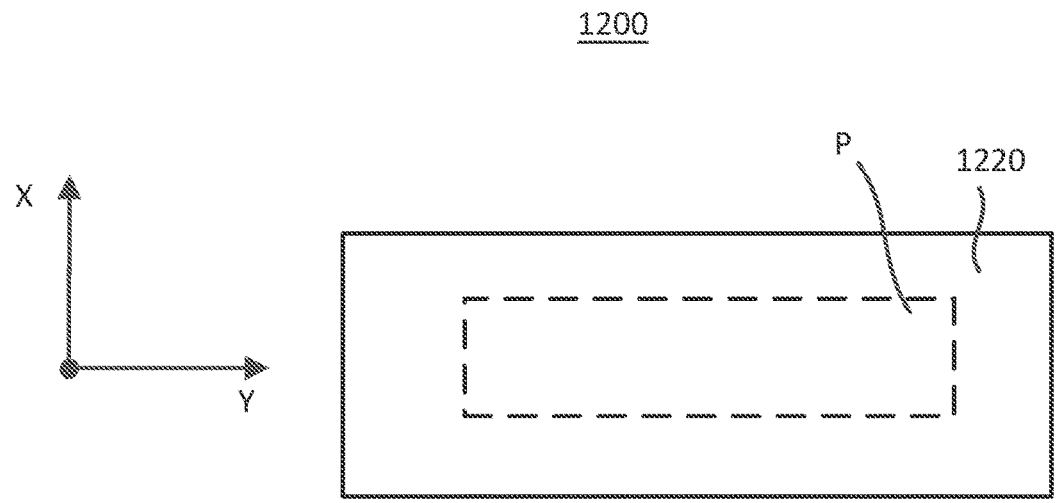

As shown schematically in FIGS. 24A-24B, a surgical table 1200 includes a tabletop 1220, a table support or column 1222 and a table base 1224. The tabletop 1220 has an upper surface on which a patient can be disposed during a surgical procedure, as shown schematically in FIG. 24A. The tabletop 1220 is disposed on the column 1222, which can be, for example, a pedestal, at a suitable height above the floor. The column 1222 may provide for movement of the tabletop 1220 in a desired number of degrees of freedom. For example, as illustrated schematically in FIG. 24A, the column 1222 may have two sections that telescope relative to each other to provide translation in the Z axis (height above the floor). Additionally, or alternatively, the tabletop 1220 may be movable relative to the base 1250 along the Y axis (along the longitudinal axis of the table), and/or the X axis (along the lateral axis of the table), and/or about the Z, Y, and/or X axis. The tabletop 1220 may also include multiple sections that are movable relative to each other along/about any suitable axes, e.g., separate sections for each of the torso, one or both legs, and/or one or both arms, and a head support section. Movement of the tabletop 1220 and/or its constituent sections may be performed manually, driven by motors, controlled remotely, etc. The column 1222 for the tabletop may be mounted to the base 1224, which can be fixed to the floor of the operating room, or can be movable relative to the floor, e.g., by use of wheels on the base. As shown schematically in FIG. 24A, in some embodiments, the height of the column 1222 can be adjusted, which together with, for example, the motion (e.g., axial (longitudinal) or lateral motion) of the tabletop 1220, can allow for the tabletop 1220 to be positioned at a desired surgical site at a certain height above the floor (e.g., to allow surgeon access) and a certain distance from the column 1220. This also can allow robotic arms 1230 coupled to the table 1200 to reach a desired treatment target on a patient disposed on the tabletop 1220.

Figure 24C:
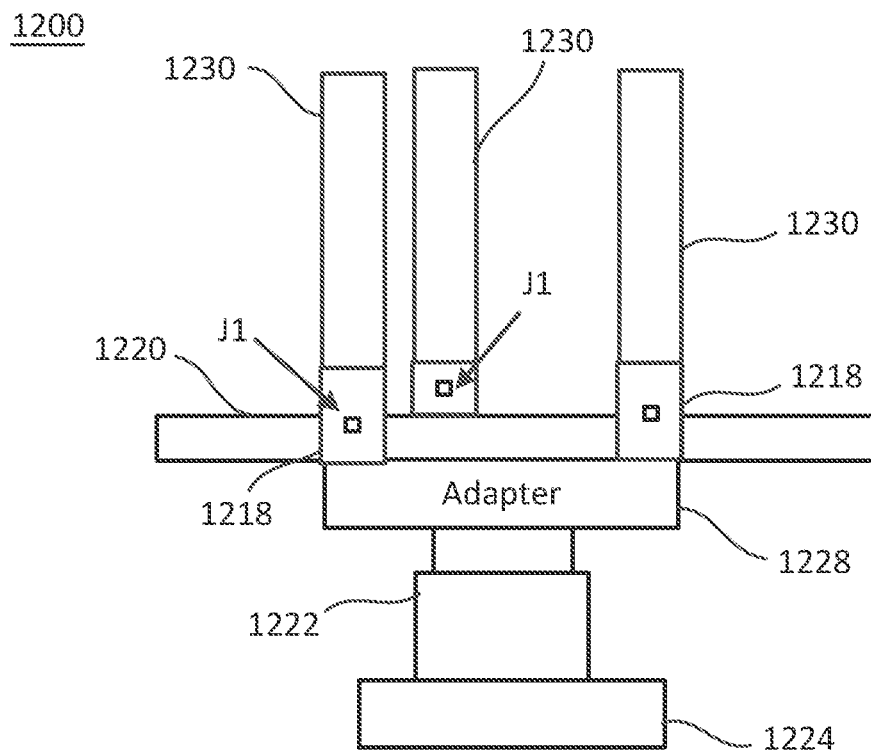
FIGS. 24C and 24D are a schematic side view and a schematic top view, respectively, of the surgical table of FIGS. 24A and 24B with robotic arms coupled thereto.
Figure 24D:
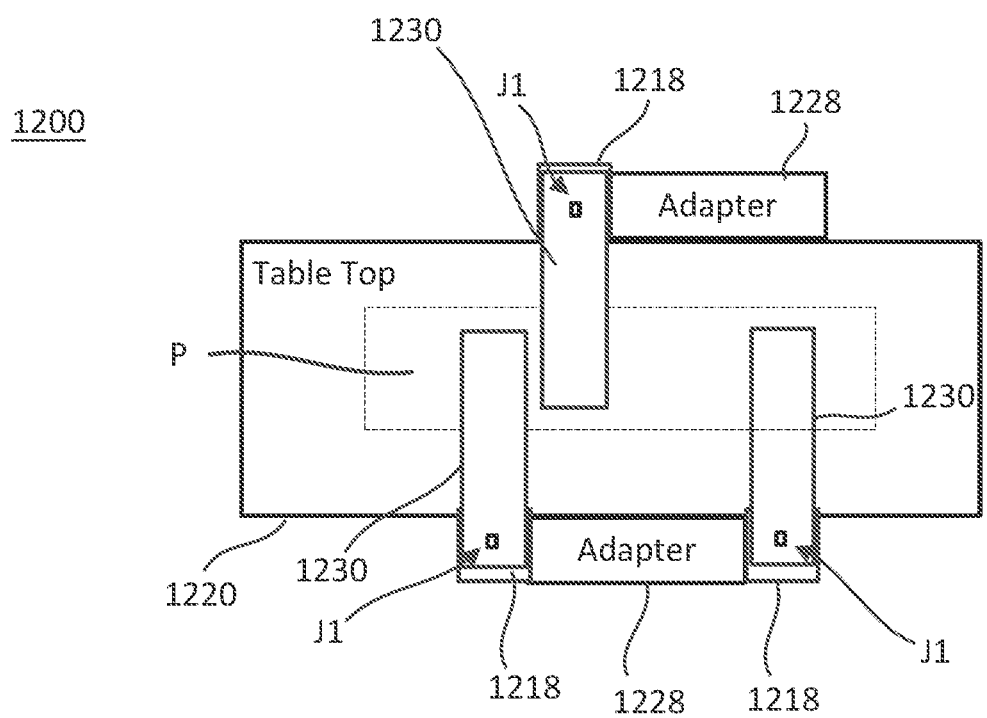

In a robotically assisted surgical procedure, one or more robotic arms 1230 can be disposed in a desired operative position relative to a patient disposed on the tabletop 1220 of the surgical table 1200 (also referred to herein as "table"), as shown schematically in FIGS. 24C and 24D. The robotic arm(s) can be used to perform a surgical procedure on a patient disposed on the surgical table 1200. In particular, the distal end of each robotic arm can be disposed in a desired operative position so that a medical instrument coupled to the distal end of the robotic arm can perform a desired function.

In accordance with various embodiments, the connection between the surgical table and the proximal end of each robotic arm (and thus the position and orientation of the medical instrument at the distal end of the robotic arm relative to the patient), is implemented with an adapter 1228 and robotic arm(s) 1230 coupled to the adapter 1228. The adapter 1228 can be separate from, but engaged with, or coupleable to, the surgical table 1200, or can be fixedly attached to the surgical table 1200. The adapter 1228 can be coupled to, for example, the support 1222, the table base 1224, and/or the tabletop 1220 of the table 1200. As shown schematically in FIGS. 24C and 24D, the adapter 1228 is disposed below the tabletop 1220 of the surgical table 1200.

In use, the robotic arms 1230 can be moved relative to the tabletop 1220 and/or a specific target treatment location on the patient. In some embodiments, the axial motion (e.g., in the Y-axis direction) of the tabletop 1220 can assist in allowing the arms 1230 (and therefore, the medical instrument or tool coupled to the distal end of the arm) to reach the desired anatomy on the patient or provide clearance for access to the patient as needed. In some embodiments, the combination of vertical movement of the column 1222, axial movement of the tabletop 1220 and movement of, for example, links in the robotic arm 1230 allow the robotic arm to be placed in a position where it can reach the anatomy of the patient at the required height over the floor.

Figure 25A:
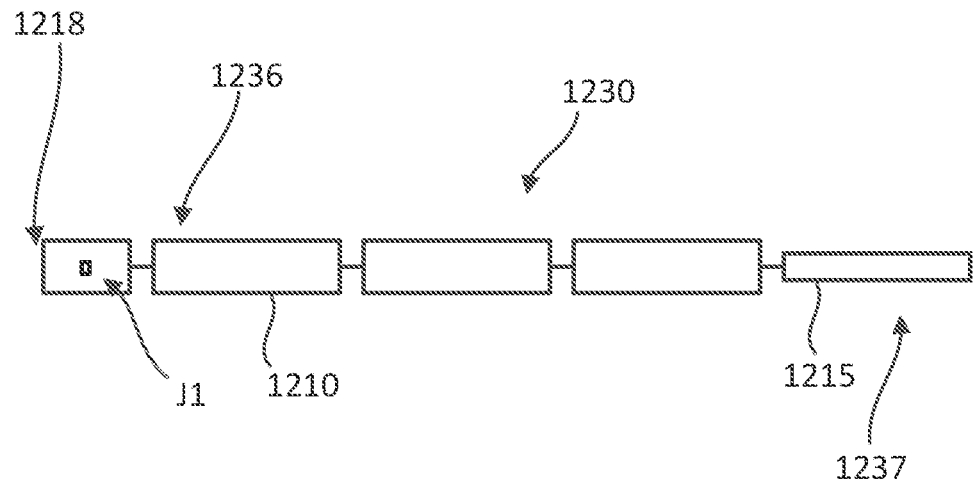
FIG. 25A is a schematic side view of a robotic arm, according to an embodiment, shown in an extended or use configuration.
Figure 25B:
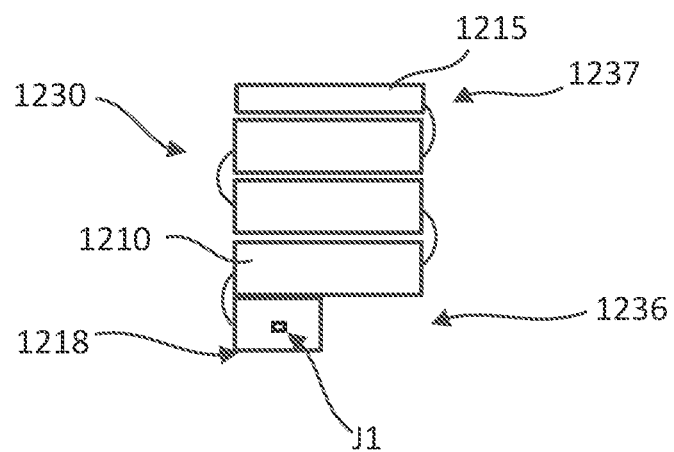
FIG. 25B is a schematic side view of the robotic arm of FIG. 25A, shown in a collapsed or folded configuration.

As shown schematically in FIGS. 25A and 25B, each robotic arm 1230 can include a distal end portion 1237 and a proximal end portion 1236. The distal end portion 1237 (also referred to herein as "operating end") can include or have coupled thereto a medical instrument or tool 1215. The proximal end portion 1236 (also referred to herein as the "mounting end portion" or "mounting end") can include the coupling portion to allow the robotic arm 1230 to be coupled to the tabletop 1220 of the table 1200. The robotic arm 1230 can include two or more link members or segments 1210 coupled together at joints that can provide for translation along and/or rotation about one or more of the X, Y and/or Z axes. The coupling portion of the robotic arm 1230 to couple the robotic arm 1230 to the tabletop 1222 at the coupling 1218 can be disposed at the distal or mounting end 1236 of the arm 1230 and may be coupled to a segment 1210 or incorporated within a segment 1210. The robotic arm 1230 also includes a target joint J1 disposed at or near the mounting end 1236 of the robotic arm 1230 that can be included within the coupling portion of the coupling 1218 or disposed on a link or segment 1210 of the robotic arm 1230 coupled to the coupling portion. The target joint J1 can provide a pivot joint to allow a distal segment of the robotic arm 1230 to pivot relative to the tabletop 1220. The robotic arm 1230 can be moved between various extended configurations for use during a surgical procedure, as shown in FIG. 25A, and various folded or collapsed configurations for storage when not in use, as shown in FIG. 25B.

As described with respect to FIGS. 24C and 24D, the adapter 1228 can be coupled to, for example, the column 1222, the table base 1224 and/or the tabletop 1220 of the table 1200. However, the distinction between an adapter and robotic arm can be disregarded, and the connection between the surgical table and the distal end of the robotic arm can be conceptualized and implemented as a series of links and joints that provide the desired degrees of freedom for movement of the medical instrument, i.e. at the distal end of the connection. The connection may include a releasable coupling at any one or more link(s) or joint(s) or any location along the series of links and joints.

As described herein, in some embodiments, the various sections of the tabletop 1220 can move relative to each other (e.g., can be tilted or angled relative to each other) and/or the tabletop 1220 can be moved (tilted, angled) relative to the column 1222 and/or the base 1224 of the surgical table 1200. In some embodiments, it is contemplated that the adapter 1228 and robotic arms 1230 coupled thereto can move with the torso section of the tabletop 1220 such that the frame of reference to the X, Y and Z axes for various embodiments remains relative to the top surface of the tabletop 1220. In some embodiments, the adapter 1228 and robotic arms 1230 can be coupled to the support pedestal 1222 of the table 1200 and when the tabletop 1220 is moved relative to the support 1222, the positioning of the adapter 1228 and arms 1230 can be coordinated with the movement of the tabletop 1220.

In accordance with various embodiments, each robotic arm 1230 may be permanently, semi-permanently, or releasably coupled to the adapter 1228 via the coupling 1218. The coupling 1218 can include a variety of different coupling mechanisms, including a coupling portion (not shown) on the adapter 1228 that can be matingly coupled to a coupling portion (not shown) on the robotic arm. Each robotic arm 1230 can be coupled at a fixed location on the table 120 or can be coupled such that the robotic arm 1230 can be movable to multiple locations relative to the tabletop 1220 and/or a patient disposed on the tabletop 1220 as described in more detail herein. For example, the robotic arm 1230 can be moved relative to the tabletop 1220 and/or a specific target treatment location on the patient. In some embodiments, the axial motion (e.g., in the Y-axis direction) of the tabletop 1220 can assist in allowing the arms 1230 (and therefore, the medical instrument or tool coupled to the distal end of the arm) to reach the desired anatomy on the patient or provide clearance for access to the patient as needed. In some embodiments, the combination of vertical movement of the support pedestal 1222, axial movement of the tabletop 1220 and movement of, for example, one or more link members, allows for placement of the robotic arms 1230 in a position where it can reach the anatomy of the patient at the required height over the floor.

Some structural requirements for the adapter 1228 can include providing a rigid support of the robotic arm 1230 while maintaining adjustability for pre-operative and intra-operative position changes of the robotic arm 1230. In some embodiments, the table adapter 1228 can include a means of holding or locking the adapter 1228 at a fixed position to withstand, for example, the effects of gravity, inertial effects due to robotic arm motion, and/or to withstand accidental bumps from a user or another part of the robotic system (including other robotic arms or table motion). The table adapter 1228 can also include one or more sensors for measuring the spatial position of the adapter 1228 and/or angles and displacements of various joints and coupling points of the adapter 1228.

The various degrees of freedom of the links of the adapter 1228 and/or robotic arm 1230 provide for movement of the robotic arm 1230 and therefore, a medical instrument 1215 disposed at a distal end thereof to be moved to a variety of different positions and orientations relative to the tabletop 1220 to perform various different procedures on a patient disposed thereon. The adapters 1228 described herein can also provide for variations on the number of robotic arms 1230 that are coupled to the table to use for a particular procedure, and to position robotic arms 1230 on one or both sides of the tabletop 1220. For example, in some procedures, it may be desirable to position two robotic arms 1230 on one side of the tabletop 1220 and two robotic arms 1230 on an opposite side of the tabletop 1220. In other procedures, it may be desirable to position three robotic arms 1230 on one side of the tabletop 1220 and one robotic arm 1230 on an opposite side of the tabletop 1220. It should be understood that the number of robotic arms 1230 to be used for a particular surgery can vary.

Figure 26:
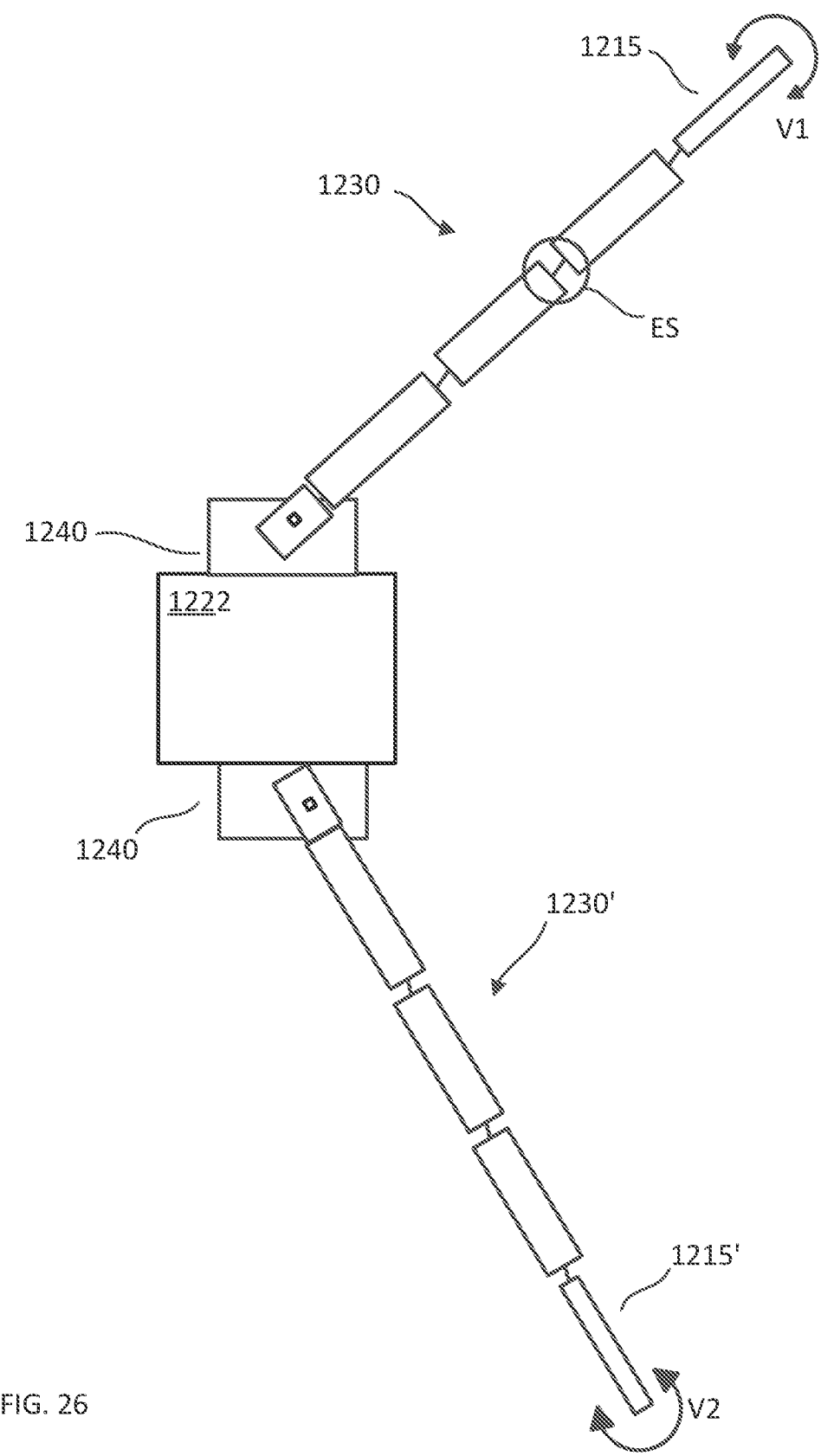
FIG. 26 is a schematic illustration of a top view of a portion of the surgical table, adapter and robotic arm of FIGS. 24A-25B, illustrating induced unwanted vibrational transmissions.

As shown schematically in FIG. 26, an energy source ES, such as motor at a joint between two links in active arm 1230, in use, can induce unwanted vibration V1 in tool 1215 of active arm 1230, and/or vibration V2 in tool 1215' of passive arm 1230' via interface structure(s) 1240 and column 1222. For example, energy introduced by the energy source ES in the active arm 1230 may propagate through the active arm 1230, through the interface structure(s) 1240 and column 1222 and through the passive arm 1230' to the tool 1215' of the passive arm 1230', inducing vibration V2 in tool 1215'. It is desirable to reduce such vibrational cross-talk from energy source ES of active arm 1230 to tool 1215 of active arm 1230 and to tool 1215 of passive arm 1230' to enhance positional accuracy of the tool 1215 of active arm 1230 and tool 1215' of passive arm. In some instances, various components along/about each of three axes of the system may be subject to varying vibrations. In such instances, it is desirable to reduce amplitude of at least the most critical components, if not all of the components, to enhance positional accuracy of the distal ends of the robotic arms and the devices attached thereto.

FIGS. 27A-28B illustrate various embodiments of apparatus and methods for reducing vibrational cross-talk by separation the modal frequencies of vibration across various sections of the table structure(S) (e.g., a table adapter) to which the robotic arms are coupled, and/or by isolating at least in part the connection points of the table structure(s) to which the robotic arms are coupled.

To limit vibrational cross-talk across an adapter to which robotic arms are coupled, in some embodiments, an adapter can have multiple sections in which one section has a modal frequency of vibration different from a modal frequency of vibration of one or more of the remaining sections. Decoupling the modal frequencies of the sections of the adapter reduces the efficiency of transmission of the energy introduced into the active arm. For example, if an active robotic arm has a mode of 4 Hertz (Hz), energy introduced into the active robotic arm is best transferred across the adapter to another robotic arm (e.g., a passive robotic arm) when the adapter has a mode equal to the mode of the active robotic arm; in this case, a mode of 4 Hz. Transmission of the energy across the adapter can be lessened and/or interrupted by arranging the adapter to have varying modal frequencies of vibration, thereby creating modal separation between one connection point of the adapter to another connection point of the adapter. Less energy transmitted between the connection points (and thereby the robotic arms coupled to the connection points) results in less vibration produced, e.g., at the passive arm.

To vary the modal frequency of an adapter to interrupt energy transfer across the adapter, in some embodiments, an adapter can have multiple sections each having a characteristic different from a characteristic of at least one other section of the adapter, the different characteristic(s) resulting in a different modal frequency for each section. A characteristic, for example, can include dimensions (e.g., width, height, and/or length) and/or geometry, such as the presence of absences of ribs, flanges, or other configurations that affect the moment of inertia about the axis or axes of interest for response to vibration. Thus, the table adapter can be monolithically or integrally formed of a single material but each section can be formed with different dimensions and/or geometries. Alternatively, or in addition, the multiple sections can be formed of one or more different materials, or combinations of materials, that have different physical properties, such as modulus of elasticity, density, and the like.

Figure 27A:
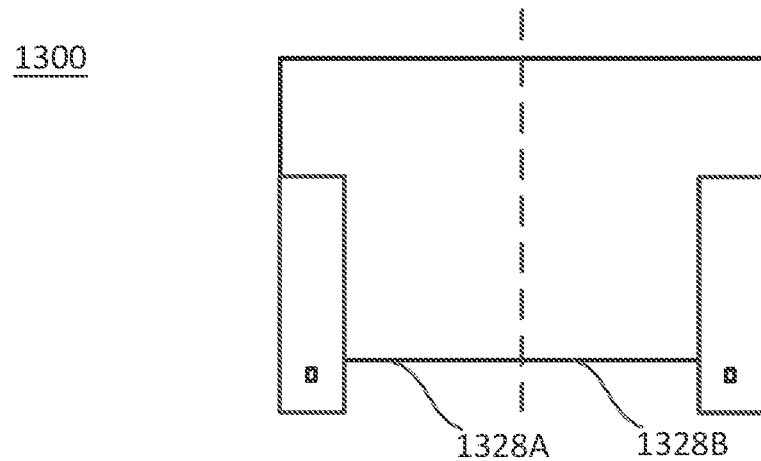
FIGS. 27A and 27B are schematic top and side views, respectively, of an adapter for a surgical table having a first section with a first thickness and a second section with a second thickness different from the first thickness, according to an embodiment.
Figure 27B:
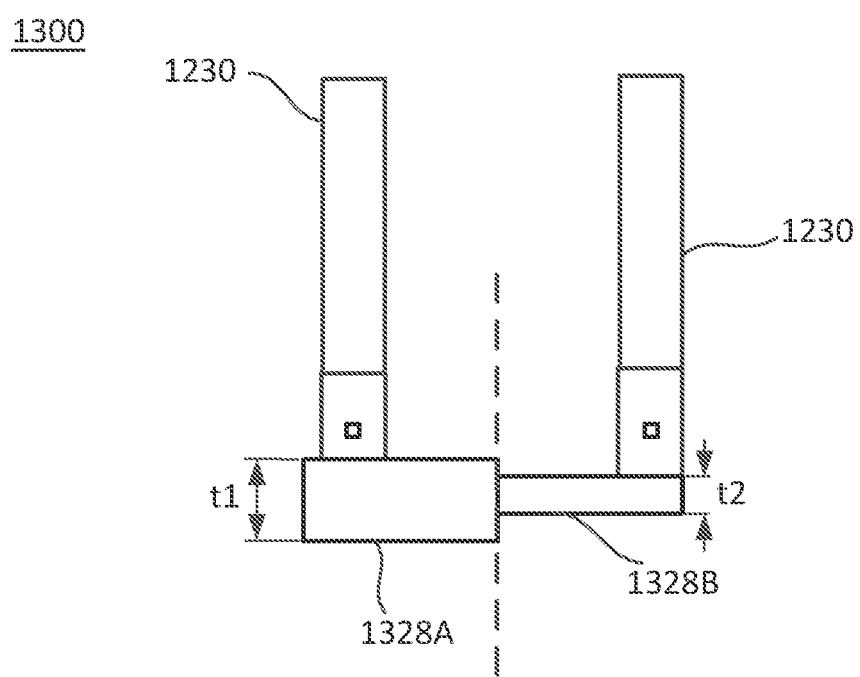

As an example, FIGS. 27A and 27B illustrate an adapter 1328 having a first section 1328A with a first thickness t1 and a second section 1328B with a second thickness t2 less than the first thickness, according to an embodiment. In this manner, the first section 1328' has a mode different from a mode of the second section 1328B, thereby lessening energy transfer from one robotic arm 130, across both the first section 1328A and second section 1328B, to another robotic arm 130. In this example, adapter 1328 may be monolithically or integrally formed from a single material. Alternatively, adapter 1328 may be assembled from multiple pieces, e.g. first section 1328A and second section 1328B may be integrally formed of a material of thickness t2, and a separate piece of the same material may be fixed to first section 1328A to increase the thickness to t1, as illustrated in FIG. 27C. Alternatively, one or more of the sections 1328A and 1388B may be formed of a composite or laminate of different materials with different physical properties In alternative configurations, instead of or in addition to the first section and the second sections having different thicknesses, the first section can have any characteristic(s) affecting its mode different from one or more characteristics of the second section affecting the mode of the second section. For example, in some embodiments, the first section of the adapter can be shaped or configured to have a first moment of inertia or stiffness, and the second section of the adapter can be shaped or configured to have a second moment of inertia or stiffness different from the first stiffness. In this manner, the first section of the adapter can be configured to have a higher mode than the mode of the second section, thereby reducing efficiency of energy transmission between the first and second sections. Such an example is illustrated in FIGS. 27D and 27E in which the first section 1328A of the adapter 1328 includes a set of ribs 1327. In this manner, first section 1328A with the ribs 1327 has a moment of inertia different from a moment of inertia of the second section 1328B. The ribs 1327 can be monolithically formed or integral to the first section 1328, or the ribs 1327 can be formed separately and then coupled to the first section 1328, or a combination of the two. Further, although this embodiment includes three ribs, in alternative embodiments, any suitable number of ribs (e.g., 1, 2, 4 or more) can be used, and the ribs can be of the same or varying sizes and shapes. Moreover, although the adapters described herein having two sections, in alternative embodiments, an adapter can have any suitable number of sections (e.g., 3, 4, 5, 6 or more), each to support a different robotic arm, with any variation of modal frequencies such that undesirable vibrational cross-talk is reduced or otherwise limited.

An additional or alternative approach to reducing vibrational cross-talk can include decoupling in part (e.g., limit direct coupling) the connection points of the adapter to which the robotic arms are coupled. Isolating the connection points to which the robotic arms are coupled or otherwise interrupting energy transfer pathways (e.g., via separation, dampening, varying materials and dimensions, and the like) between those connection points reduces the efficiency of transmission of the energy introduced into the active arm by, for example a motor and/or brake. For example, energy introduced into the active robotic arm is best transferred to a passive robotic arm when the intervening structure (e.g., a table adapter) to which the two arms are mounted presents minimal obstacles to energy transfer (e.g., via a direct coupling). Transmission of the energy introduced into the active robotic arm across the intervening structure can be lessened and/or interrupted by various means discussed below, thereby complicating the pathway energy would need to transfer to reach the connection points, thereby reducing the efficiency of energy transmission to the passive arm. Less energy transmitted between arms results in less vibration produced, i.e. lower amplitude in/about one or more axes.

Figure 28A:
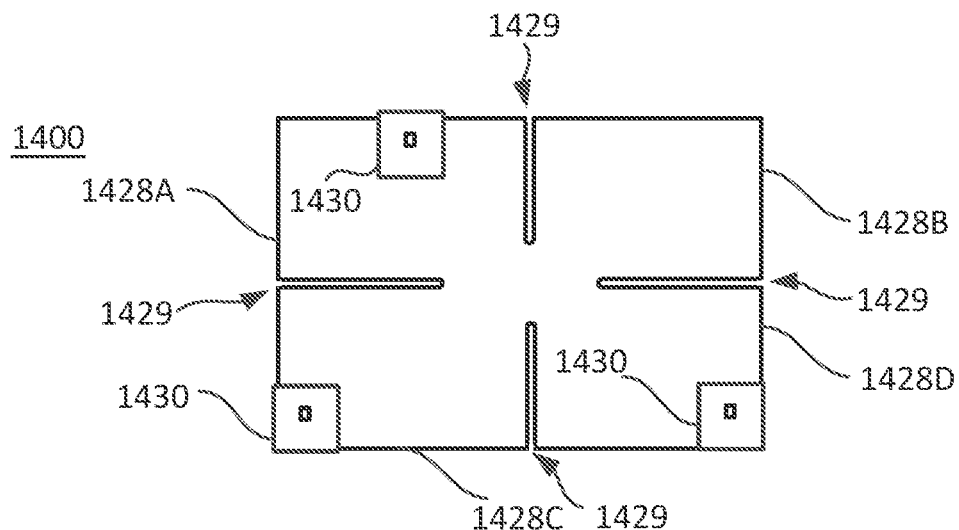
FIGS. 28A and 28B are schematic top and side views, respectively, of an adapter for a surgical table, according to another embodiment.
Figure 28B:
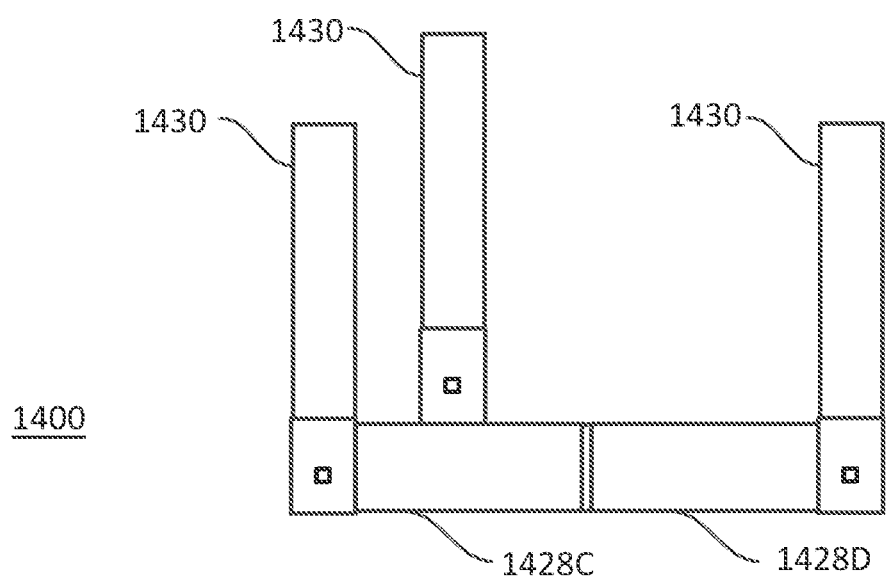

FIGS. 28A and 28B illustrate such an embodiment whereby the connections points of an adapter 1428 are isolated in part from each other. As shown, the adapter 1428 includes a first section 1428A, a second section 1428B, a third section 1428C, a fourth section 1428D (also referred to herein collectively as the "sections of the adapter"), with robotic arms coupleable to a connection portion of the first section 1428A, the second section 1428B, and the third section 1428C. Further, as illustrated, the adapter defines a set of gaps 1429 between the sections of the adapter 142$. In this manner, the gaps 1429 provide partial separation/decoupling of the sections of the adapter 1428 to each other, resulting in less efficient transmission of energy across the adapter, e.g., from a connection point to which an active robotic arm is coupled to a connection points to which a passive robotic arm is coupled. In other words, the vibrational energy must travel through the central portion of adapter 1428, which may be coupled to the tabletop and/or the table column (not shown) and thus has a relatively higher stiffness and modal frequency than that of either of the adapter sections.

Figure 29A:
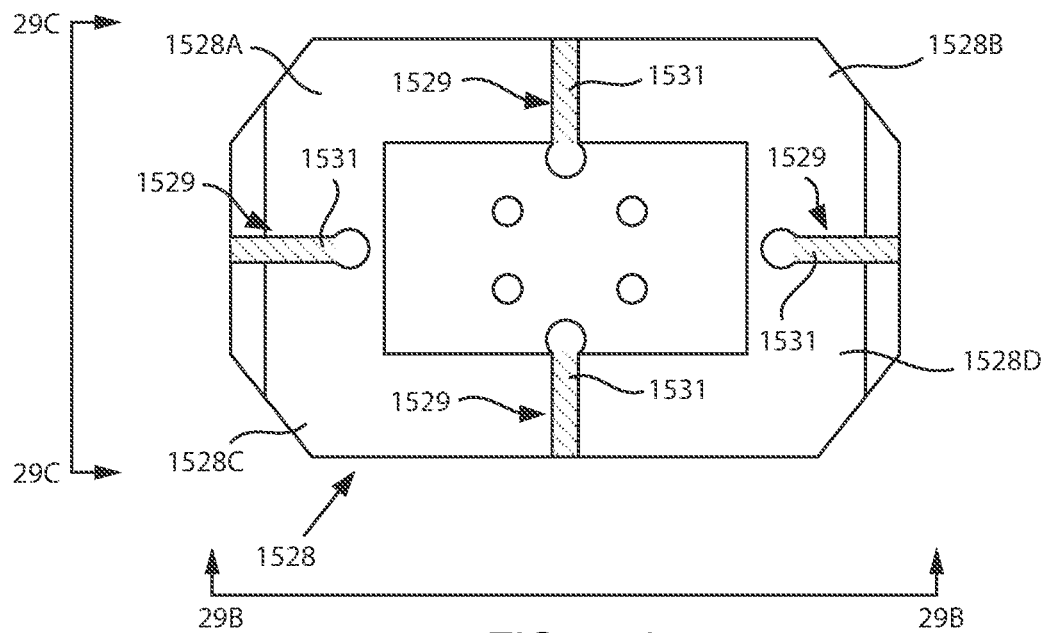
FIGS. 29A-29C are schematic top, side, and front views, respectively, of an adapter for a surgical table having a damping component, according to an embodiment.
Figure 29B:
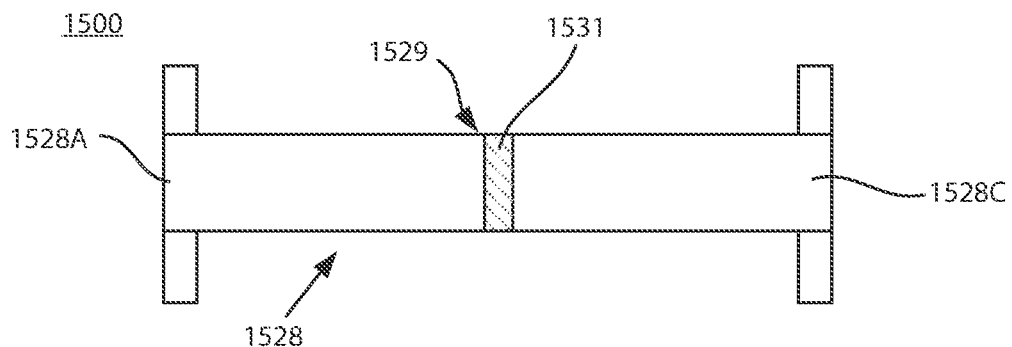
Figure 29C:
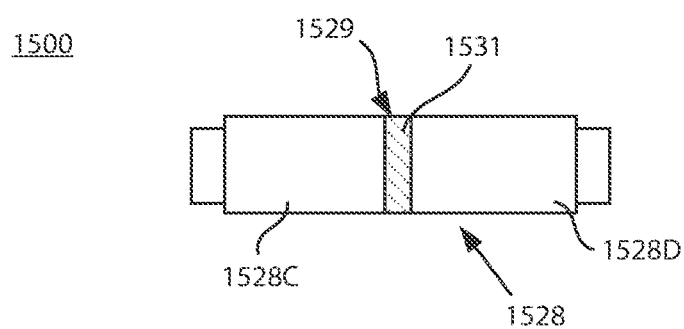
Figure 30A:
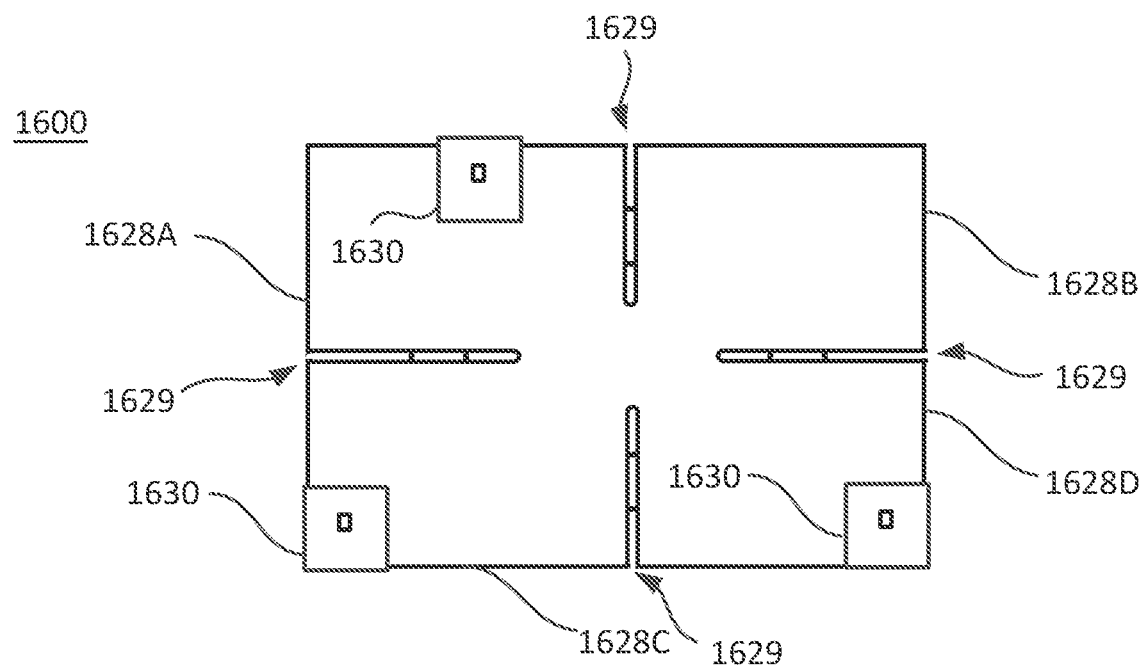
FIGS. 30A and 30B are schematic top and side views, respectively, of an adapter for a surgical table having a damper assembly, according to an embodiment.
Figure 30B:
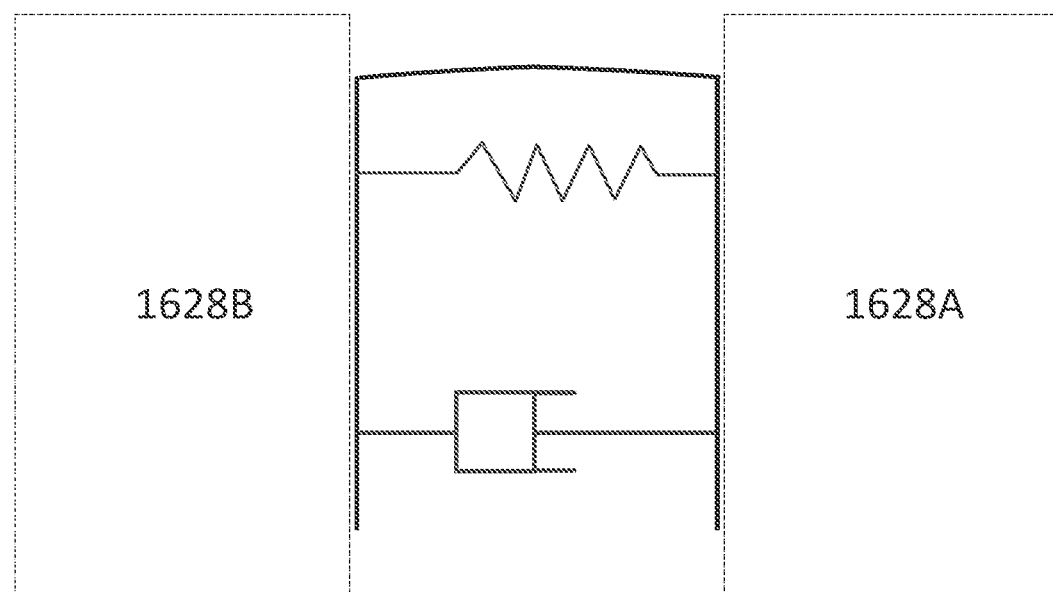

In some embodiments, one or more (e.g., including all) of the gaps between sections of an adapter can include a damping component configured to absorb or otherwise dissipate energy introduced into the adapter at its connection points to which the robotic arms are coupled, thereby reducing or otherwise limiting vibrational cross-talk in the system. One such embodiment is shown in FIGS. 29A-29C. As shown, the adapter 1528 includes a first section 1528A, a second section 1528B, a third section 1528C, and a fourth section 1528, with gaps 1529 defined therebetween. Further, disposed within each gap 1529 is a damping component 1531. Each of the damping components 1531, for example, can include at least one viscoelastic material (e.g., a viscoelastic polymer) or otherwise any material that exhibits both viscous and elastic characteristics when undergoing deformation, and is suitable for isolating vibration, dampening noise, and/or absorbing shock. Some non-limiting examples of viscoelastic materials include urethane polymers such as Sorbothane® (Sorbothane, Inc.), vulcanized cross-linked rubber material such as Akton® (Action Products, Inc.), hydrophobic melamine foams such as Polydamp® (Polymer Technologies, Inc.), and viscous damping gels such as NyeMed® (Nye Lubricants, Inc.). The damping between any two adjacent sections, i.e. across one of the gaps 1529, can be varied by varying the material and/or the dimensions of the material, i.e. the width of the gap and/or the portion of the length and or vertical extent of the gap filled by the material.

In another embodiment, one or more of the gaps in the adapter can have disposed therein a damper assembly. As shown schematically in FIGS. 30A and 30B, damper assembly 1632 can be coupled to adjacent sections 1628A, 1628B of adapter 1628, across gap 1629 (and similarly to adjacent sections 1628A, 1628C, adjacent sections 16280, 1628D, and adjacent sections 1628B, 1628D). Damper assembly 1632 can include a damper, shown schematically in FIGS. 30A and 30B as dashpot, which provides a resistance to relative movement of sections 1628A, 1628B that is proportional to the velocity of the relative movement. This may be implemented as a hydraulic or pneumatic damper, in which a fluid is forced through an orifice by relative movement of sections 1628A, 1628B. As shown schematically in FIGS. 30A and 30B, damper assembly 1632 may also include a structure that functions as a spring, i.e. produces a force that is proportion to the relative displacement between sections 1628A, 1628B. The damping and spring coefficients for damper assembly 1632 may be selected to provide the desired response function to reduce the transfer of energy across gap 1629.

Any suitable combination of damping components can be used to dampen energy otherwise being transferred across sections of the adapter, thereby limiting and/or reducing undesirable vibrational cross-talk in the system. Further, although adapters 1428 and 1528 are shown and described as having four sections and four gaps, in alternative embodiments, an adapter can have any suitable number of sections and gaps, and the sections and gaps can be similar or different in shape and size to each other.

Although various embodiments have been described as having particular features and/or combination of components, other embodiments are possible having a combination of any features and/or components from any of the embodiments described herein. For example, any of the bases e.g., table base 150, 250, 350, 550, 650, 750, etc.) described herein can be used in combination with any of the supports (e.g., table support 122, support member 262, table support 1122, etc.), and/or adapters (e.g., adapter 528, adapter coupling 975, adapter coupling 1075, etc.) described herein. Similarly stated, for ease of explanation some embodiments described herein focus on discrete features to address particular shortcomings of existing systems. It should be understood, however, that the discrete features described across various embodiments can be combined into a single embodiment in any suitable combination. For example, in some embodiments, a surgical system may include a base (e.g., similar to base 250) configured to remedy undesirable consequences associated with irregularities in a floor or other surface on which a surgical table is disposed and/or other undesirable load imbalances (e.g., due to movement if equipment coupled to table and/or movement of patient lying on table) during a surgical procedure; an adapter (e.g., adapter 528) configured to facilitate desired degrees of freedom for movement of a robotic arm coupled thereto and/or having varying sections of modal frequency or other features to inhibit vibrational cross-talk; and a pivot assembly (e.g., pivot assembly 660).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a field-programmable gate array (FPGA), an application specific integrated circuit (ASIC), a digital signal processor (DSP)) and/or software-based module (e.g., a. module of computer code stored in memory and/or executed at the processor) capable of performing one or more specific functions associated with that module.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC), Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Where schematics and/or embodiments described above indicate certain components arranged in certain orientations or positions, the arrangement of components may be modified. Similarly, where methods and/or events described above indicate certain events and/or procedures occurring in certain order, the ordering of certain events and/or procedures may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The invention claimed is:

1. An apparatus, comprising:
   an adapter coupled to a surgical table below a tabletop of the surgical table, the surgical table having a support coupled to the tabletop and a base coupled to the support,
   the adapter having a first section coupled to a proximal end portion of a first robotic arm and a second section coupled to a proximal end portion of a second robotic arm, the first section having a first stiffness and the second section having a second stiffness greater than the first stiffness, a distal end portion of the first robotic arm coupled to a first surgical tool and a distal end portion of the second robotic arm coupled to a second surgical tool.

2. The apparatus of claim 1, wherein the first section of the adapter has a first thickness and the second section of the adapter has a second thickness greater than the first thickness.

3. The apparatus of claim 1, wherein the first section of the adapter is formed from a first material and the second section of the adapter is formed from a second material different from the first material.

4. The apparatus of claim 1, wherein the adapter further includes a third section disposed between the first section and the second section, the third section having a third stiffness greater than both the first stiffness and the second stiffness.

5. The apparatus of claim 4, wherein the third section has a third thickness greater than both the first thickness and the second thickness.

6. The apparatus of claim 1, wherein the adapter is coupled to the support of the surgical table.

7. An apparatus, comprising:
   an adapter coupled to a surgical table below a tabletop of the surgical table, the surgical table having a support extending upwardly from a base, wherein the tabletop is coupled to the support,
   the adapter having a first section coupled to a proximal end portion of a first robotic arm and a second section coupled to a proximal end portion of a second robotic arm, the first section and the second section defining a gap therebetween; and
   a damper disposed within the gap of the adapter to absorb crosstalk vibration between the first robotic arm and the second robotic arm.

8. The apparatus of claim 7, wherein the damper is formed of elastomeric material.

9. The apparatus of claim 7, wherein the adapter is coupled to the support of the surgical table.

10. An apparatus, comprising:
    an adapter coupled to a surgical table below a tabletop of the surgical table, the surgical table having a support extending upwardly from a base, wherein the tabletop is coupled to the support,
    the adapter having a first section coupled to a proximal end portion of a first robotic arm and a second section coupled to a proximal end portion of a second robotic arm, the first section and the second section defining a gap therebetween; and
    a spring-damper assembly disposed within the gap of the adapter to absorb crosstalk vibration between the first robotic arm and the second robotic arm.

11. The apparatus of claim 10, wherein the adapter is coupled to the support of the surgical table.

12. The apparatus of claim 10, wherein the adapter is disposed between the tabletop and the support.

13. The apparatus of claim 10, wherein the spring-damper assembly comprises a dashpot that is coupled to the first section and is coupled to the second section.

14. The apparatus of claim 13, wherein the spring-damper assembly further comprises a spring structure that is coupled to the first section and is coupled to the second section.

15. The apparatus of claim 10, wherein the gap is a first gap, wherein the adapter further comprises a third section coupled to a proximal end portion of a second robotic arm, the second section and the third section defining a second gap therebetween, wherein the apparatus further comprises a damper component disposed within the second gap.

16. The apparatus of claim 9, wherein the adapter is disposed between the tabletop and the support.

17. The apparatus of claim 16, wherein the adapter comprises a central portion that is coupled to the first section and the second section.

18. The apparatus of claim 17, wherein the central portion of the adapter is coupled to the tabletop and to the support.

19. The apparatus of claim 9, wherein the first section and the second section form the adapter as an integrated unit.

20. The apparatus of claim 1, wherein the second section comprises one or more ribs or flanges integrated therein.

21. The apparatus of claim 1, wherein the proximal end portion of the first robotic arm and the proximal end portion of the second robotic arm are removably coupled to the first section and the second section, respectively.

* * * * *